(12) United States Patent
Gustafsen et al.

(10) Patent No.: US 11,173,177 B2
(45) Date of Patent: Nov. 16, 2021

(54) COMPOUNDS FOR TREATMENT OF LIPOPROTEIN METABOLISM DISORDERS

(71) Applicant: Aarhus Universitet, Aarhus C (DK)

(72) Inventors: Camilla Gustafsen, Aarhus C (DK); Peder Sondergaard Madsen, Risskov (DK); Simon Glerup Pedersen, Risskov (DK)

(73) Assignee: Aarhus Universitet, Aarhus C (DK)

( * ) Notice: Subject to any disclaimer, the term of this patent is extended or adjusted under 35 U.S.C. 154(b) by 0 days.

(21) Appl. No.: 16/334,131

(22) PCT Filed: Sep. 20, 2017

(86) PCT No.: PCT/EP2017/073747
§ 371 (c)(1),
(2) Date: Mar. 18, 2019

(87) PCT Pub. No.: WO2018/054959
PCT Pub. Date: Mar. 29, 2018

(65) Prior Publication Data
US 2019/0275074 A1    Sep. 12, 2019

(30) Foreign Application Priority Data

Sep. 20, 2016 (DK) .......................... PA 2016 70733

(51) Int. Cl.
| | |
|---|---|
| *A61K 31/727* | (2006.01) |
| *A61P 3/06* | (2006.01) |
| *A61K 31/7028* | (2006.01) |
| *A61K 31/702* | (2006.01) |
| *A61K 31/704* | (2006.01) |
| *A61K 31/7056* | (2006.01) |
| *A61K 31/726* | (2006.01) |

(52) U.S. Cl.
CPC .......... *A61K 31/727* (2013.01); *A61K 31/702* (2013.01); *A61K 31/704* (2013.01); *A61K 31/7028* (2013.01); *A61K 31/7056* (2013.01); *A61K 31/726* (2013.01); *A61P 3/06* (2018.01)

(58) Field of Classification Search
CPC .............. A61K 31/702; A61K 31/7024; A61K 31/7028; A61K 31/727; A61K 47/28; A61K 47/554; A61P 3/04; A61P 3/06; A61P 9/00–14
See application file for complete search history.

(56) References Cited

U.S. PATENT DOCUMENTS

| | | | |
|---|---|---|---|
| 7,754,208 B2 | 7/2010 | Ledbetter et al. | |
| 8,828,952 B2 * | 9/2014 | Ferro ...................... | A61P 29/00 514/25 |
| 9,255,154 B2 | 2/2016 | Feldhaus et al. | |
| 2003/0133939 A1 | 7/2003 | Ledbetter et al. | |

FOREIGN PATENT DOCUMENTS

| | | |
|---|---|---|
| EP | 9404097 A2 | 12/1990 |
| EP | 2495242 A2 | 9/2012 |
| WO | 9307167 A1 | 4/1993 |
| WO | 9311161 A1 | 6/1993 |
| WO | 9409131 A1 | 4/1994 |
| WO | 9413806 A1 | 6/1994 |
| WO | 9243478 A2 | 6/2002 |
| WO | 2009049370 A1 | 4/2009 |
| WO | 2010029513 A2 | 3/2010 |
| WO | 2013091103 A1 | 6/2013 |
| WO | 2013148284 A1 | 10/2013 |
| WO | 2013177536 A2 | 11/2013 |
| WO | 2014005224 A1 | 1/2014 |
| WO | 2014150983 A2 | 9/2014 |
| WO | 2016150444 A1 | 9/2016 |

OTHER PUBLICATIONS

Nelson, R. "Hyperlipidemia as a risk factor . . . " Prim. Care, vol. 40, No. 1, pp. 195-211. (Year: 2013).*
Grundy, S. "An international atherosclerosis society position paper . . . " J. Clin. Lipidol., vol. 7, pp. 561-565. (Year: 2013).*
Hecht, et al; Journal of Clinical Oncology; vol. 27; No. 5; Feb. 10, 2009; pp. 672-680.
Benimetskaya et al.; Nucleic Acids Research, 1995, vol. 23, No. 21; pp. 4239-4245.
Biessen, et al.; Biochemical Journal; vol. 302, No. 1, Aug. 15, 1994; pp. 283-289.
Bird, et al; Science, vol. 242, No. 4877 (Oct. 21, 1988), pp. 423-426.
Casset, et al; Biochemical and Biophysical Research Communications; vol. 307, 2003, pp. 198-205.
Chan, et al; Proc. Natl. Acad. Sci. USA; vol. 106, No. 24; Jun. 16, 2009; pp. 9820-9825.
Cunningham, et al.; Nature Structural & Molecular Biology; vol. 14 No. 5; May 2007.
De la Paz, et al.; Pharmacologyonline 3: pp. 462-466 (2006).
Fisher, et al; Journal of Biological Chemistry; vol. 282; No. 28; Jul. 13, 2007.
Greenberg, et al; Nature; vol. 374; Mar. 9, 1995.
Guns, el al; British Journal of Pharmacology (2010): vol. 159: pp. 326-336.
Gustafsen, el al; Cell Metabolism 19, 310-318, Feb. 4, 2014.
Gustafsen, el al: Nature Communications; vol. 8. No. 1, Sep. 11, 2017.
Hamers-Casterman, et al; Letters to Nature; vol. 363; Jun. 3, 1993.
Herbert, et al; Circ Res 79: pp. 590-600 (1996).
Hollinger, et al.; Proc. Natl Acad. Sci. USA, vol. 90, pp. 6444-6448; Jul. 1993.
Horlacher. T. el al.; Biochemistry, Apr. 5, 2011, vol. 50, pp. 2650-2659.
Huston, et al.: Proc. Natl. Acad. Sci. USA, vol. 85, pp. 5879-5883, Aug. 1988; Biochemistry.

(Continued)

*Primary Examiner* — Leigh C Maier
(74) *Attorney, Agent, or Firm* — Dinsmore & Shohl LLP; Weston R. Gould

(57) ABSTRACT

The present disclosure relates to use of heparin analogues as inhibitors of proprotein convertase subtilisin-like/kexin type 9 (PCSK9) for the treatment of lipoprotein metabolism disorders.

12 Claims, 41 Drawing Sheets

Specification includes a Sequence Listing.

(56) References Cited

OTHER PUBLICATIONS

Jerabek-Willemsen, el al.; Assay and Drug Development Technologies. vol. 9, No. 4; Aug. 2011.
Kohler and Milstein; Nature, vol. 256, Aug. 7, 1975; pp. 495-497.
Lagace, etal.; The Journal of Clinical Investigation: vol. 116; No. 11, Nov. 2001.
Lakoski, et al.; J Clin Endocrinol Metab., 2009; vol. 94(7): pp. 2537-2543.
Lonberg, et al.; Nature, vol. 368; Apr. 28, 1994.
Mullard; Nature Reviews: Drug Discovery; vol. 14, (Sep. 2015) 593.
Munck Petersen, et al.; The EMBO Journal: vol. 18, No. 3; pp. 595-604, 1999.
Nonaka, et al.; Proc. Natl. Acad. Sci. USA; Jun. 3, 2014; vol. 111, No. 22; pp. 8173-8178.
Nour-Eldin, et al.; Nucleic Acids Research, 2006, vol. 34, No. 18.
Paul, William E., Fundamental Immunology, pp. 292-295 (William Paul Ed., Raven Press 1993).
Piper, et al.; Structure: vol. 15, pp. 545-552, May 2007.
Reiter, et al; The Journal of Biological Chemistry; vol. 269, No. 28, Issue of Jul. 15, pp. 18327-18331, 1994.
Seidah, et al; Review; Circ Res. 2014; vol. 114; 1022-1036.
Sheridan, C.; Nature Biotechnology; vol. 33, No. 8 Aug. 2015.
Stein, C.A.; Nature Medicine, vol. 1; No. 11, Nov. 1995; pp. 1119-1121.
Soderberg, et al.; Nature Methods; vol. 3; No. 12; Dec. 2006; pp. 995-10006.
Villiers, B.R. et al; Protein Engineering, Design & Selection; vol. 23 No. 1 pp. 1-8, 2010.
Walley, et al; Curr Opin Cril Care, 2016, 22:464-469; vol. 22, No. 5; Oct. 2016.
Ward et al; (1989) Nature; vol. 341; pp. 544-546.
Wozniak-Knopp, et al.; PLoS ONE; Jan. 2012 ; vol. 7. Issue 1; e30083.
Xu and Esko; (2014) Annu Rev Biochem.; 2014; vol. 83; pp. 129-157.
Yabukov et al. (1993) J Biol Chem.; vol. 268, No. 25; pp. 18818-18823.
Tyrrell DJ., et al.; Trends in Pharmacological Sciences, Elsevier, Haywarth, GB, vol. 16, No. 6, Jun. 1, 1995, pp. 198-204.
Lima et al., Structural and thermodynamic analysis of thrombin:suramin interaction in solution and crystal phases, Biochim Biophys Acta. Jun. 2009 ;1794(6)-873-81.
Mccoy, A.J., et al., Structure of beta-antithrombin and the effect of glycosylation on antithrombin's heparin affinity and activity. J Mol Biol, 2003. 326(3)—p. 823-33.

* cited by examiner

PCSK9 cholesterol

LDLR

HSPG

C

C

D

A

B LDLR in lysates

C PCSK9 in media

D

PBS        Heparin

A

B

D

E

I

J

A

B

Mouse liver LDLR 1 hour post injection

B

Heparin I

Heparin III

Heparin V

Heparin VII

Heparin IX

Heparin XII                          Heparin XIII

B (cont.)

A

B

C

D

A) Heparin sepharose binding assay

B) HepG2 cell assay

C) PCSK9 in vivo challenge experiment

A

B

A) Size-exclution chromatography elution profile of Innohep

A) PCSK9 binding to heparin-albumin

B) PCSK9 binding to albumin

A) Structure of sucrose octasulfate

B) Heparin sepharose binding assay

COMPOUNDS FOR TREATMENT OF LIPOPROTEIN METABOLISM DISORDERS

TECHNICAL FIELD

The present disclosure relates to use of heparin analogues as inhibitors of proprotein convertase subtilisin-like/kexin type 9 (PCSK9) for the treatment of lipoprotein metabolism disorders.

BACKGROUND

Coronary artery disease caused by atherosclerosis is the leading cause of death in Europe and the US. A major risk factor in the development of atherosclerosis is hypercholesterolemia with an elevated level of cholesterol-carrying low-density-lipoprotein (LDL cholesterol or LDL-C) particles in the circulation. The metabolism of LDL cholesterol particles is highly regulated to balance the synthesis of cholesterol with the dietary intake to serve the need for cholesterol in the body. A key regulator in the turnover of LDL cholesterol is the LDL receptor (LDLR) that mediates cellular uptake of LDL particles and decreases the level of LDL cholesterol in the circulation, as illustrated by patients with familial hypercholesterolemia caused by LDLR deficiency or functional impairment.

A successful strategy to reduce LDL cholesterol plasma levels is to increase the cellular levels of LDLR, and today the most widely used medication to lower LDL cholesterol is statins. Statins inhibit the synthesis of cholesterol and up-regulate the expression of LDLR, thus overall resulting in decreased amounts of circulating LDL cholesterol. However, a considerable number of patients do not respond to or tolerate statins due to various side effects. Furthermore, statins also increase the expression of proprotein convertase subtilisin-like/kexin type 9 (PCSK9) that was recently identified as a potent negative regulator of LDLR (Seidah et al., 2014), thereby counteracting the beneficial effect on the LDL cholesterol.

Targeting PCSK9 is a recent strategy for lowering plasma LDL-C (Lagace et al., 2006). The cellular level of the LDLR is reduced due to the ability of PCSK9 to bind the LDLR thereby impairing recycling and enhancing lysosomal degradation of the receptor. PCSK9 gain-of-function mutations lead to a significant increase in circulating LDL-C due to increased degradation of LDLR. In contrast, individuals with PCSK9 loss-of-function mutations show reduced levels of LDL-C and exhibit fewer incidents of coronary heart disease. Several leading pharmaceutical companies have obtained approval for therapeutic strategies targeting PCSK9 for the alleviation of hypercholesterolemia. Administration of PCSK9-specific antibodies directed against the LDLR-binding site of PCSK9 is reported to decrease LDL-C plasma levels in Phase III clinical trials (Mullard (2015) Nat Rev Drug Discov; Sheridan (2015) Nature Biotechnology). However, the PCSK9:LDLR binding constant is in the range of 120-620 nM (Cunningham et al., 2007; Fisher et al., 2007) while the PCSK9 plasma concentration is around 6 nM (Lakoski et al., 2009), rendering it highly unlikely that PCSK9 binds LDLR directly at physiologically relevant concentrations. In addition, PCSK9 only targets LDLR in the liver and not in e.g. steroid hormone producing tissues, which also express high levels of LDLR, suggesting the requirement of a liver-specific co-receptor (Seidah et al., 2014). Thus, LDLR is most likely not the primary PCSK9 receptor. Instead, an unknown receptor (receptor X) may capture circulating PCSK9 and subsequently deliver it to LDLR. Inhibition of PCSK9 binding to this receptor is therefore a superior strategy compared to inhibition of the PCSK9:LDLR interaction.

SUMMARY OF THE INVENTION

The present inventors have found that PCSK9 harbours a binding motif for heparan sulfate proteoglycans (HSPGs). Mutations introduced into this motif as well as inhibition of binding to HSPGs by heparin protect the LDLR against PCSK9-induced degradation. Inhibition of the interaction between PCSK9 and HSPGs has superior therapeutic potential as compared to the clinical trials of a PCSK9 inhibitory antibody (Chan et al., 2009). Importantly, the HSPG-binding motif in PCSK9 is different from that of the LDLR-binding surface. HSPGs consist of a core protein substituted with one or more heparan sulfate glycosaminoglycan chains. Heparin is a class of glycosaminoglycans which are closely related to heparan sulfate (HS) in structure. Heparin and HS are both composed of repeating disaccharide units consisting of uronic acid (glucuronic acid (GlcA) or iudoronic acid (IdoA)) and N-acetyl glucosamine (GlcN), which can be O- and/or N-sulfated. Heparin is a highly sulfated variant of heparan sulfate. HSPGs are highly glycosylated proteins, which bind protein ligands having HSPG-binding motifs, creating local depots of e.g. growth factors (Xu and Esko, 2014). The data show that PCSK9 binds HSPG, and that the interaction is abolished by site-directed mutagenesis of the HSPG-binding motif in PCSK9, resulting in a PCSK9 mutant unable to bind heparin and exhibiting impaired capacity to degrade the LDLR. In addition, incubation of cells with heparin or heparin analogues results in elevated levels of the LDLR, accompanied by increased concentration of PCSK9 in the media. Taken together, the results outlined in the present examples demonstrate that PCSK9 function is dependent on binding of HSPGs, and that the cellular level of LDLR is increased when the interaction between PCSK9 and HSPGs is abrogated.

Thus HSPGs are critical in PCSK9 mediated degradation of cell surface LDLR. The present findings show that HSPGs have a crucial function in PCSK9-induced down regulation of LDLR.

The site of interaction between PCSK9 and HSPGs can be targeted in blocking PCSK9 function, in particular in inhibiting the effect of PCSK9 on LDLR levels. Thus a new strategy in treatment of disorder of lipoprotein metabolism is disclosed.

In a first aspect, the invention relates to a composition comprising a compound having the general structure of formula (I):

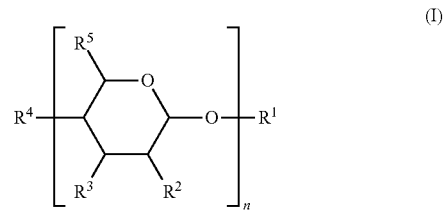

or a pharmaceutically acceptable salt, solvate, polymorph, or tautomer thereof, wherein:
  $R^1$ is selected from the group consisting of alkyl, substituted alkyl, heteroalkyl, substituted heteroalkyl, alkylsulfonyl, substituted alkylsulfonyl, alkenyl, substituted alkenyl, alkynyl, substituted alkynyl, alkoxy, substituted alkoxy, ester, amide, acyl, substituted acyl, amino, substituted amino, thioalkyl, substituted thioalkyl, aryl, heteroaryl, substituted aryl, hydrogen, and halogen;

each $R^2$ is independently selected from the group consisting of $-OSO_3^-$, $-OH$, $-NH_2$, $-NHSO_3^-$, $-NHOCH_3$ and $-OPO_3^{2-}$;

each $R^3$ is independently selected from the group consisting of $-OSO_3^-$, $-OH$ and $-OPO_3^{2-}$;

each $R^4$ is independently selected from the group consisting of $-OSO_3^-$, $-OH$, $-OPO_3^{2-}$ and $-H$;

each $R^5$ is independently selected from the group consisting of $-CH_2OSO_3^-$, $-CH_2OH$, $-COO^-$ and $-CH_2OPO_3^{2-}$;

n is an integer equal to, or greater than 1;

for use in the treatment of a disorder of lipoprotein metabolism in a subject.

In one aspect, the invention relates to a method of inhibiting degradation of LDLR, said method comprising administering a composition comprising a compound as defined herein.

In another aspect, the invention relates to a method for reducing plasma lipoprotein levels in a subject in need thereof, said method comprising the step of administering to said subject a compound or a pharmaceutical composition as defined herein. In one embodiment, the lipoprotein is LDL-C.

DEFINITIONS

Figure 1:
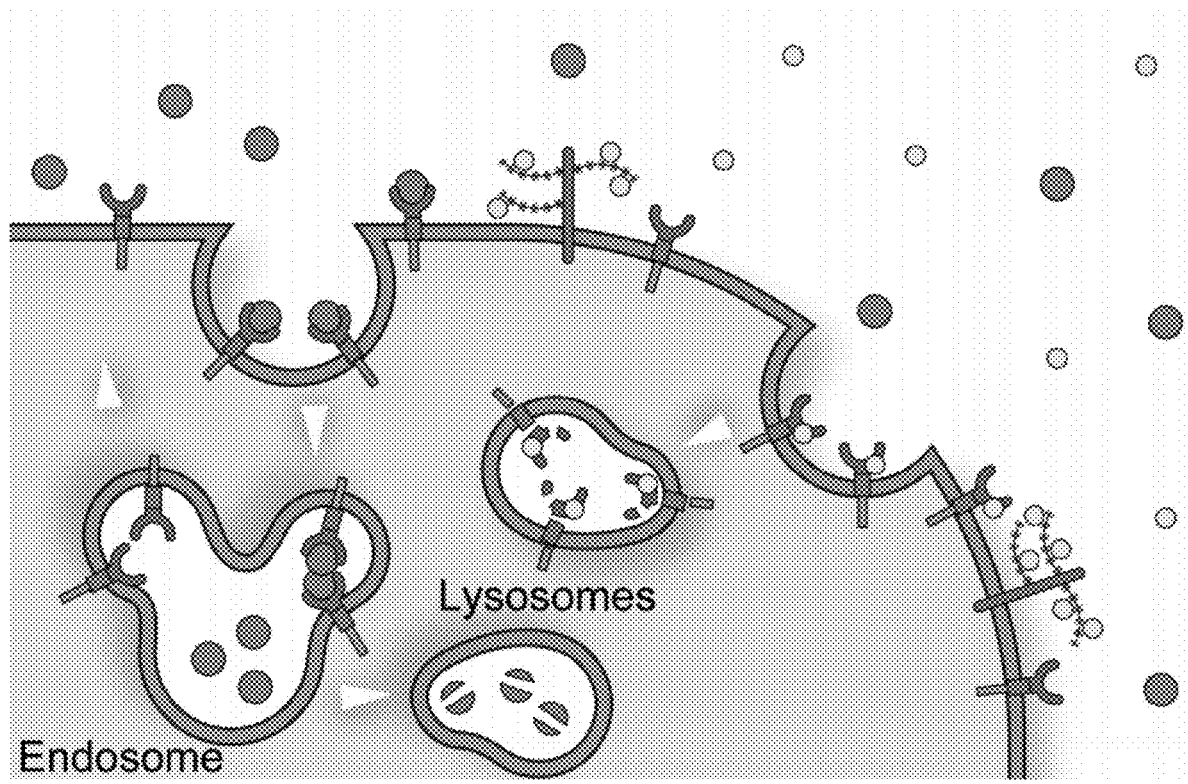
FIG. 1: A drawing of the proposed model depicting the capture of PCSK9 by HSPG and its subsequent presentation to LDLR at the hepatocyte surface. The LDLR takes up LDL-C particles from the circulation and delivers them to lysosomes for degradation, while the receptor (LDLR) is recycled to the cell surface after release of cargo in endosomes. Upon binding to PCSK9 the LDLR itself is degraded in lysosomes. HSPGs on the hepatocyte surface are proposed to capture PCSK9 and present it to LDLR, hereby ensuring optimal conditions for PCSK9:LDLR complex formation. Accordingly high activity of PCSK9 results in decreased levels of LDLR at the cell surface and increased plasma cholesterol, whereas inhibition of PCSK9 activity reduces plasma cholesterol levels and slows the progression of coronary artery disease.
Figure 1:
Figure 1:
Figure 1:
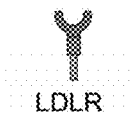
Figure 1:

The term "acyl", as used herein, means an alkyl group as defined below containing at least one oxo moiety (—C=O).

The term "alkane" refers to saturated linear, branched and/or cyclic carbonhydrides. Said alkanes may be of the general formula $C_nH_{2n+2}$. In some embodiments, said alkane comprises ring structures.

The term "alkenyl" as used herein refers to a substituent derived from an alkene by removal of one —H. An alkene may be any acyclic carbonhydride comprising at least one double bond. Frequently, alkenyl will have the general formula —$C_nH_{2n-1}$.

The term "alkyl" refers to a substituent derived from an alkane by removal of one —H.

The term "alkynyl" as used herein refers to a substituent derived from an alkyne by removal of one —H. An alkyne may be any acyclic carbonhydride comprising at least one triple bond. Frequently, alkynyl will have the general formula —$C_nH_{2n-3}$.

The term "alkylsulfonyl" refers to a —$S(O)_2$-alkyl group which may be a terminal group or a bridging group.

The term "amide" refers to the functional group RC(O) NR'R".

The term "amino" as used herein refers to a substituent of the general formula

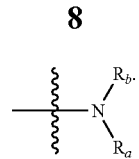

The waved line indicates the point of attachment of the substituent. Amino may thus for example be —$NH_2$ or —NH—.

The term "arene" as used herein refers to aromatic mono- or polycyclic carbonhydrides.

The term "aryl" as used herein refers to a substituent derived from an arene by removal of one —H from a C in the ring. Examples of useful aryls to be used with the present invention comprise phenyl, napthyl, anthracenyl, phenanthrenyl, and pyrenyl.

The term "ester" refers to the functional group RCOOR'.

The term "halogen" as used herein refers to a substituent selected from the group consisting of —F, —Cl, —Br and —I.

The term "heparin analogue" refers to compounds being structurally similar to heparin.

The term "heparin mimetic" refers to compounds behaving functionally like, i.e. mimicking, heparin. This term thus includes both compounds being structurally similar, but also compounds having different structure but same functionality as heparin, in the context of the present disclosure.

The term "heteroalkyl" as used herein refers to an alkyl group in which one or more carbons have been exchanged by a heteroatom selected from S, O, P, and N.

The term "heteroaryl" as used herein refers to a substituent derived from an heteroarene by removal of one —H from an atom in the ring structure of said heteroarene. Heteroarenes are mono- or polycyclic aromatic compounds comprising one or more heteroatoms in the ring structure. Said heteroatoms are preferably selected from the group consisting of S, N and O. Non limiting examples of useful heteroaryls to be used with the present invention comprise azolyl, pyridinyl, pyrimidinyl, furanyl, and thiophenyl.

LDL-cholesterol (LDL-C) levels: The optimal LDL-C levels for a given individual vary depending on his/her underlying risk of heart disease. For healthy individuals, LDL-C levels should ideally be less than 2.6-3.3 mmol/L (or 100-129 mg/dL). Levels between 3.4 and 4.1 mmol/L or 130 and 159 mg/dL are borderline high, levels between 4.1 and 4.9 mmol/L or 160 and 189 mg/dL are high, and levels above 4.9 mmol/L or 189 mg/dL are very high. For individuals at risk of heart disease, levels below 2.6 mmol/L or 100 mg/dL are recommended, while levels below 1.8 mmol/L or 70 mg/dL are desirable for individuals at very high risk of heart disease.

Low-density lipoprotein receptor (LDLR) levels: Synthesis of LDLR in the cell is regulated by the level of free intracellular cholesterol; if cholesterol is in excess for the needs of the cell then the transcription of LDLR will be inhibited. LDLR levels can be estimated by methods known in the art, such as, but not limited to, Western blotting, RT-PCR and flow cytometry.

The term "low-molecular weight heparin" refers to a class of heparins of limited size. Natural heparin consists of molecular chains of varying lengths, or molecular weights. For example, chains of varying molecular weights, from 5000 to over 40,000 Daltons, make up polydisperse pharmaceutical-grade heparin. Low-molecular weight heparins, in contrast, consist of only short chains of polysaccharide. Low-molecular weight heparins are defined as heparin salts having an average molecular weight of less than 8000 Da and for which at least 60% of all chains have a molecular weight less than 8000 Da. These are obtained by various methods known to the person skilled in the art, such as fractionation or depolymerisation of polymeric heparin.

The term "lipoprotein metabolism disorder" refers to disorders of lipid homeostasis and disorders associated therewith, including by way of example diabetes, obesity, metabolic syndrome, xanthoma, hypercholesterolemia, familial hypercholesterolemia, dyslipidemia, hypertriglyceridemia, hyperlipidemia, sitosterolemia, hypertension, angina, acute coronary syndrome, coronary heart disease, atherosclerosis, arteriosclerosis, vascular inflammation and sepsis.

PCSK9 levels: plasma levels of PCSK9 vary from 30 to 3000 ng/mL in the general population, and median levels are in general higher in women than in men. PCSK9 levels correlate with LDL-C levels.

The term "monosaccharide unit" as used herein refers to the most basic units of carbohydrates, and includes aldoses, ketoses and a wide variety of derivatives. If more than one monosaccharide unit is linked, the linkages may individually be α or β(1→2), α or β(1→3) or α or β(1→4). Preferably, the linkage is α or β(1→4). The monosaccharide unit may be an aldose or a ketose.

The term "substituted" as used herein in relation to chemical compounds refers to hydrogen group(s) being substituted with another moiety. Thus, "substituted with X" as used herein in relation to chemical compounds refers to hydrogen group(s) being substituted with X. Similarly, "substituted X" refers to X, wherein one hydrogen group has been substituted with another moiety. By way of example "substituted alkyl" refers to alkyl-R, wherein R is any moiety but —H.

The term "substituent" as used herein in relation to chemical compounds refers to an atom or group of atoms substituted in place of a hydrogen atom.

The term "thioalkyl" as used herein refers to a substituent of the general formula —S— alkyl.

The term "thioaryl" as used herein refers to a substituent of the general formula —S-aryl.

DETAILED DESCRIPTION OF THE INVENTION

The invention is as defined in the claims.

Heparin Analogues

The present invention relates in a first aspect to a composition comprising a compound for use in the treatment of a disorder of lipoprotein metabolism in a subject. The compound is typically a heparin analogue. Examples of heparin analogues are described in R. Lever et al. (eds.), Heparin—A Century of Progress, Handbook of Experimental Pharmacology 207, Springer-Verlag Berlin Heidelberg 2012, herein incorporated by reference.

In one aspect the heparin analogue of the present invention has the general structure of formula (I):

$$\left[ R^4 \underset{R^3}{\overset{R^5}{\underset{\phantom{R^3}}{\bigcirc}}} \underset{R^2}{\overset{O}{\phantom{\bigcirc}}} O \right]_n R^1 \quad (I)$$

or a pharmaceutically acceptable salt, solvate, polymorph, or tautomer thereof, wherein:

$R^1$ is selected from the group consisting of alkyl, substituted alkyl, heteroalkyl, substituted heteroalkyl, alkylsulfonyl, substituted alkylsulfonyl, alkenyl, substituted alkenyl, alkynyl, substituted alkynyl, alkoxy, substituted alkoxy, ester, amide, acyl, substituted acyl, amino, substituted amino, thioalkyl, substituted thioalkyl, aryl, heteroaryl, substituted aryl, hydrogen, and halogen;

each $R^2$ is independently selected from the group consisting of —OSO$_3^-$, —OH, —NH$_2$, —NHSO$_3^-$, —NHOCH$_3$ and —OPO$_3^{2-}$;

each $R^3$ is independently selected from the group consisting of —OSO$_3^-$, —OH and —OPO$_3^{2-}$;

each $R^4$ is independently selected from the group consisting of —OSO$_3^-$, —OH, —OPO$_3^{2-}$ and —H;

each $R^5$ is independently selected from the group consisting of —CH$_2$OSO$_3^-$, —CH$_2$OH, —COO$^-$ and —CH$_2$OPO$_3^{2-}$;

n is an integer equal to, or greater than 1;

for use in the treatment of a disorder of lipoprotein metabolism in a subject.

In one embodiment, n is 1, 2, 3 or 4.

In some embodiments, $R^1$ in the compound of formula (I) comprises a group of formula (II):

$$\text{\textsection}\!\!-\!\!(\ )_m\!\!-\!\!X\!\!-\!\!\sim\!\!NH_2 \quad (II)$$

wherein:

X is CH$_2$ or SO$_2$ m is an integer independently equal to, or greater than 1.

In one embodiment, m is 1, 2, 3, 4, 5 or 6. In one embodiment, $R^1$ comprises a group of formula (XI).

(XI)

In some embodiments, $R^1$ is a substituted heteroalkyl. Said substituted heteroalkyl may comprise monosaccharide unit(s). In some embodiments, $R^1$ comprises at least one monosaccharide unit, such as at least two monosaccharide units, such as at least three monosaccharide units, such as at least four monosaccharide units. In a preferred embodiment, n in formula (I) is 1 when $R^1$ comprises at least one monosaccharide unit.

In one embodiment, $R^1$ further comprises a moiety selected from the group consisting of alkyl, substituted alkyl, heteroalkyl, substituted heteroalkyl, alkylsulfonyl, substituted alkylsulfonyl, alkenyl, substituted alkenyl, alkynyl, substituted alkynyl, alkoxy, substituted alkoxy, ester, amide, acyl, substituted acyl, amino, substituted amino, thioalkyl, substituted thioalkyl, aryl, heteroaryl, substituted aryl, hydrogen, and halogen.

In one embodiment, $R^1$ comprises a group selected from the group consisting of formula (XVI), formula (XVII), formula (XVIII), formula (XIX), formula (XX), formula (XXIX), formula (XXX), formula (XXXI), -PEG2000-OMe, and -PEG5000-OMe:

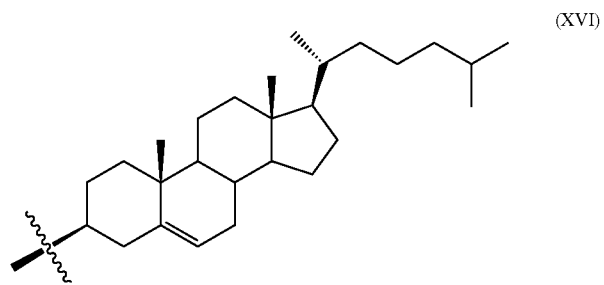
(XVI)

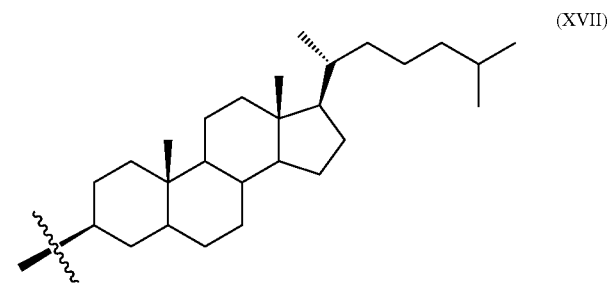
(XVII)

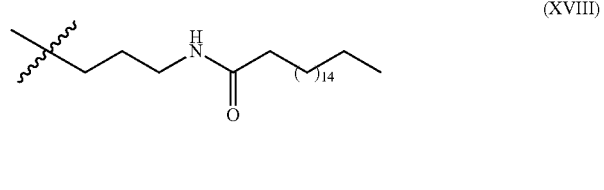
(XVIII)

(XXIX)

(XX)

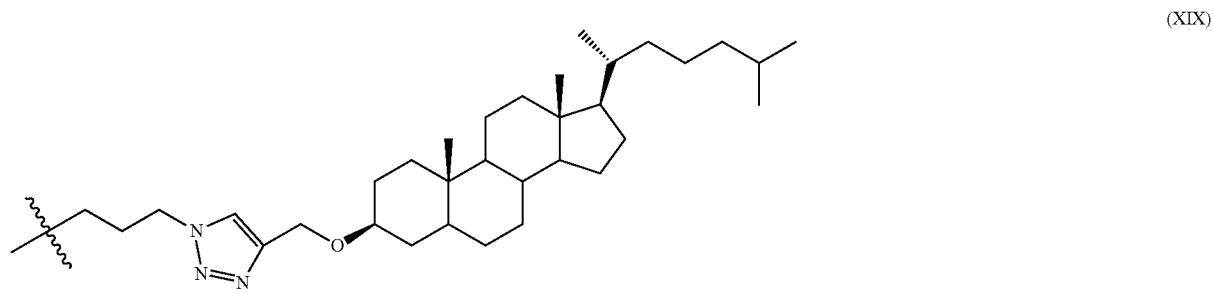
(XIX)

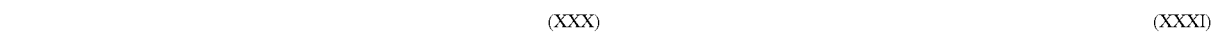
(XXX)

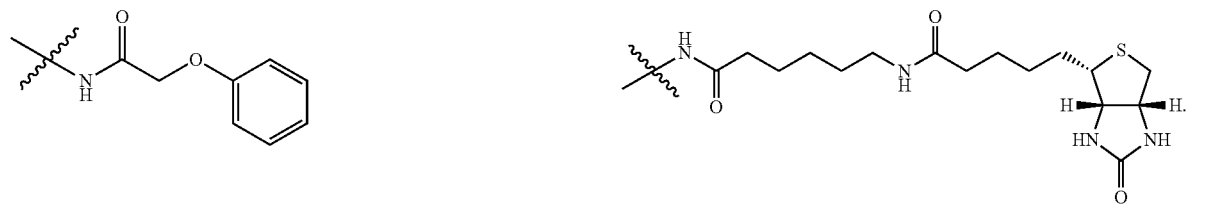
(XXXI)

In another embodiment, $R^1$ consists of a group selected from the group consisting of formula (XVI), formula (XVII), formula (XVIII), formula (XIX), formula (XX), formula (XXIX), formula (XXX), formula (XXXI), -PEG2000-OMe, and -PEG5000-OMe.

In some embodiments, the compound is a heparin mimetic. Said heparin mimetic may be a PI-88 based derivative. PI-88 (formula (XXIII), wherein $R^8$ is $-PO_3^{2-}$, and $R^9$ is individually $-SO_3^-$ or $-H$, see below) is a mixture of highly sulfated, monophosphorylated mannose oligosaccharides, and it is known to be a heparanase inhibitor.

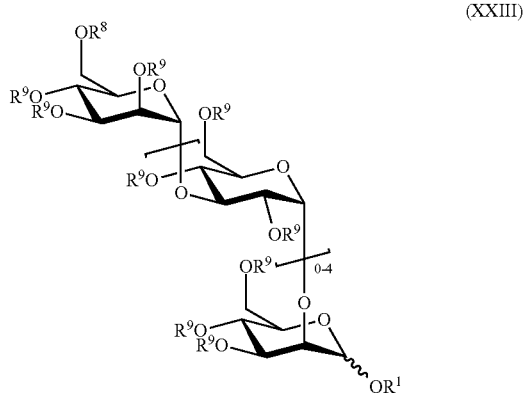

(XXIII)

Thus, in some embodiments, n in formula (I) is 1 and $R^1$ comprises a group of formula (XV), wherein s is an integer, equal to or greater than 1. In one embodiment, s is 1, 2 or 3.

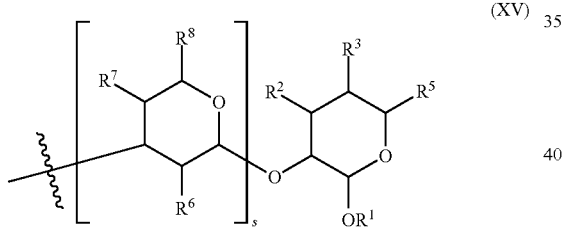

(XV)

In one embodiment, the compound of formula (I) is a compound of formula (XXIV), wherein p is an integer, equal to or greater than 1.

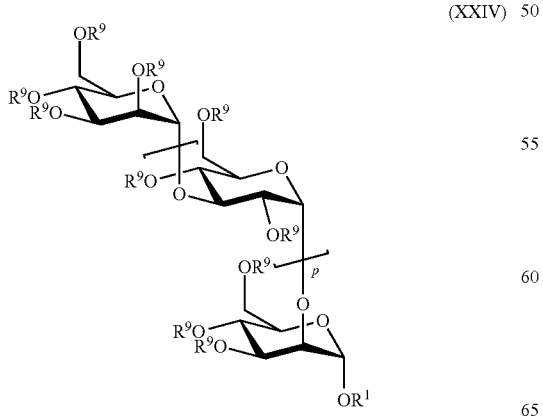

(XXIV)

In a preferred embodiment, wherein the compound is:

A. A compound of formula (XXIV) wherein p is 2 and $R^1$ is formula (XX);
B. A compound of formula (XXIV) wherein p is 2 and $R^1$ is formula (XVII);
C. A compound of formula (XXIV) wherein p is 2 and $R^1$ is formula (XVIII);
D. A compound of formula (XXIV) wherein p is 3 and $R^1$ is formula (XVII);
E. A compound of formula (XXIV) wherein p is 0 and $R^1$ is formula (XVII);
F. A compound of formula (XXIV) wherein p is 1 and $R^1$ is formula (XVII);
G. A compound of formula (XXIV) wherein p is 1 and $R^1$ is formula (XIX);
H. A compound of formula (XXIV) wherein p is 3 and $R^1$ is formula (XX); or
I. A compound of formula (XXIV) wherein p is 3 and $R^1$ is formula (XXIX).

In one embodiment, p is 1 and the compound of formula (I) is a compound of formula (XXV).

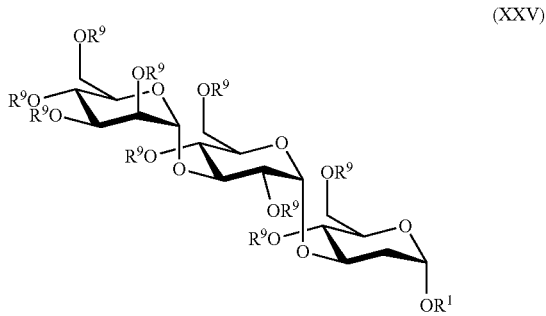

(XXV)

In a preferred embodiment, the compound is

J. A compound of formula (XXV) wherein $R^1$ is formula (XVII); or
K. A compound of formula (XXV) wherein $R^1$ is formula (XIX).

In one embodiment, the compound of formula (I) has the structure (IX).

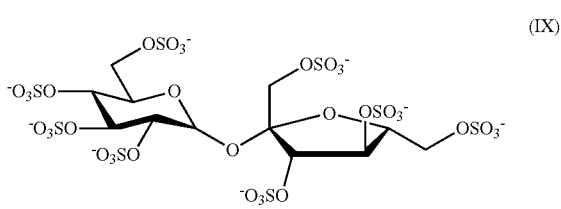

(IX)

In one embodiment, the compound of formula (I) is a compound of formula (XXVI), wherein q is an integer, equal to or greater than 1. In one embodiment, q is 1, 2 or 3.

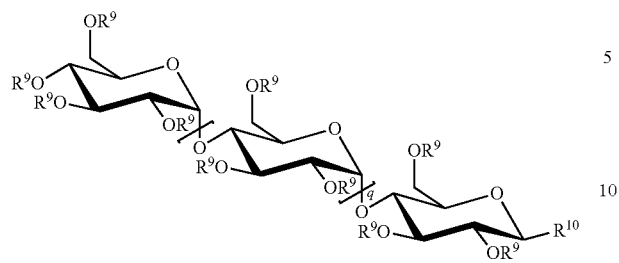

(XXVI)

In one embodiment, $R^{10}$ is —O—$R^1$. In another embodiment, $R^{10}$ comprises a group selected from the group consisting of formula (XXI), formula (XXII), —O-formula (XVI), —O-formula (XVII), —O-formula (XVIII), —O-formula (XIX) and —O-formula (XX). In another embodiment, $R^{10}$ consists of a group selected from the group consisting of formula (XXI), formula (XXII), —O-formula (XVI), —O-formula (XVII), —O-formula (XVIII), —O—formula (XIX), —O-formula (XX) and —O-formula (XXIX).

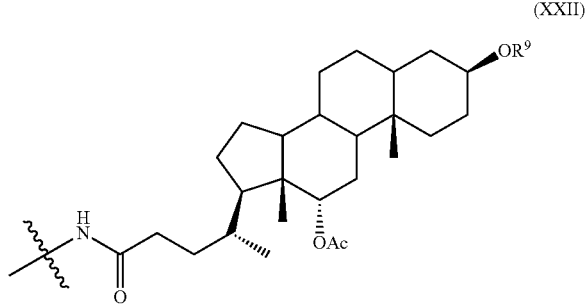

(XXII)

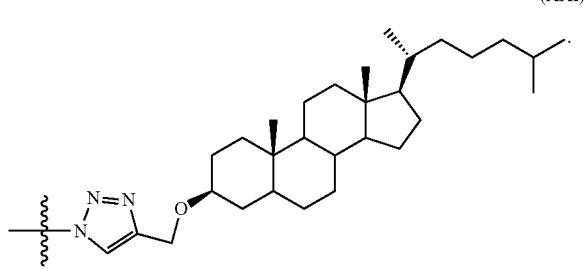

(XXI)

In a preferred embodiment, the compound is
L. A compound of formula (XXVI), wherein q is 2 and $R^{10}$ is —O-formula (XVII);
M. A compound of formula (XXVI), wherein q is 2 and $R^{10}$ is formula (XXI);
N. A compound of formula (XXVI), wherein q is 1 and $R^{10}$ is formula (XVII);
O. A compound of formula (XXVI), wherein q is 2 and $R^{10}$ is —O-formula (XXII);
P. A compound of formula (XXVI), wherein q is 1 and $R^{10}$ is —O-formula (XVII);
Q. A compound of formula (XXVI), wherein q is 2 and $R^{10}$ is —O-formula (XVIII);
R. A compound of formula (XXVI), wherein q is 1 and $R^{10}$ is —O-formula (XVIII);
S. A compound of formula (XXVI), wherein q is 0 and $R^{10}$ is —O-formula (XVII); or T. A compound of formula (XXVI), wherein q is 0 and $R^{10}$ is —O-formula (XXI).

In one embodiment, the compound of formula (I) is a compound of formula (XXVII).

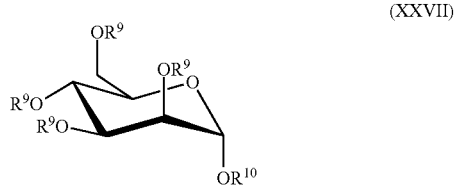

(XXVII)

In a preferred embodiment, the compound is of formula (XXVII) and $R^{10}$ is formula (XVII).

In one embodiment, the compound of formula (I) is a compound of formula (XXVIII).

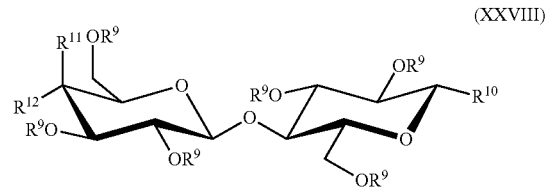

(XXVIII)

In a preferred embodiment, the compound is
U. A compound of formula (XXVIII), wherein $R^{10}$ is —O-formula (XVII), $R^{11}$ is H, and $R^{12}$ is $OR^9$; or
V. A compound of formula (XXVIII), wherein $R^{10}$ is formula (XXI), $R^{11}$ is $OR^9$, and $R^{12}$ is H.

In one embodiment, the compound has the general structural formula (XII).

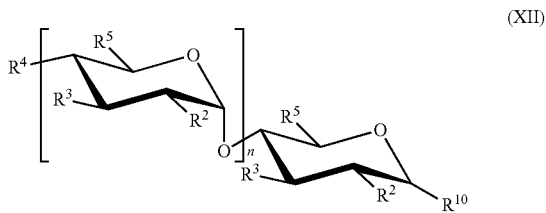

(XII)

In one embodiment, $R^2$ is —$OSO_3^-$. In another embodiment, $R^3$ is —$OSO_3^-$. In another embodiment, $R^4$ is —$OSO_3^-$. In another embodiment, $R^5$ is —$CH_2OSO_3^-$. In a preferred embodiment, $R^2$, $R^3$ and $R^4$ are —$OSO_3^-$ and $R^5$ is —$CH_2OSO_3^-$. In one embodiment, $R^9$ is —$OSO_3^-$.

In one embodiment, the pharmaceutically acceptable salt is the sodium salt.

In one embodiment, the compound has the general structural formula (XIII).

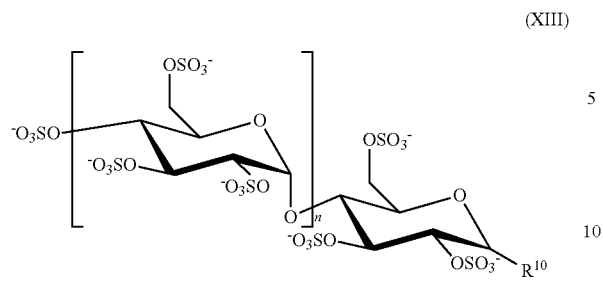
(XIII)

In a preferred embodiment, n is 2, 3 or 4.

In one embodiment, the compound has the general structural formula (XIV).

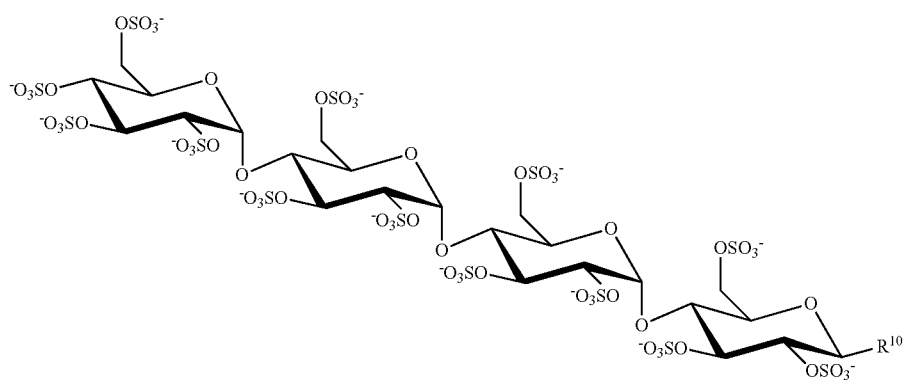
(XIV)

In a preferred embodiment, the compound of formula (I) is compound (X):

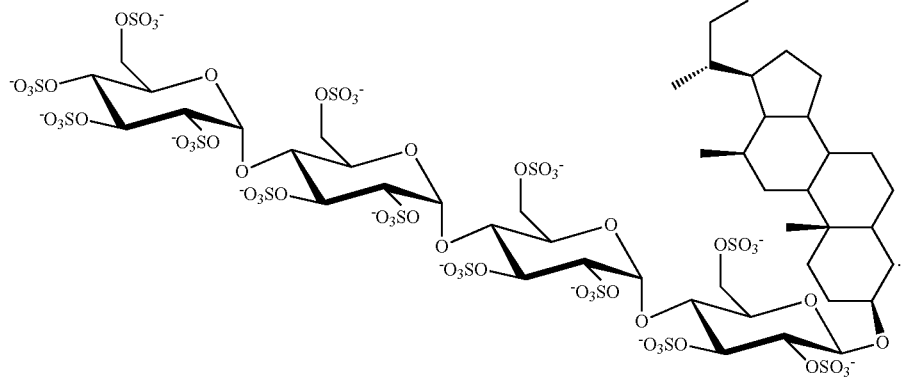
(X)

In a preferred embodiment, the compound of formula (I) is 3β-cholestanyl 2,3,4,6-tetra-O-sulfo-α-D-glucopyranosyl-(1→4)-2,3,6-tri-O-sulfo-α-D-glucopyranosyl-(1→4)-2,3,6-tri-O-sulfo-α-Dglucopyranosyl-(1→4)-2,3,6-tri-O-sulfo-β-D-glucopyranoside tridecasodium salt In one embodiment, the compound of formula (I) has the general structure (III):

(III)

wherein:

$R^1$ is selected from the group consisting of alkyl, substituted alkyl, heteroalkyl, substituted heteroalkyl, alkylsulfonyl, substituted alkylsulfonyl, alkenyl, substituted alkenyl, alkynyl, substituted alkynyl, alkoxy, substituted alkoxy, ester, amide, acyl, substituted acyl, amino, substituted amino, thioalkyl, substituted thioalkyl, aryl, heteroaryl, substituted aryl, hydrogen, and halogen;

each $R^2$ and $R^6$ is independently selected from the group consisting of —$OSO_3^-$, —OH, —$NH_2$, —$NHSO_3^-$, —$NHOCH_3$ and —$OPO_3^{2-}$;

each $R^3$ and $R^7$ is independently selected from the group consisting of —$OSO_3^-$, —OH and —$OPO_3^{2-}$;

each $R^5$ and $R^8$ is independently selected from the group consisting of —$CH_2OSO_3^-$, —$CH_2OH$, —$COO^-$ and —$CH_2OPO_3^{2-}$;

each $R^4$ is independently selected from the group consisting of —$OSO_3^-$, —OH, —$OPO_3^{2-}$ and —H;

n is an integer equal to, or greater than 1.

In one embodiment, the compound of formula (I) has the general structure (IV):

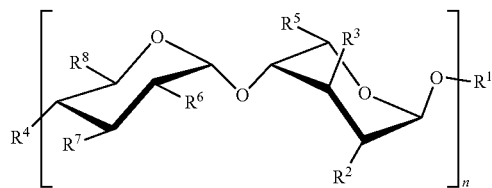

(IV)

In one embodiment, the compound of formula (I) has the general structure (V):

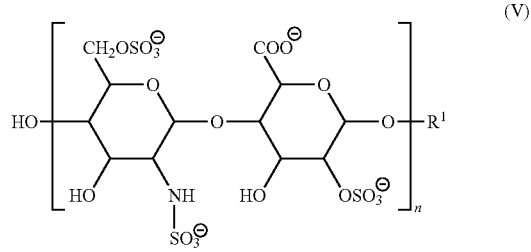

(V)

In one embodiment, the compound of formula (I) has the general structure (VI):

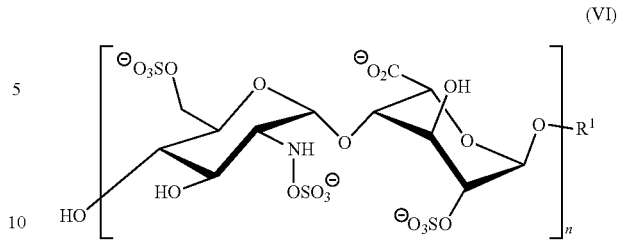

(VI)

Heparin and heparan sulfate consist of repeating disaccharide units. In one embodiment, the number of repetitive units in the compounds of formulas (III)-(VI) is 1. In another embodiment, the number of repetitive units in the compounds of formulas (III)-(VI) is 2. In another embodiment, the number of repetitive units in the compounds of formulas (III)-(VI) is 3. In another embodiment, the number of repetitive units in the compounds of formulas (III)-(VI) is 4. In another embodiment, the number of repetitive units in the compounds of formulas (III)-(VI) is 5. In another embodiment, the number of repetitive units in the compounds of formulas (III)-(VI) is 6. In another embodiment, the number of repetitive units in the compounds of formulas (III)-(VI) is 7. In another embodiment, the number of repetitive units in the compounds of formulas (III)-(VI) is 8. In another embodiment, the number of repetitive units in the compounds of formulas (III)-(VI) is 9. In another embodiment, the number of repetitive units in the compounds of formulas (III)-(VI) is 10.

In one embodiment, the compound of formula (I) has the general structure (VII):

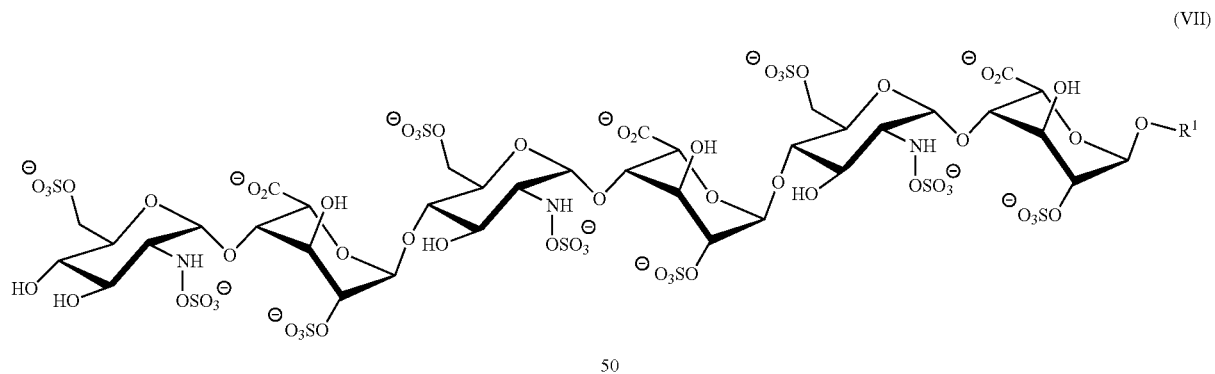

(VII)

In one embodiment, the compound has the general structure (VIII):

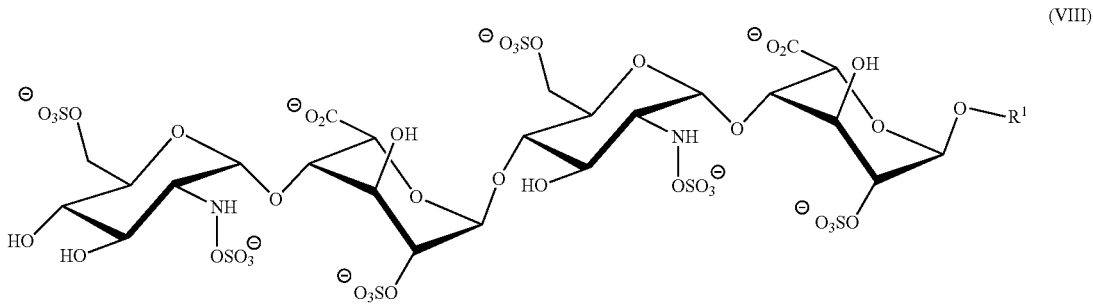

(VIII)

In a specific embodiment, the compound of formula (I) is Heparin I and has the following structure:

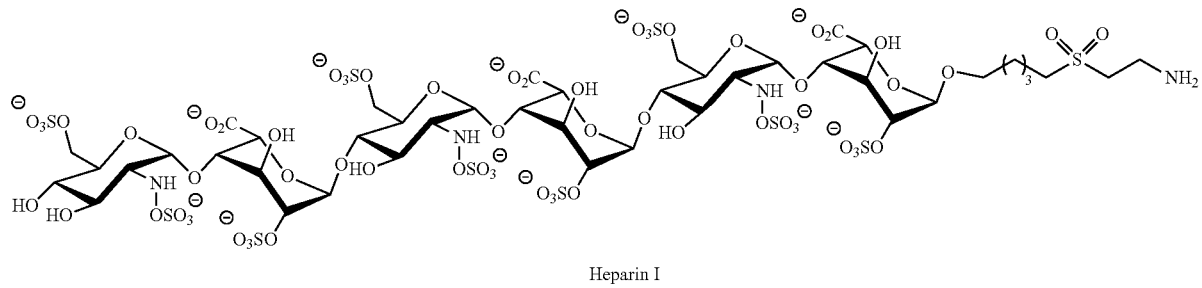

Heparin I

In a specific embodiment, the compound of formula (I) is Heparin VII and has the following structure:

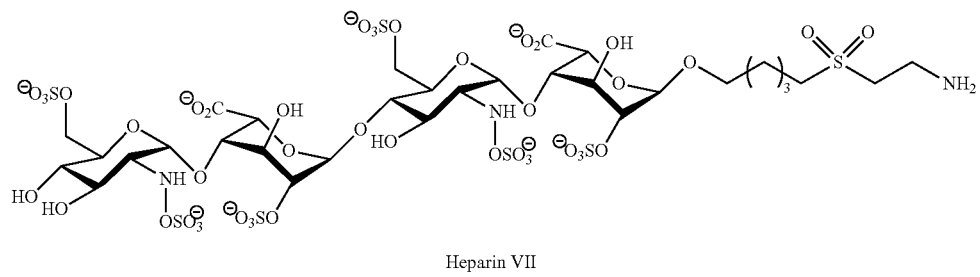

Heparin VII

In some embodiments, the compound further comprises an albumin binding moiety conjugated to said compound. In one embodiment, the albumin binding moiety is a fatty acid, which can be selected from the group consisting of caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid.

In some embodiments, bile acid is conjugated to the compound of formula (I). In one embodiment, the conjugated bile acid is selected from the group consisting of cholic acid, taurocholic acid, glycocholic acid, taurochenodeoxycholic acid, glycochenodeoxycholic acid, chenodeoxycholic acid, deoxycholic acid, and lithocholic acid.

In one embodiment, the compound of formula (I) is covalently attached via the terminal amino group (as R) to a dendritic structure of the formula:

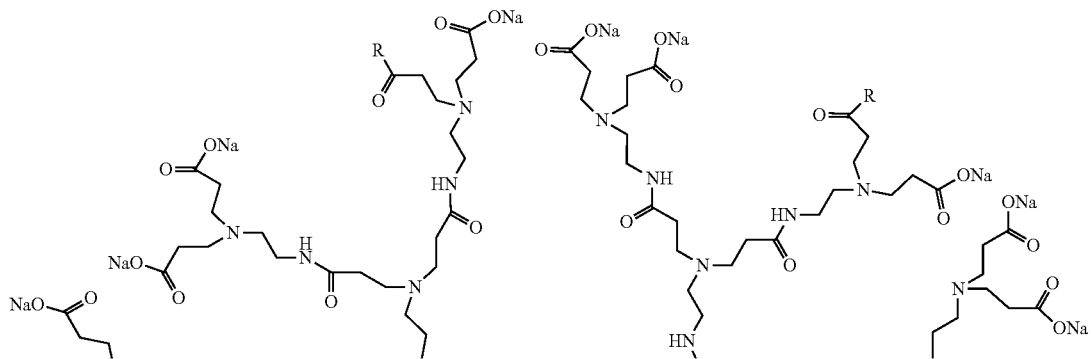

-continued

[chemical structures]

Binding of Heparin Analogues to PCSK9

In some embodiments, the heparin analogue is capable of inhibiting binding of HSPG to PCSK9. In some embodiments, the heparin analogue bind to any of the amino acid residues of PCSK9 as described herein below. It will be understood throughout this disclosure that compounds capable of inhibiting binding of HSPGs to variants of PCSK9 is also within the scope of the invention. By variant of PCSK9 is understood a polypeptide which has essentially the same sequence as SEQ ID NO: 1, for example variants having conservative substitutions of some residues of SEQ ID NO: 1.

In some embodiments, said compound specifically recognizes and binds a region within the HSPG binding site of PCSK9 (SEQ ID NO: 1) that comprises at least one of amino acid residues 78 to 167 of PCSK9 (SEQ ID NO: 1), such as at least one of amino acid residues 78 to 92, such as at least one of amino acid residues 93 to 97, such as at least one of amino acid residues 98 to 103, such as at least one of amino acid residues 104 to 105, such as at least one of amino acid residues 106 to 135, such as at least one of amino acid residues 136 to 139, such as at least one of amino acid residues 140 to 164, such as at least one of amino acid residues 165 to 167 of PCSK9 (SEQ ID NO: 1).

Herein is provided a compound that specifically recognizes and binds a region within the HSPG binding site of PCSK9 (SEQ ID NO: 1) that comprises at least one of amino acid residues 78 to 167 of PCSK9 (SEQ ID NO: 1), such as at least 2, such as at least 5, such as at least 10, such as at least 15, such as at least 20, such as at least 25, such as at least 30, such as at least 35, such as at least 40, such as at least 45, such as at least 50, such as at least 55, such as at least 60, such as at least 65, such as at least 70, such as at least 75, such as at least 80, such as at least 85, such as all of amino acid residues 78 to 167 of PCSK9 (SEQ ID NO: 1).

In some embodiments, the compound specifically recognizes and binds a region comprising at least one of amino acid residues 78 to 92, such as at least one of amino acid residues 93 to 97, such as at least one of amino acid residues 98 to 103, such as at least one of amino acid residues 104 to 105, such as at least one of amino acid residues 106 to 135, such as at least one of amino acid residues 136 to 139, such as at least one of amino acid residues 140 to 164, such as at least one of amino acid residues 165 to 167 of PCSK9 (SEQ ID NO: 1).

In some embodiments, the compound specifically recognizes and binds a region comprising at least one of amino acid residues 78 to 92, such as amino acid residues 93 to 97, such as amino acid residues 98 to 103, such as amino acid residues 104 to 105, such as amino acid residues 106 to 135, such as amino acid residues 136 to 139, such as amino acid residues 140 to 164, such as amino acid residues 165 to 167 of PCSK9 (SEQ ID NO: 1).

Thus in one embodiment, the compound specifically recognizes and binds a region within the HSPG binding site of PCSK9 comprising amino acid residues 78 to 167. In another embodiment, the compound specifically recognizes and binds a region within the HSPG binding site of PCSK9 comprising amino acid residues 78 to 95. In another embodiment, the compound specifically recognizes and binds a region within the HSPG binding site of PCSK9 comprising amino acid residues 96 to 100. In another embodiment, the compound specifically recognizes and binds a region within the HSPG binding site of PCSK9 comprising amino acid residues 101 to 105. In another embodiment, the compound specifically recognizes and binds a region within the HSPG binding site of PCSK9 comprising amino acid residues 106 to 110. In another embodiment, the compound specifically recognizes and binds a region within the HSPG binding site of PCSK9 comprising amino acid residues 111 to 115. In another embodiment, the compound specifically recognizes and binds a region within the HSPG binding site of PCSK9 comprising amino acid residues 116 to 120. In another embodiment, the compound specifically recognizes and binds a region within the HSPG binding site of PCSK9 comprising amino acid residues 121 to 125. In another embodiment, the compound specifically recognizes and binds a region within the HSPG binding site of PCSK9 comprising amino acid residues 126 to 130. In another embodiment, the compound specifically recognizes and binds a region within the HSPG binding site of PCSK9 comprising amino acid residues 131 to 135. In another embodiment, the compound specifically recognizes and binds a region within the HSPG binding site of PCSK9 comprising amino acid residues 136 to 140. In another embodiment, the compound specifically recognizes and binds a region within the HSPG binding site of PCSK9 comprising amino acid residues 141 to 145. In another embodiment, the compound specifically recognizes and binds a region within the HSPG binding site of PCSK9 comprising amino acid residues 146 to 150. In another embodiment, the compound specifically recognizes and binds a region within the HSPG binding site of PCSK9 comprising amino acid residues 151 to 155. In another embodiment, the compound specifically recognizes and binds a region within the HSPG binding site of PCSK9 comprising amino acid residues 156 to 160. In another embodiment, the compound specifically recognizes and binds a region within the HSPG binding site of PCSK9 comprising amino acid residues 161 to 167.

Thus there is provided a compound which binds to one or more amino acids selected from the group consisting of R93, R96, R97, R104, R105, K136, H139, R165 and R167 of PCSK9 (SEQ ID NO: 1), such as one amino acid, such as two amino acids, such as three amino acids, such as four amino acids, such as five amino acids, such as six amino acids, such as seven amino acids, such as eight amino acids, such as all of the amino acids selected from the group consisting of R93, R96, R97, R104, R105, K136, H139, R165 and R167 of PCSK9.

Thus in one embodiment, the compound binds to R93 of PCSK9. In another embodiment, the compound binds to R96 of PCSK9. In another embodiment, the compound binds to R97 of PCSK9. In another embodiment, the compound binds to R104 of PCSK9. In another embodiment, the compound binds to R105 of PCSK9. In another embodiment, the compound binds to K136 of PCSK9. In another embodiment, the compound binds to H139 of PCSK9. In another embodiment, the compound binds to R165 of PCSK9. In another embodiment, the compound binds to R167 of PCSK9.

In one embodiment, the compound binds to R96 and to R97 of PCSK9. In another embodiment, the compound binds to R104 and R105 of PCSK9. In another embodiment, the compound binds to K136 and H139 of PCSK9. In another embodiment, the compound binds to R93 and H139 of PCSK9. In another embodiment, the compound binds to R93, R104, R105 and H139 of PCSK9. In another embodiment, the compound binds to R165 and R167 of PCSK9. In another embodiment, the compound binds to R93, R96, R97, R104, R105 and H139 of PCSK9.

LDLR and LDL-C Levels

Binding of the compound disclosed herein to PCSK9 results in reduced binding of PCSK9 to LDLR compared to the binding in the absence of said compound. This in turn results in increased levels of LDLR of cells derived from an LDLR-expressing cell line such as a hepatocyte-derived cell line, for example on their surface, compared to the levels in the absence of said compound.

In some embodiments, the compound is a heparin analogue as defined above and its binding to PCSK9 results in reduced binding of PCSK9 to LDLR compared to the binding in the absence of said heparin analogue. This in turn results in increased levels of LDLR of cells derived from an LDLR-expressing cell line such as a hepatocyte-derived cell line compared to the levels in the absence of said heparin analogue.

In some embodiments, binding of the compound to PCSK9 results in decreased lysosomal degradation of LDLR compared to the degradation in the absence of said compound. In specific embodiments, the compound is a heparin analogue as defined above and binding of the heparin analogue to PCSK9 results in decreased lysosomal degradation of LDLR compared to the degradation in the absence of said heparin analogue.

In some embodiments, binding of the compound to PCSK9 results in decreased plasma levels of LDL-C compared to the levels in the absence of said compound. The term 'plasma LDL-C levels' shall be understood to refer to the levels of LDL-C in the plasma, i.e. the amount of LDL-C protein. In specific embodiments, the compound is a heparin analogue as defined above and binding of the heparin analogue to PCSK9 results in decreased plasma levels of LDL-C compared to the levels in the absence of said heparin analogue.

The plasma levels of LDL-C can be determined in vivo or in vitro. Methods to determine plasma levels of LDL-C are known in the art and include, but are not limited to Western Blot, immuno-staining, ELISA, ultracentrifugation, fast protein liquid chromatography (FPLC) and enzymatic calorimetric determination.

Disorders of Lipoprotein Metabolism

Herein is provided a composition comprising a compound for the use in treatment of a disorder of lipoprotein metabolism. Accordingly is also provided herein a use of the compound as defined herein for the preparation of a medicament for the treatment of a disorder of lipoprotein metabolism. There is also disclosed the compound as defined above for use in a method of treatment of a disorder of lipoprotein metabolism in a subject in need thereof. The sequence of PCSK9 may vary from one subject to another, e.g. individual-specific SNPs that may lead to conservative substitutions may be found in some individuals. It will be understood that compounds inhibiting binding of HSPGs to such PCSK9 variants are also within the scope of the invention.

In some embodiments, the disorder of lipoprotein metabolism is linked to abnormal PCSK9 plasma levels. In other embodiments, the disorder of lipoprotein metabolism is linked to abnormal LDLR levels at the surface of LDLR-expressing cells such as hepatocytes. The disorder of lipoprotein metabolism can also be linked to abnormal PCSK9 plasma levels and abnormal LDLR levels at the surface of LDLR-expressing cells such as hepatocytes. PCSK9 plasma levels vary in humans from 30 to 3000 ng/ml. Abnormal PCSK9 plasma levels refer to plasma levels of PCSK9 which are significantly different from the average levels in a healthy individual. In some embodiments, the abnormal PCSK9 plasma level is significantly higher than the average level in a healthy individual. Likewise, abnormal LDLR levels at the surface of e.g. hepatocytes refer to LDLR levels which are significantly different from the average levels in a healthy individual. In some embodiments, the abnormal LDLR level at the surface of LDLR-expressing cells such as hepatocytes is significantly lower than the average level in a healthy individual.

In some embodiments, the disorder is characterized by abnormal levels of LDL-C, in particular by elevated levels of LDL-C.

Disorders of lipoprotein metabolism are disorders of lipid homeostasis and disorders associated therewith and include by way of example hypercholesterolemia, familial hypercholesterolemia, dyslipidemia, hyperlipidemia, hypertriglyceridaemia, sitosterolemia, atherosclerosis, arteriosclerosis, coronary heart disease, metabolic syndrome, acute coronary syndrome, xanthoma, hypertension, angina, obesity, diabetes, vascular inflammation and sepsis. Such disorders can be caused for example by defects in the structural proteins of lipoprotein particles, in the cell receptors that recognize the various types of lipoproteins, or in the enzymes that break down fats. As a result of such defects, lipids may become deposited in the walls of blood vessels.

Hypercholesterolemia (or dyslipidemia) is the presence of high levels of cholesterol in the blood. It is a form of hyperlipidemia (elevated levels of lipids in the blood) and hyperlipoproteinemia (elevated levels of lipoproteins in the blood). Mixed dyslipidemia is elevations in LDL cholesterol and triglyceride levels that are often accompanied by low levels of HDL cholesterol. Familial hypercholesterolemia is a genetic disorder caused by mutations in the LDLR gene, and is characterized by high cholesterol levels, especially LDL cholesterol, in the blood.

Hypertriglyceridemia denotes high blood levels of triglycerides. Elevated levels of triglycerides are associated with atherosclerosis, even in the absence of hypercholesterolemia, and predispose to cardiovascular disease. Very high triglyceride levels also increase the risk of acute pancreatitis.

Sitosterolemia or phytosterolemia is a rare autosomal recessively inherited lipid metabolic disorder characterized by hyperabsorption and decreased biliary excretion of dietary sterols leading to e.g. hypercholesterolemia, tendon and tuberous xanthomas, premature development of atherosclerosis.

Atherosclerosis (also known as arteriosclerotic vascular disease or ASVD) is a specific form of arteriosclerosis in which an artery wall thickens as a result of invasion and accumulation of white blood cells, containing both living, active white blood cells (producing inflammation) and remnants of dead cells, including cholesterol and triglycerides. Atherosclerosis is therefore a syndrome affecting arterial blood vessels due to a chronic inflammatory response of white blood cells in the walls of arteries.

Arteriosclerosis is a condition involving thickening, hardening and loss of elasticity of the walls of arteries.

Coronary heart disease, also known as atherosclerotic artery disease, atherosclerotic cardiovascular disease, coronary heart disease or ischemic heart disease, is the most common type of heart disease and cause of heart attacks. The disease is caused by plaque building up along the inner walls of the arteries of the heart, which narrows the lumen of arteries and reduces blood flow to the heart.

Metabolic syndrome is a disorder of energy utilization and storage, diagnosed by a co-occurrence of three out of five of the following medical conditions: abdominal (central) obesity, elevated blood pressure, elevated fasting plasma glucose, high serum triglycerides, and low high-density cholesterol levels. Metabolic syndrome increases the risk of developing cardiovascular disease, particularly heart failure, and diabetes. Metabolic syndrome is also known as metabolic syndrome X, cardiometabolic syndrome, syndrome X, insulin resistance syndrome, Reaven's syndrome, and CHAOS (in Australia). Metabolic syndrome and pre-diabetes appear to be the same disorder, just diagnosed by a different set of biomarkers.

Acute coronary syndrome refers to a group of conditions due to decreased blood flow in the coronary arteries such that part of the heart muscle is unable to function properly or dies.

A xanthoma is a cutaneous manifestations of lipidosis in which lipids accumulate in large foam cells within the skin. Xanthomas are associated with hyperlipidemias.

Hypertension or high blood pressure, sometimes called arterial hypertension, is a chronic medical condition in which the blood pressure in the arteries is elevated.

Angina pectoris (or angina) refers to a sensation of chest pain, pressure, or squeezing, often due to ischemia of the heart muscle from obstruction or spasm of the coronary arteries. While angina pectoris can derive from anemia, cardiac arrhythmias and heart failure, its main cause is coronary artery disease.

Obesity is a medical condition in which excess body fat has accumulated to the extent that it may have a negative effect on health, leading to reduced life expectancy and/or increased health problems, such as increased risk of heart disease, type 2 diabetes, obstructive sleep apnea, certain types of cancer, and osteoarthritis.

Diabetes mellitus, commonly referred to as diabetes, is a group of metabolic diseases in which there are high blood sugar levels over a prolonged period. Several types of diabetes exist, including type I diabetes, type II diabetes and gestational diabetes. Type 1 diabetes is characterized by loss of the insulin-producing beta cells of the islets of Langerhans in the pancreas, leading to insulin deficiency. Type 2 diabetes is characterized by insulin resistance, which may be combined with relatively reduced insulin secretion. The defective responsiveness of body tissues to insulin is believed to involve the insulin receptor. Gestational diabetes, which resembles type 2 diabetes, occurs in about 2-10% of all pregnancies.

Sepsis is a potentially life-threatening complication of an infection that arises when the body's response to infection injures its own tissues and organs. During infection, the LDL receptors are also involved in the removal of bacterial lipids, such as lipopolysaccharide, from the circulation. PCSK9 inhibition may be a useful strategy to increase pathogen lipid clearance in the treatment of patients with sepsis (Walley et al., 2016).

Treatment of a Lipoprotein Metabolism Disorder

An individual or a subject in need of treatment of a disorder of lipoprotein metabolism is an individual suffering from, suspected of suffering from or at risk of suffering from a disorder of lipoprotein metabolism. In some embodiments, the individual in need of treatment is a mammal, preferably a human.

In preferred embodiments, the disorder of lipoprotein metabolism is selected from the group consisting of dyslipidemia, hypercholesterolemia and coronary heart diseases. In a preferred embodiment, the disorder of lipoprotein metabolism is coronary heart diseases.

In some embodiments, the treatment is prophylactic.

In some embodiments, the treatment comprises a step of administering to said subject a compound as disclosed herein. The compound can be administered at a daily dosage of between 0.1 mg and 1000 mg per kg bodyweight. Thus in some embodiments, the compound is administered at a daily dosage of between 0.1 mg and 1000 mg per kg bodyweight, such as between 0.2 and 900 mg per kg bodyweight, such as between 0.3 and 800 mg per kg bodyweight, such as between 0.5 and 700 mg per kg bodyweight, such as between 1.0 and 500 mg per kg bodyweight, such as between 5 and 400 mg per kg bodyweight, such as between 10 and 300 mg per kg bodyweight, such as between 25 and 250 mg per kg bodyweight, such as between 50 and 200 mg per kg bodyweight, such as between 75 and 150 mg per kg bodyweight, such as between 100 and 125 mg per kg bodyweight. In some embodiments, the compound is administered at a daily dosage of between 0.1 mg and 1000 mg per kg bodyweight, such as between 0.1 and 10 mg per kg bodyweight, such as between 10 and 25 mg per kg bodyweight, such as between 25 and 50 mg per kg bodyweight, such as between 50 and 100 mg per kg bodyweight, such as between 100 and 250 mg per kg bodyweight, such as between 250 and 500 mg per kg bodyweight, such as between 500 and 750 mg per kg bodyweight, such as between 750 and 1000 mg per kg bodyweight.

The etiology underlying the indications to be treated according to the present invention, is increased levels of LDL-C in the blood of the patient. Thus, in one aspect the present invention concerns a method of inhibiting degradation of LDLR, which results in increased binding of LDL-C to said LDLR. The patient is thus treated by administering a compound as defined in general formula (I).

Accordingly, is provided herein a method for reducing plasma LDL-C levels in a subject in need thereof, said method comprising the step of administering to said subject a compound or a pharmaceutical composition as defined herein. Plasma LDL-C levels can be determined in vivo or in vitro by any method known in the art, as described above.

In one aspect, the invention relates to a method for reducing plasma lipoprotein levels in a subject in need thereof, said method comprising the step of administering to said subject a compound or a pharmaceutical composition as defined herein.

Pharmaceutical Composition

Also disclosed herein is a pharmaceutical composition comprising at least one compound as defined herein. In some embodiments, the composition comprises one compound as disclosed herein. In other embodiments, the composition comprises two compounds or more, such as three compounds or more, such as four compounds or more, such as five compounds or more.

In some embodiments, the composition further comprises at least one of:
an antibody inhibiting binding of PCSK9 to LDLR;
a statin;
cholestyramine
a cholesterol absorption inhibitor e.g. ezetimibe.

In some embodiments, the compound is administered in combination with another compound, such as an anti-PCSK9 antibody, such as an antibody binding to the LDLR-binding site of PCSK9, or a statin. In some embodiments, the compound is administered together with an antibody selected from the group consisting of: lodelcizumab, ralpancizumab, alirocumab, evolocumab and bococizumab.

Thus in some embodiments, the pharmaceutical composition comprises at least one compound as defined herein and at least one additional compound selected from the group consisting of an antibody inhibiting binding of PCSK9 to LDLR, a statin or cholestyramine. In one embodiment, the pharmaceutical composition comprises one compound as defined herein and an antibody inhibiting binding of PCSK9 to LDLR. In one embodiment, the pharmaceutical composition comprises one compound as defined herein and a statin. In one embodiment, the pharmaceutical composition comprises one compound as defined herein and cholestyramine. In one embodiment, the pharmaceutical composition comprises one compound as defined herein, an antibody inhibiting binding of PCSK9 to LDLR and a statin. In one embodiment, the pharmaceutical composition comprises one compound as defined herein, an antibody inhibiting binding of PCSK9 to LDLR and cholestyramine. In one embodiment, the pharmaceutical composition comprises one compound as defined herein, cholestyramine and a statin. In one embodiment, the pharmaceutical composition comprises one compound as defined herein, an antibody inhibiting binding of PCSK9 to LDLR, a statin and cholestyramine.

The pharmaceutical composition optionally comprises one or more pharmaceutically acceptable carriers excipients, and is prepared by conventional techniques, e.g. as described in Remington: The Science and Practice of Pharmacy 1995, edited by E. W. Martin, Mack Publishing Company, 19th edition, Easton, Pa. The compositions may appear in conventional forms, for example capsules, tablets, aerosols, solutions, suspensions or topical applications. Typically, the pharmaceutical compositions of the present invention is formulated for parenteral administration e.g., by intravenous or subcutaneous injection, and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. The compositions may be suitable for oral ingestion. This is particularly relevant for small molecule compositions. Examples of oily or non-aqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water. Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. The parenteral formulations typically will contain from about 0.0001 to about 25%, such as from about 0.5 to about 25%, by weight of the active ingredient in solution. Preservatives and buffers may be used. In order to minimise or eliminate irritation at the site of injection, such compositions may contain one or more nonionic surfactants having a hydrophile-lipophile balance (HLB) of from about 12 to about 17. The quantity of surfactant in such formulations will typically range from about 0.000001 to about 15% by weight, such as from about 0.000001 to about 5% by weight or from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use.

The main route of drug delivery according to this invention is however parenteral in order to introduce the agent into the blood stream to ultimately target the relevant tissue.

In one embodiment, the agent is administered to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth.

In a preferred embodiment the agent of the invention is administered parenterally, that is by intravenous, intramuscular, intraspinal, subcutaneous, intranasal, intrarectal, intravaginal or intraperitoneal administration. The subcutaneous and intramuscular forms of parenteral administration are generally preferred. Appropriate dosage forms for such administration may be prepared by conventional techniques. The compounds may also be administered by inhalation, which is by intranasal and oral inhalation administration. Appropriate dosage forms for such administration, such as an aerosol formulation or a metered dose inhaler, may be prepared by conventional techniques.

In one embodiment the pharmaceutical composition according to the present invention is formulated for parenteral administration such as by injection.

In a further embodiment the pharmaceutical composition according to the present invention is formulated for intravenous, intramuscular, intraspinal, intraperitoneal, subcutaneous, a bolus or a continuous administration.

The rate and frequency of the administration may be determined by the physician from a case to case basis. In one embodiment the administration occurs at intervals of 30 minutes to 24 hours, such as at intervals of 1 to 6 hours, such as once daily.

The duration of the treatment may vary depending on severity of the disorder. In one embodiment the duration of the treatment is from 1 day to 28 days, such as from 2 days to 25 days, such as from 5 days to 20 days, such as from 7 days to 15 days. In chronic cases the duration of the treatment may be lifelong.

The dosage can be determined by the physician in charge based on the characteristics of the patient and the means and mode of administration. In one embodiment of the present invention, the dosage of the active compound of the pharmaceutical composition as defined herein above is between 0.1 mg and 1000 mg per kg bodyweight.

The dosage may be administered as a bolus administration or as a continuous administration. In relation to bolus administration the pharmaceutical composition may be administered at intervals of 30 minutes to 24 hours, such as once daily.

In some embodiments, the pH of the composition is between pH 4 and pH 10.

In some embodiments, the composition is formulated for oral administration.

In some embodiments, the composition is formulated for parenteral administration. In specific embodiments, the parenteral administration is by injection. Such parenteral administration may be intravenous, intramuscular, intraspinal, intraperitoneal, subcutaneous, a bolus or a continuous administration.

In one embodiment, the compound disclosed herein is a heparin analogue stable in serum.

Also provided herein is a compound as defined above which is non-toxic, in particular after administration. In some embodiments, the compound is a heparin analogue which is non-toxic after administration.

EXAMPLES

Example 1: Mapping of the HSPG Binding Site in PCSK9

Figure 2:
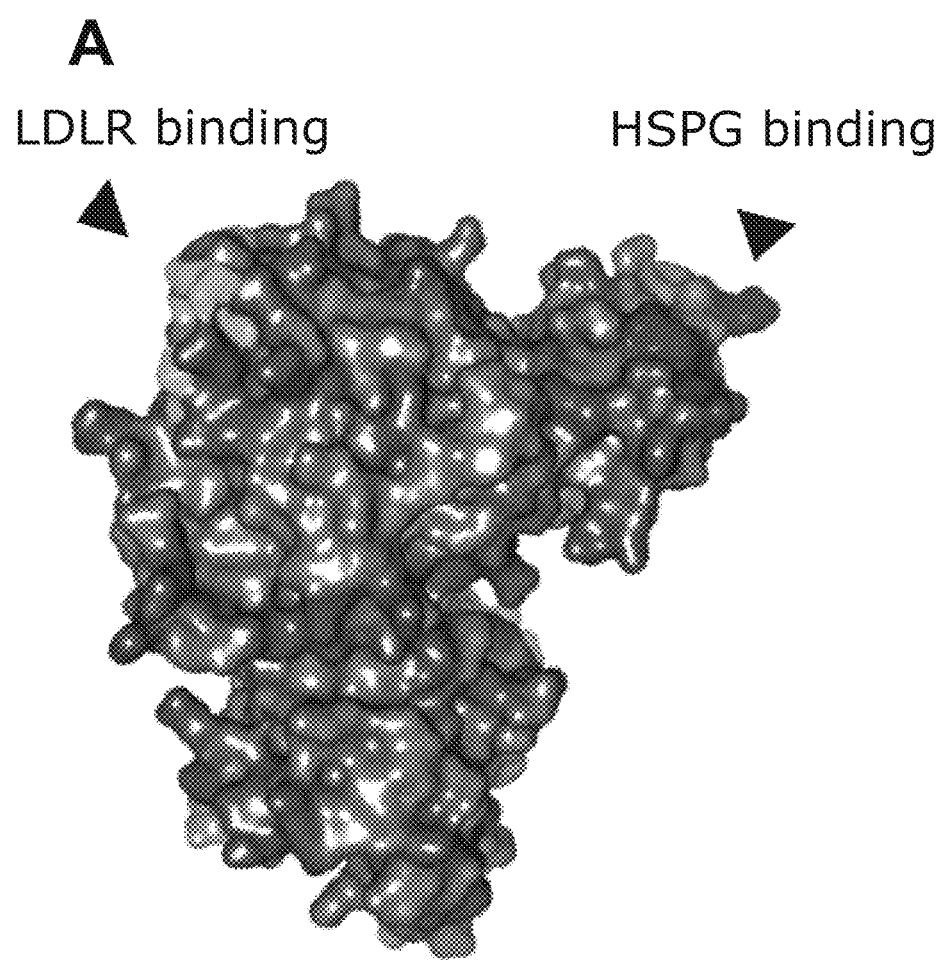
FIG. 2: (A) Shown is a spacefilling model of PCSK9 with the LDLR binding site and the HSPG binding sites indicated by the left and right arrowheads, respectively. (B) A heparin pentasaccharide (SANORG, sticks) at the electrostatic surface (red negative; blue positive) of the predicted HSPG binding site in PCSK9 (PDB ID: 2PMW) (Piper et al., 2007) with positively charged amino acids (R: arginine, H: histidine) indicated. (C) Superposition of SANORG onto the HSPG binding site in PCSK9 (ribbon). (D) Non-permeabilized HepG2 cells expressing PCSK9 (white) after treatment with or without heparinase I. Nuclei were stained with Hoechst (dark grey). (E) PCSK9 binding to heparin was analyzed by heparin affinity chromatography. PCSK9 was eluted from the column at a NaCl concentration of 500 mM.
Figure 2:
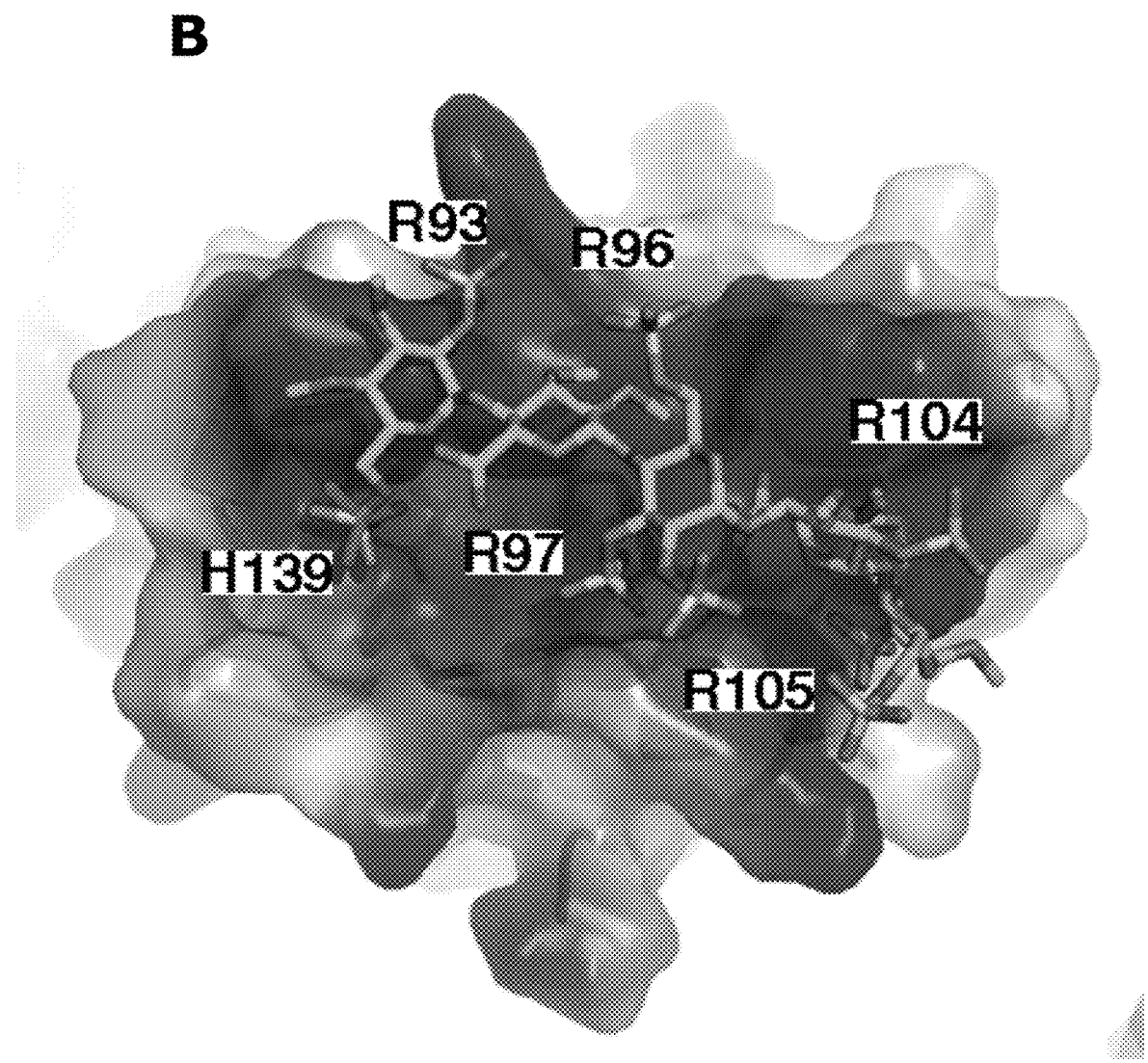
Figure 2:
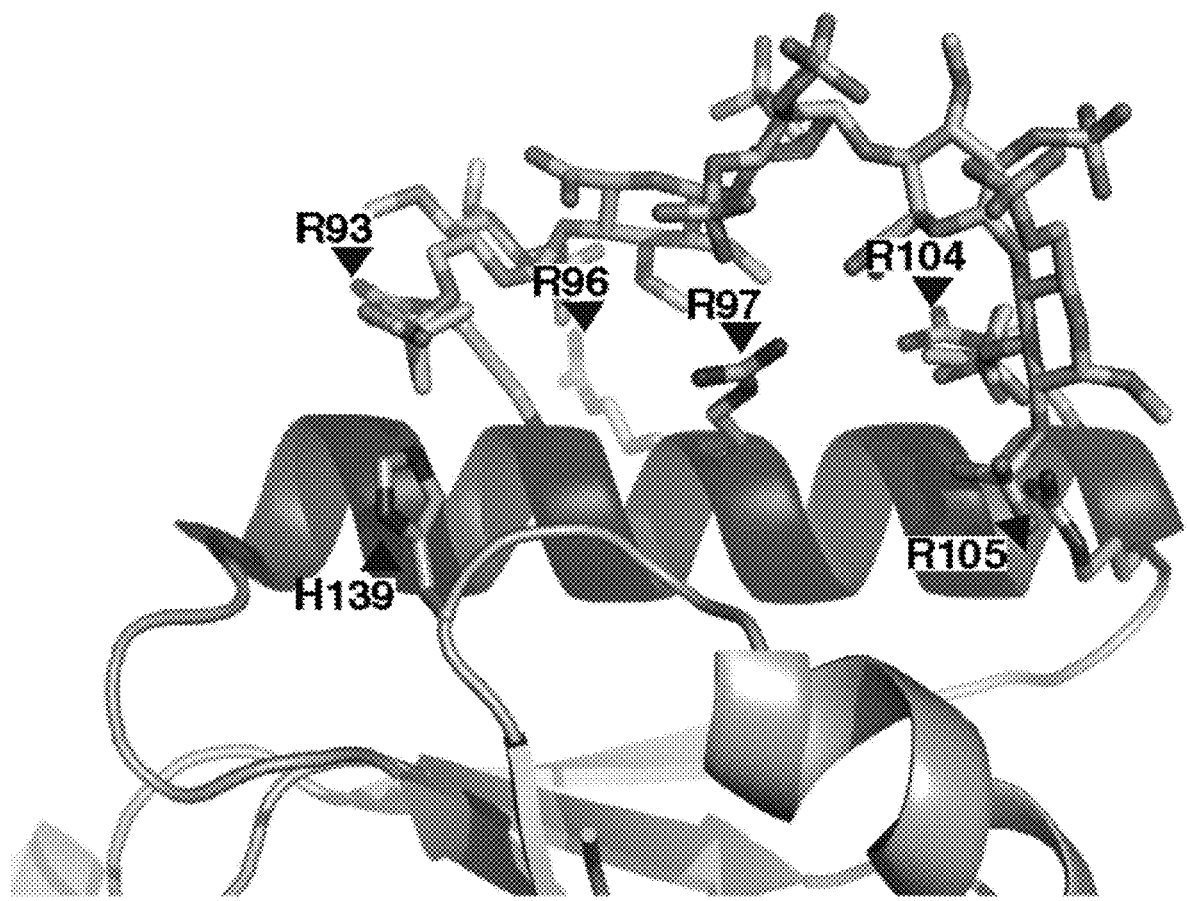
Figure 2:
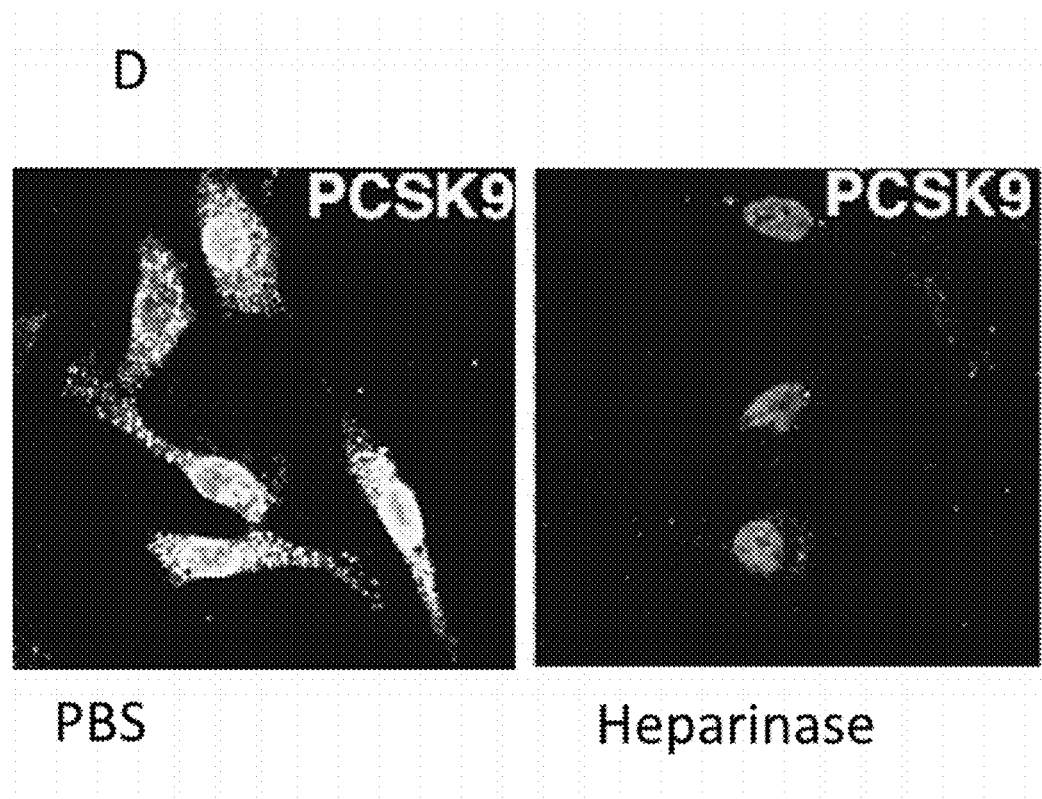
Figure 2:
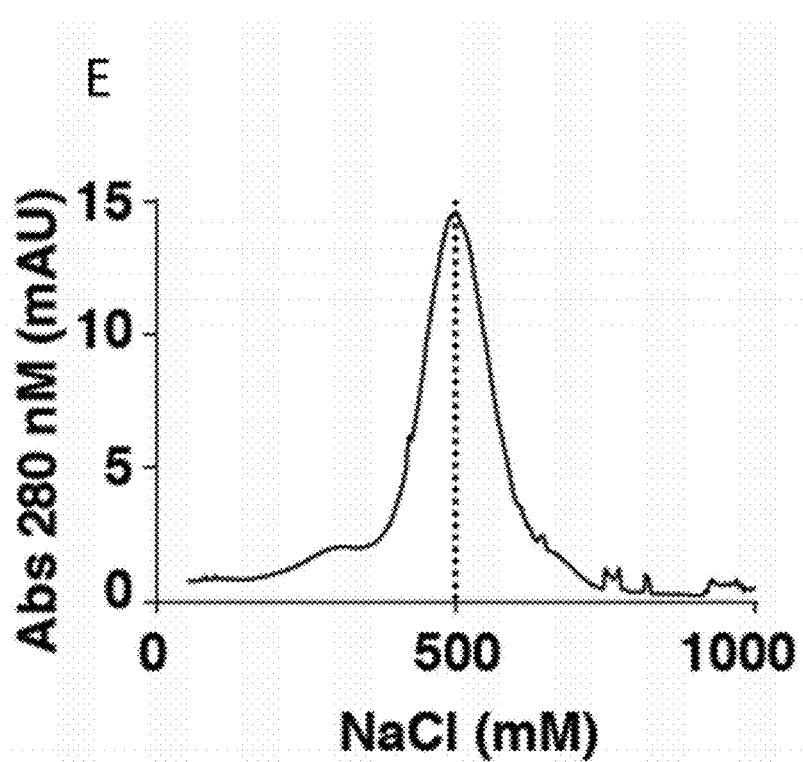
Figure 3:
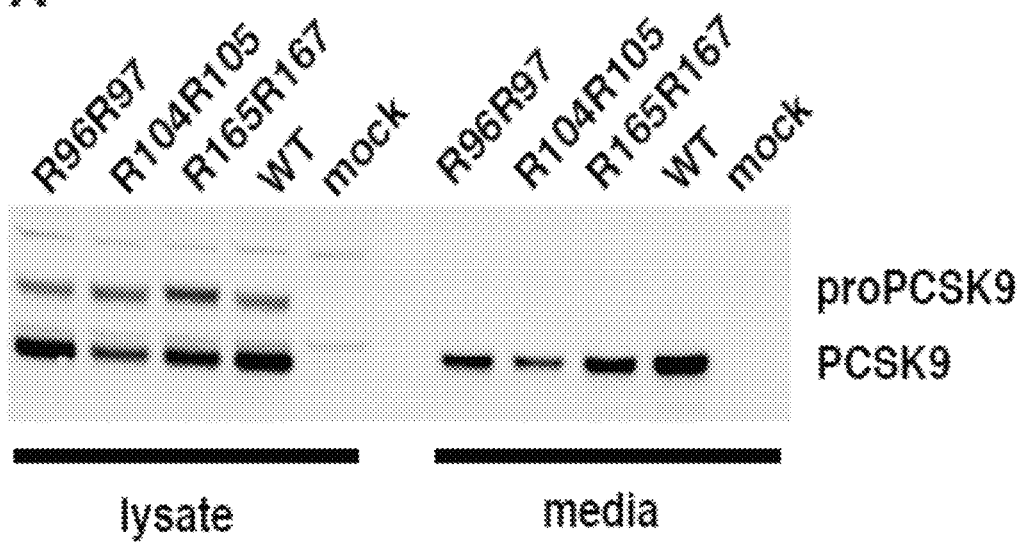
FIG. 3: PCSK9 variants, in which indicated amino acid residues were mutated to alanine, were transiently expressed in CHO cells. (A) Anti-PCSK9 Western blotting of cell lysate and media showed expression of all PCSK9 variants as well as correct processing from proprotein (proPCSK9) into mature PCSK9 in the cell lysate, and secretion of mature PCSK9 to the media of the cells. No expression of PCSK9 was detected in mock transfected cells. (B) PCSK9 mutants secreted to the media of transiently transfected CHO cells were analysed for binding to heparin by affinity chromatography followed by Western blotting of fractions with anti-PCSK9. All mutants have alanine substitutions at the indicated positions. Wildtype (WT) PCSK9 and mutant R165R167 were eluted in fractions corresponding to 0.3-0.4 M NaCl, whereas PCSK9 mutants R96R97 and R104R105 showed decreased affinity for heparin and were found in the flow through or in the first fraction. PCSK9 mutants R93R104R105H139 and R93R96R97R104R105H139 were found exclusively in the flow through and did not bind to heparin. (C) The HSPG binding domain is positioned opposite the LDLR binding site as shown in a space filling model of PCSK9 in a surface representation of PCSK9 in complex with a LDLR fragment (PDB:3P5B). The LDLR fragment contains the beta propeller domain and EGF domains A and B and L7, while PCSK9 C-terminal, catalytic domain, and prodomain are shown with the basic helix. The modeled heparin fragment is shown as sticks. (D) Endogenous PCSK9 and ApoE from the culture medium of HepG2 cells showed similar binding to heparin when analyzed by affinity chromatography and Western blot.
Figure 3:
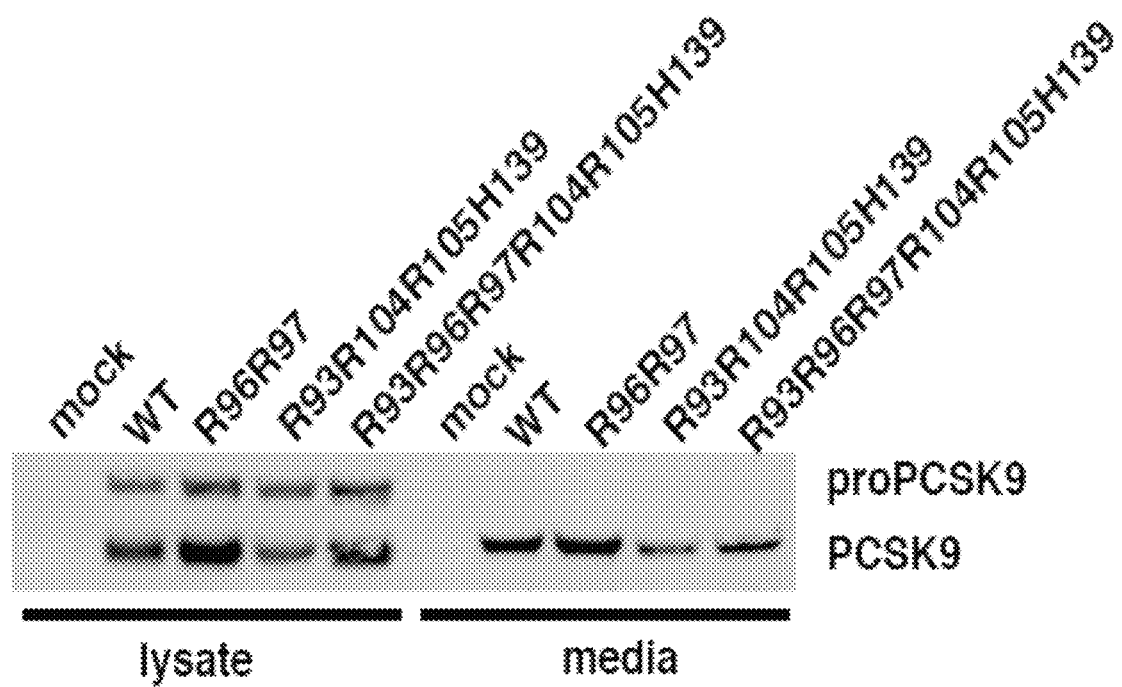
Figure 3:
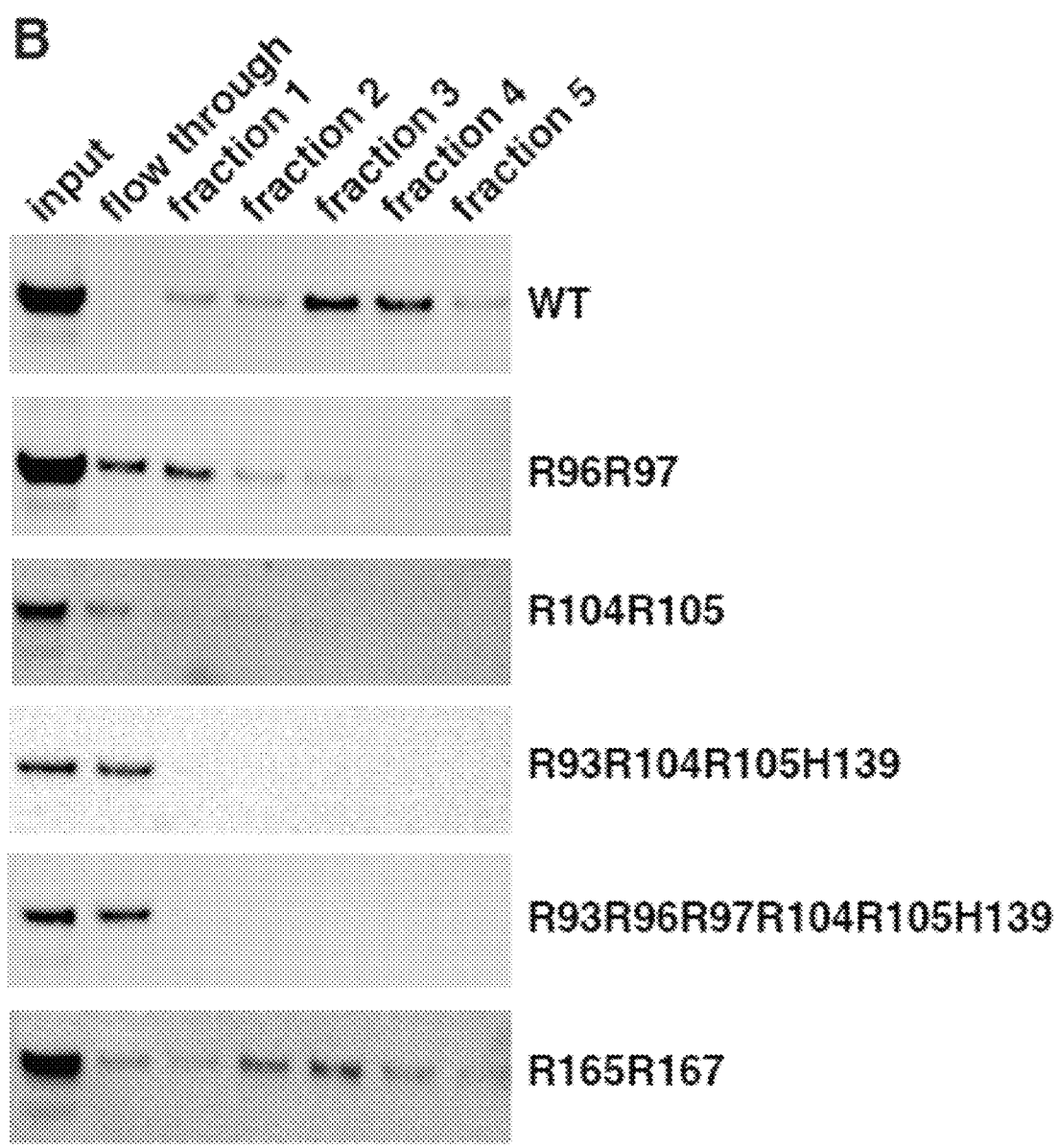
Figure 3:
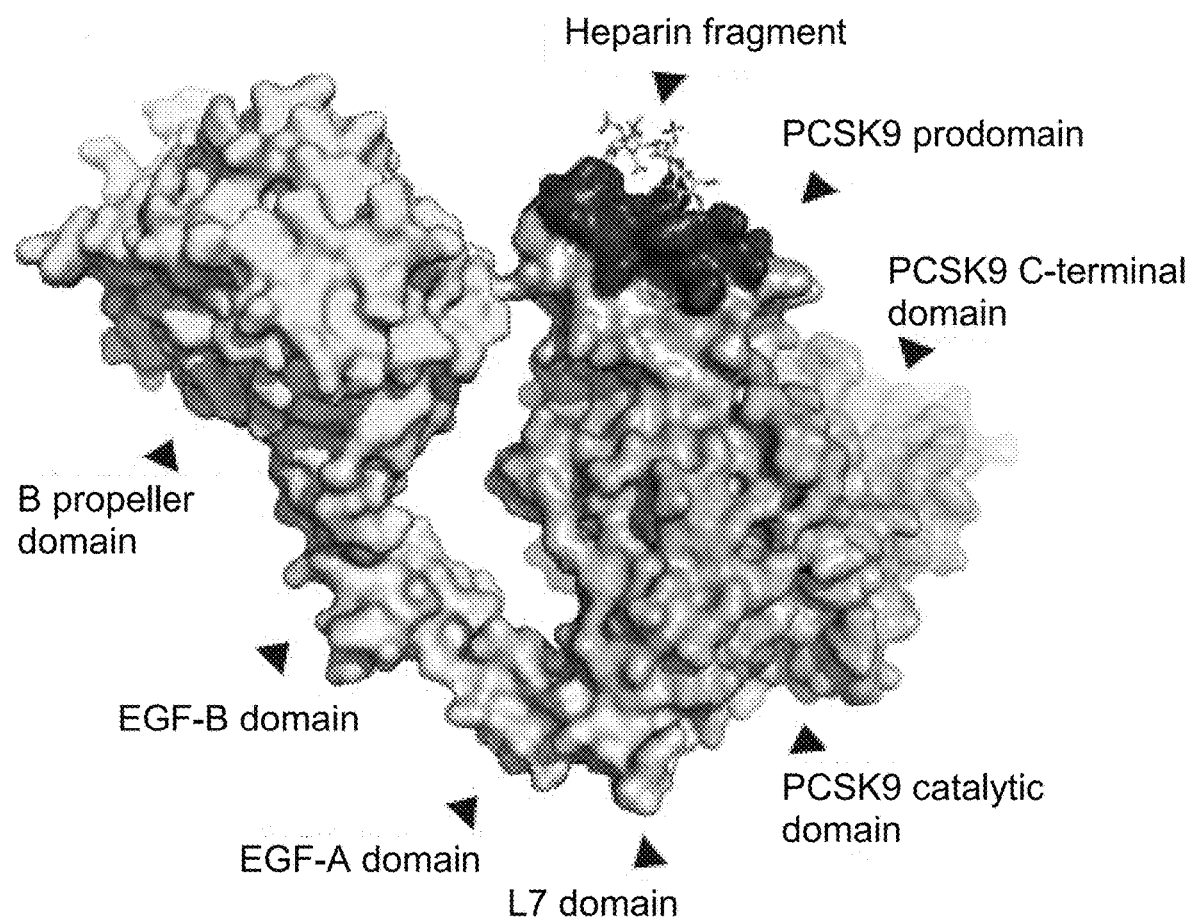
Figure 3:
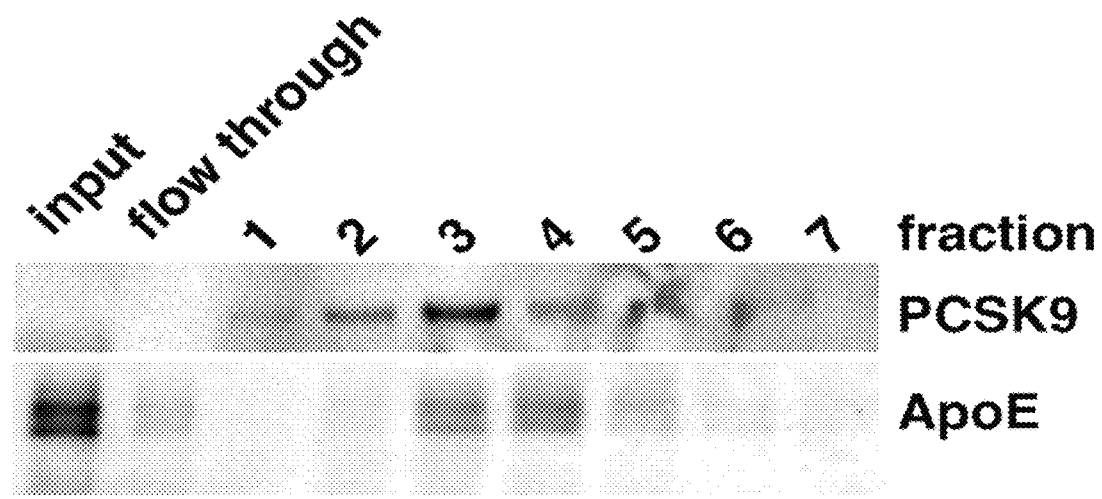

We examined the electrostatic surface of PCSK9 (PDB: 2PMW) (FIG. 2B), and identified a putative heparin binding site composed of six surface exposed basic residues located in the PCSK9 prodomain. The binding site is formed by arginine (R) residues at position 93, 96, 97, 104, and 105 and histidine (H) at position 139, which show perfect pairing with sulfate groups of a heparin pentasaccharide (SANORG) (Herbert et al., 1996) (Herbert et al., 1996) (FIGS. 2B and 2C). The site is found opposite to the LDLR binding surface located in the inactive catalytic domain of PCSK9 (FIG. 2A). Docking of heparin fragment onto a co-crystal structure of PCSK9 in complex with LDLR (PDB:3P5B) suggested that heparan sulfate binding allows subsequent PCSK9: LDLR complex formation (FIG. 3C).

Example 2: Heparinase Treatment Inhibits PCSK9 Cell Surface Association In Vitro and Protects the LDL Receptor Against PCSK9-Induced Degradation In Vivo We speculated that HSPG might be involved in the capture of PCSK9. Thus, we treated human hepatocyte-derived HepG2 cells stably expressing PCSK9 with heparinase I. The enzyme heparinase I cleaves heparan sulfate GAG chains at the 1,4 O-linkage between uronic acid and N-acetyl-D-glucosamine, thereby removing cell surface heparan sulfate chains.

HepG2 cells stably transfected with PCSK9 were seeded at 50.000 cells per coverslip and incubated overnight before addition of heparinase I (Sigma Aldrich/H2519) in PBS (0,0002 UN/ml) or PBS alone. Cells were incubated for 1 h. at 37° C., before fixation in 4% paraformaldehyd and immunostaining of non-permeabilized cells with primary and secondary antibodies. Nuclei were visualized with Hoechst dye (Sigma Aldrich). Images were acquired on a Zeiss LSM780.

Indeed, treatment resulted in a marked decrease in the intensity of surface PCSK9 staining, suggesting that HSPG are critical for PCSK9 cell binding (FIG. 2D).

Figure 10:
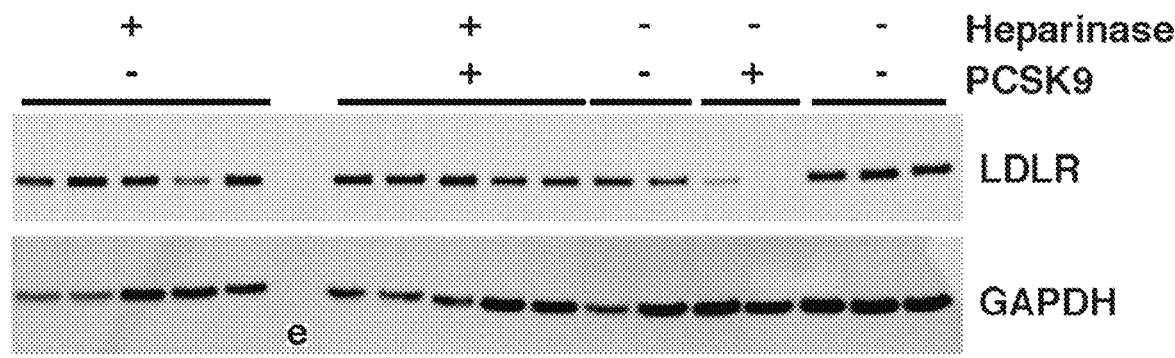
FIG. 10: Infusion of heparinase I prior injection of PCSK9 (10 μg) completely inhibits PCSK9 induced degradation of LDLR. Shown is a Western blot of representative samples (A) and bar graph quantification of LDLR (B). For Western blots, GAPDH is used as a loading control. e: empty lane. Control n=7, PCSK9 n=6, heparinase n=5, heparinase/PCSK9 n=5. Mice co-injected with PCSK9 (10 μg) and heparin (50 U) or suramin (300 μg) show significantly higher level of LDLR compared to mice injected with PCSK9 alone (C). Control n=15, PCSK9 n=10, PCSK9/heparin n=7, PCSK9/suramin n=3. (D) Plasma levels of PCSK9 after intravenous injection of heparin (50 u) as assessed by murine PCSK9 specific ELISA.
Figure 10:
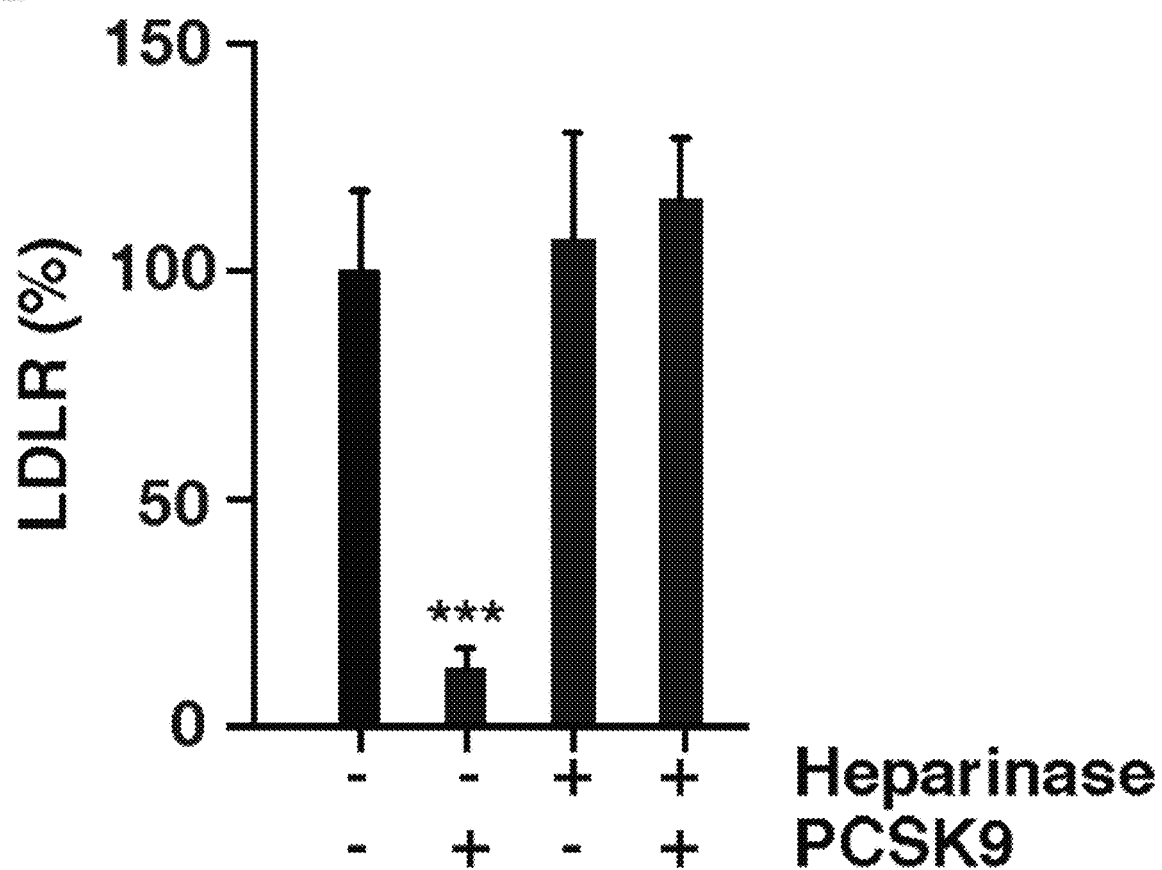
Figure 10:
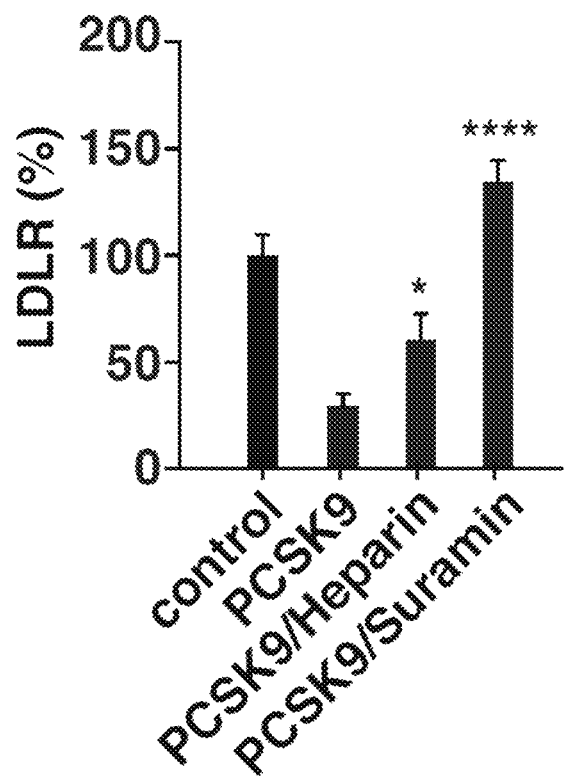
Figure 10:
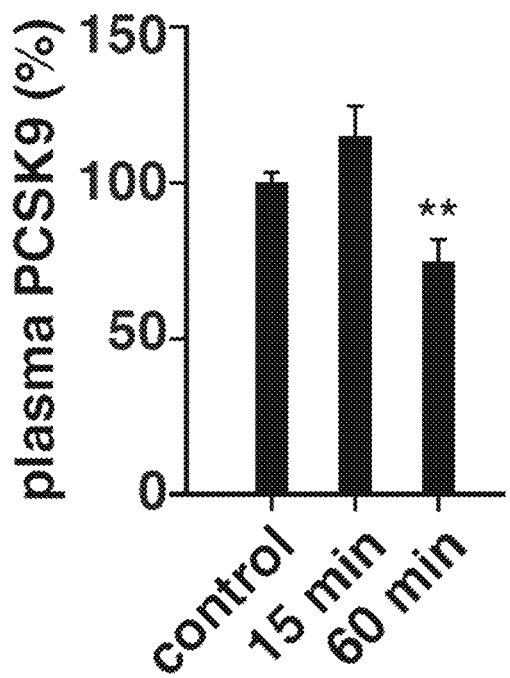
Figure 11:
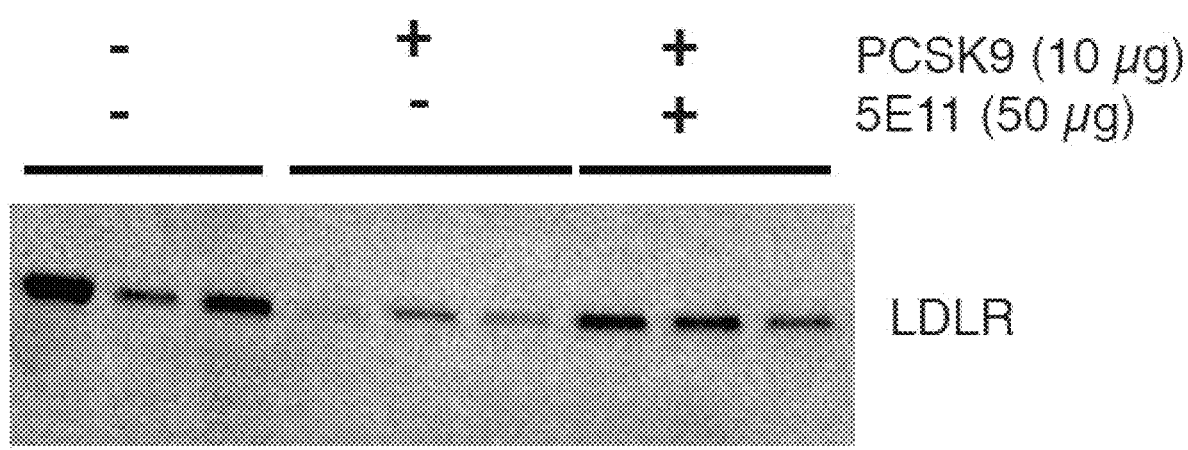
FIG. 11: LDLR levels in liver of mice 1 hour after intraveinous administration of 10 μg PCSK9 alone or in combination with 50 μg PCSK9 inhibitory antibody 5E11.

To test the effect of enzymatic removal of heparan sulfate GAGs on PCSK9 activity in vivo 10-12 week-old male BALB6/cJRj mice were infused with heparinase I (30 U) administered through a tail vein catheter 5 min prior injection of PCSK9 (10 µg). In control mice the heparinase injection and/or the PCSK9 injection were replaced with an injection of 0.9% saline. During heparinase infusion, mice were lightly anaesthetized with isoflurane continuously administered through a mask. One hour post injection mice were sacrificed and liver tissue samples were harvested and snap frozen before extraction of proteins and evaluation of LDLR levels by Western blot (FIG. 10 A) Injection of heparinase I completely protected LDLR from PCSK9- induced degradation, demonstrating that HSPGs are instrumental in PCSK9 induced degradation of LDLR in vivo (FIGS. 10 A and B).

To verify the direct interaction between PCSK9 and heparan sulfate GAG chains, we employed affinity chromatography using Sepharose beads covalently coupled with heparin.

Purified PCSK9 was loaded onto a 5 ml HiTrap Heparin HP column (GE Healthcare) in PBS. The column was connected to an Äkta Prime and washed with 5 column volumes of 10 mM $NaH_2PO_4$ (pH 7.4). PCSK9 was eluted using a linear gradient of 10 mM $NaH_2PO_4$ (pH 7.4) and 2 M NaCl and fractions were analyzed by SDS-PAGE. Based on the measured conductivity, the elution profile was transformed to a function of NaCl concentration using the transformation coefficient 0.065 mS/mM NaCl. Purified PCSK9 was retained on the heparin column and eluted at a NaCl concentration of approximately 500 mM (FIG. 2E), indicating a strong and highly specific interaction with heparin.

In a different experiment, conditioned media from HepG2 cells or CHO cells transfected with PCSK9 variants of interest were incubated with Heparin Sepharose CL-6B beads (GE Healthcare) in 10 mM $NaH_2PO_4$ (binding buffer). Following overnight incubation on a rotor at 4° C., beads were washed in binding buffer before batch elution of heparin bound proteins in increasing concentration of NaCl. PCSK9 in input, flow through, and elution fractions were evaluated by Western blotting.

We found that endogenous PCSK9 from conditioned media of HepG2 cells also bound heparin and showed similar elution profile as that of ApoE, a well-established HSPG binding protein (FIG. 3D).

Example 3: Identification of Residues Important for the PCSK9/HSPG Interaction

To further narrow down critical residues involved in the PCSK9/HSPG interaction, PCSK9 variants with point mutations in the HSPG binding motif were cloned and expressed. Mutations were introduced by PCR in order to replace the charged amino acid arginine (Arg/R), lysine (Lys/K) and histidine (His/H) identified by 3D structure model docking by neutral residues such as alanines (Ala/A).

The human wild type and the following alanine substitution variants were analysed:
Wild type PCSK9 (SEQ ID NO: 1)
Mutant R93
Mutant R96R97
Mutant R104R105
Mutant R165R167
Mutant R93R104R105H139A
Mutant R93R96R97R104R105H139

Since improper folded PCSK9 is generally not cleaved in the propeptide and therefore retained in the endoplasmic reticulum, correct folding of the PCSK9 mutant variants can be evaluated by monitoring their processing and secretion. Processing of proPCSK9 into mature protein and secretion of mature PCSK9 variants were assessed by transient transfection of Chinese Ovary Hamster (CHO) cells followed by Western blot analysis of PCSK9 in cell lysates and in the surrounding medium (FIG. 3A).

The ability of the PCSK9 mutant proteins to bind to heparin was assessed by affinity chromatography followed by Western blotting with anti-PCSK9 antibody. Conditioned media from CHO cells transfected with PCSK9 variants of interest were incubated with Heparin Sepharose CL-6B beads (GE Healthcare) in 10 mM $NaH_2PO_4$ (binding buffer). Following overnight incubation on a rotor at 4° C., beads were washed in binding buffer before batch elution of heparin bound proteins in increasing concentration of NaCl. PCSK9 in input, flow through, and elution fractions were evaluated by Western blotting.

Mutants R93, R96R97 and R104R105 show less affinity for heparin compared to wild-type PCSK9 or mutant R165R167, and mutants R93R104R105H139 and R93R96R97R104R105H139 do not bind heparin and are found exclusively in the flow-through (FIG. 3B).

Example 4: PCSK9 Variant with Mutated HSPG-Binding Domain Fails to Induce LDL Receptor Degradation Purified PCSK9 variants were tested in a cell assay to test their ability to induce degradation of LDLR compared to wild-type PCSK9. Induction of LDLR degradation was analyzed by incubation of HepG2 cells with wild type PCSK9 (WT) or the above PCSK9 mutants and LDLR levels were assessed by Western blotting. HepG2 cells were seeded at a density 250.000 cells per well in 12-well plates. After overnight incubation, the media was replaced with fresh media containing PCSK9 WT or mutant R93R96R97R104R105H139. Cells were harvested and lysed following 18 hours incubation and LDLR levels were assessed by Western blotting and quantification by densitometry.

Figure 4:
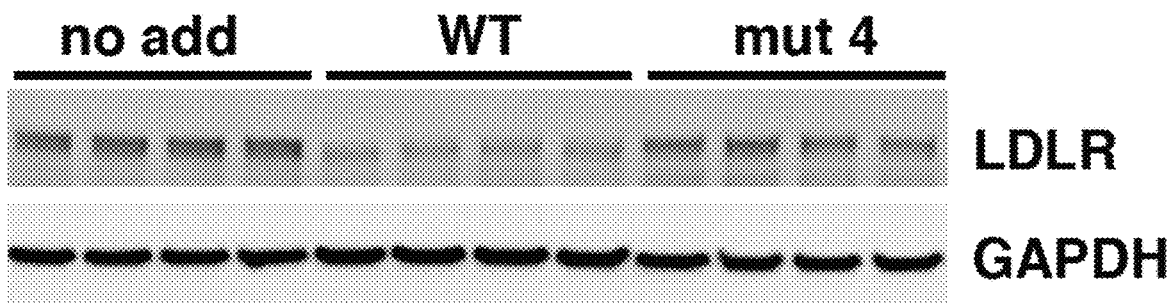
FIG. 4: HepG2 cells incubated 18 hours with WT PCSK9 (10 nM) show significantly lower levels of LDLR than cells incubated with mutant (R93R96R97R104R105H139) PCSK9 (mut 4). LDL receptor levels were evaluated by Western blotting (A), levels of GAPDH are shown as control. Bar graphs (B) show average values of LDLR quantified by densitometry (n=3) with standard error of mean (SEM). Results were evaluated using student's t-test. p<0.01, **p<0.0001.
Figure 4:
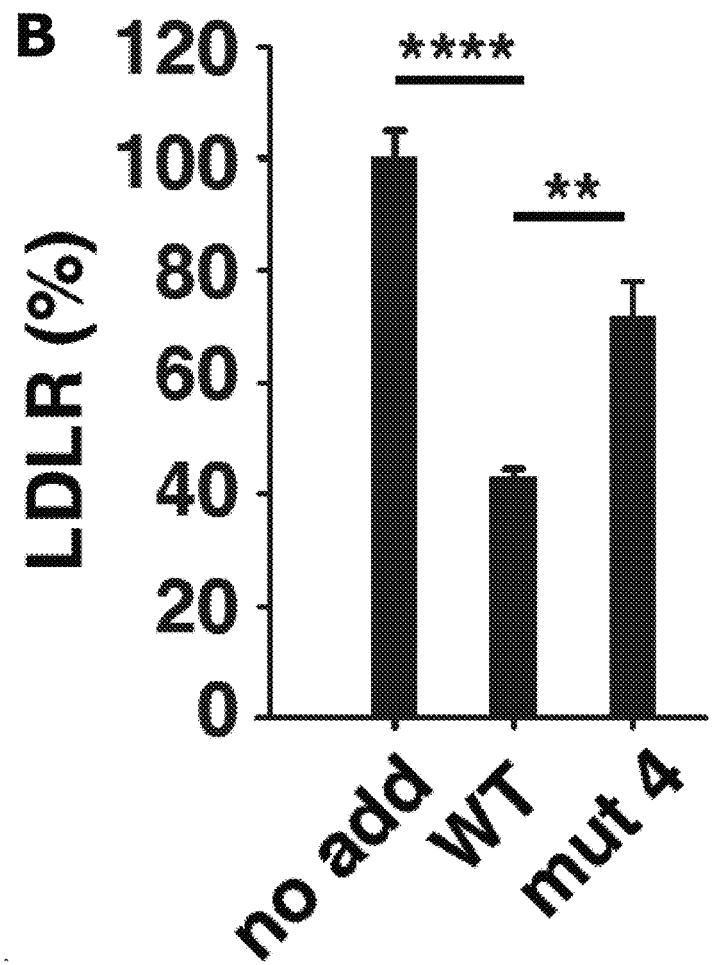

The LDLR levels in cells incubated with mutant R93R96R97R104R105H139 were markedly (approximately twice) higher compared to the levels measured in cells incubated with WT PCSK9 (FIGS. 4A and B), showing that mutations within the HSPG-binding domain resulted in reduced PCSK9-induced LDLR degradation.

Example 5: Heparin and Heparin Analogues Prevent PCSK9:LDLR Complex Formation

Using proximity ligation assay (PLA), we tested whether exogenously added heparin competes with cell surface HSPG for the binding of endogenous PCSK9 and thereby prevent PCSK9:LDLR complex formation (Soderberg et al., 2006).

The PLA (Duolink®II, Olink Bioscience) was performed according to manufacturer's protocol using anti-PCSK9 (R&D systems/AF3888), and anti-LDLR (Abcam/ab52818) as primary antibodies. PCSK9 and LDLR located within 30 nm from each other are visualized by oligonucleotide-conjugated secondary antibodies that hybridize with circle-forming oligonucleotides thereby priming rolling circle amplification. The amplified DNA is visualized by addition of complementary fluorescently-labeled oligonucleotides (Soderberg et al., 2006)

Figure 5:
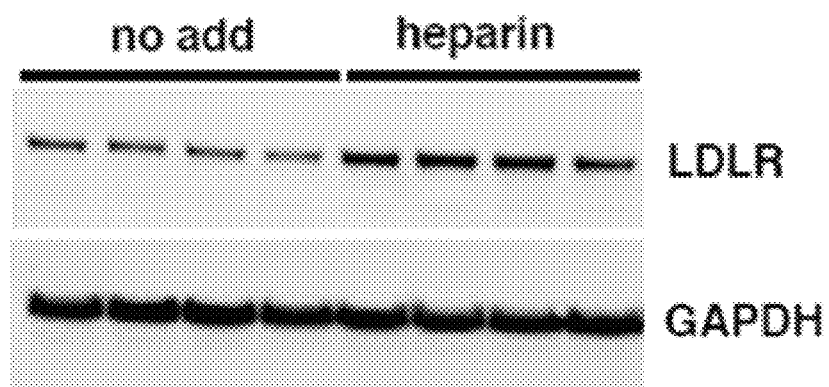
FIG. 5: HepG2 cells incubated 24 h with heparin (50 U/ml) show increased levels of LDLR evaluated by Western blotting (A). GAPDH levels are shown as control. Bar graphs (B) show average values with standard error of mean (SEM) of LDLR quantified by densitometry (n=4). Incubation with heparin also results in increased PCSK9 levels in the medium as measured by ELISA (C). Bar graphs show the average PCSK9 concentration with SEM (n=4). Results were evaluated using student's t-test. *p<0.001, **p<0.0001. (D)=PLA analysis of non-permeabilized HepG2 cells showed that co-localization between LDLR and PCSK9 was markedly reduced upon incubation of cells with heparin (50 U/ml).
Figure 5:
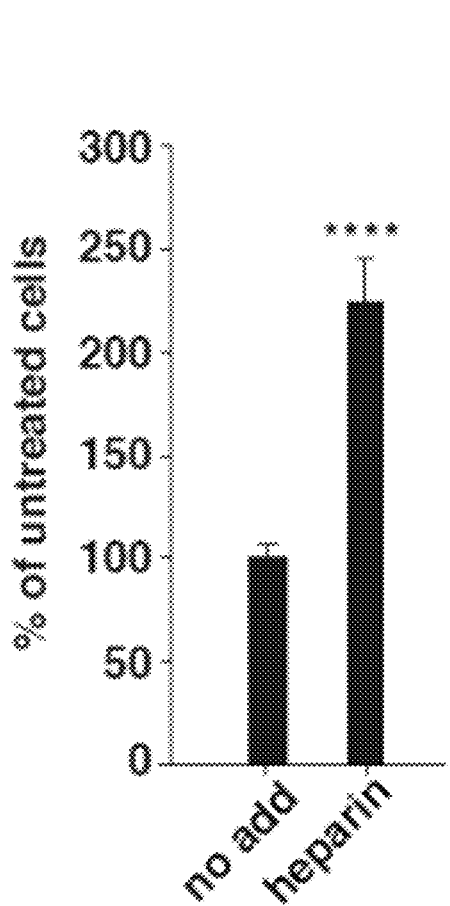
Figure 5:
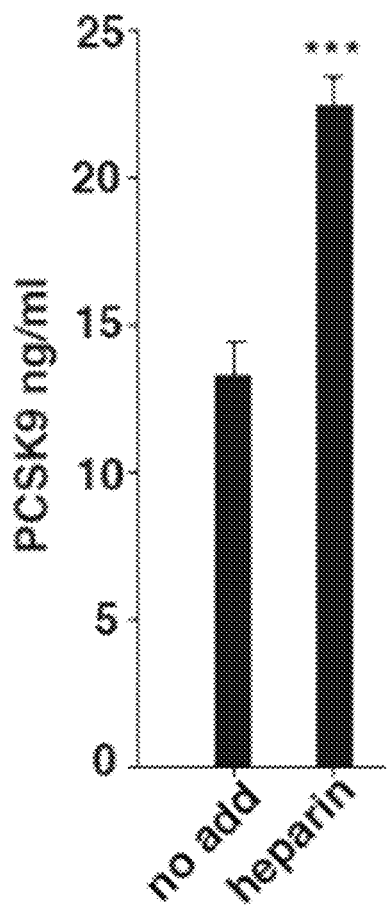
Figure 5:
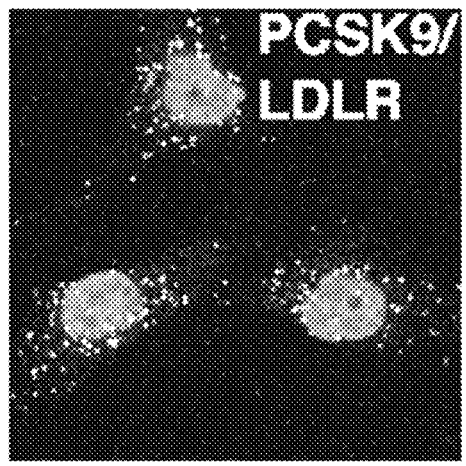
Figure 5:
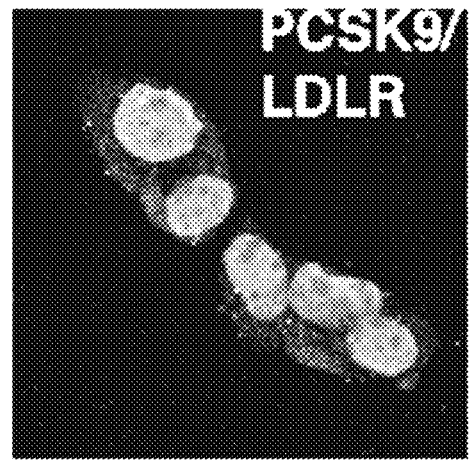

Using this assay on endogenous cell surface PCSK9 and LDLR in non-permeabilized HepG2 cells, abundant clusters of PCSK9:LDLR complexes were observed (FIG. 5D). These were markedly reduced both in numbers and intensity upon incubation with heparin, suggesting that PCSK9 binding to HSPG is instrumental in the subsequent complex formation with cell surface LDLR.

Figure 8:
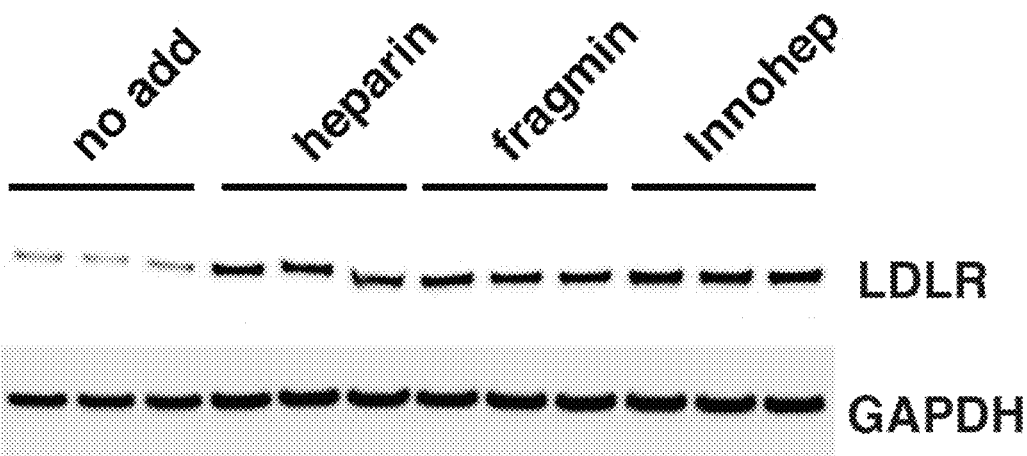
FIG. 8: (A) Western blot of LDLR in HepG2 cells following 18 hours incubation with fragmin (100 U/ml) and Innohep (100 U/ml), showing that these two therapeutic preparations of low-molecular weight heparins can increase the cellular level of LDLR comparable to the effect of heparin (50 U/ml). Western blot of GAPDH is shown as loading control. (B) Western Blot showing LDLR levels in liver of mice 1 hour after intravenous administration of 10 μg PCSK9 alone or in combination with 50 U Heparin. 50 μg membrane preparations were loaded. As control is shown Western Blot for sortilin, a PCSK9 receptor previously shown not to be target of PCSK9 induced degradation. (C) Quantification of B) Bands were quantified by densitometry and dot plot show the individual level of each sample in percent of vehicle (0.9% NaCl) injected controls with mean values and SEM. Mice co-injected with PCSK9 and Heparin show significantly higher level of LDLR (60.3±12.3% LDLR versus 24.0±4.04%, n=7 mice/group, p=0.0157, two-tailed student's t-test).
Figure 8:
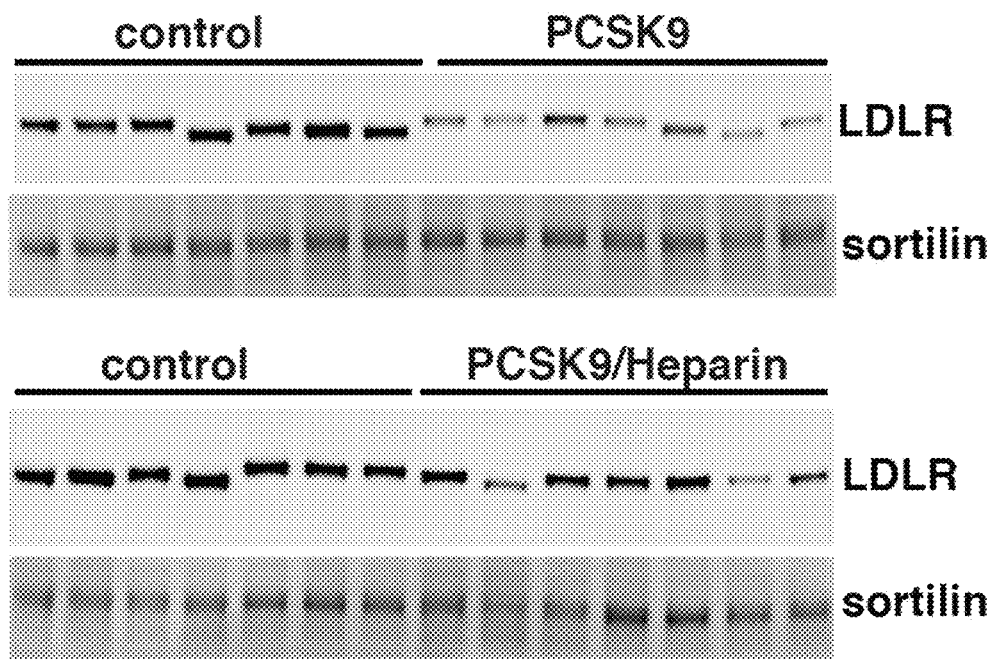
Figure 8:
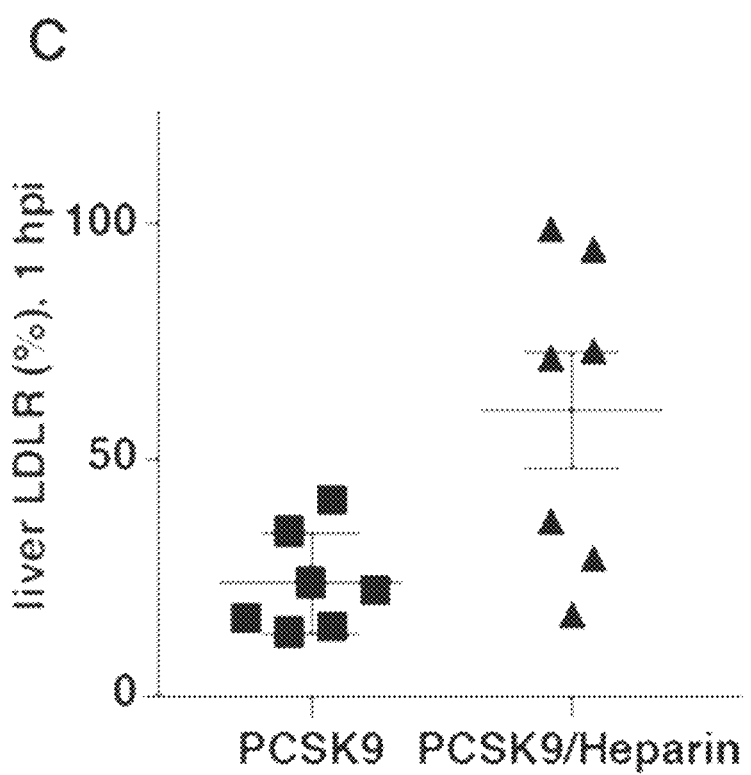

We found that incubation of HepG2 cells with heparin (50 U/ml for 18 hrs) resulted in two to three-fold higher level of LDLR protein (FIG. 5A-5B), and a similar effect was observed with two other therapeutic preparations of low-molecular weight heparins (FIG. 8A).

Figure 6:
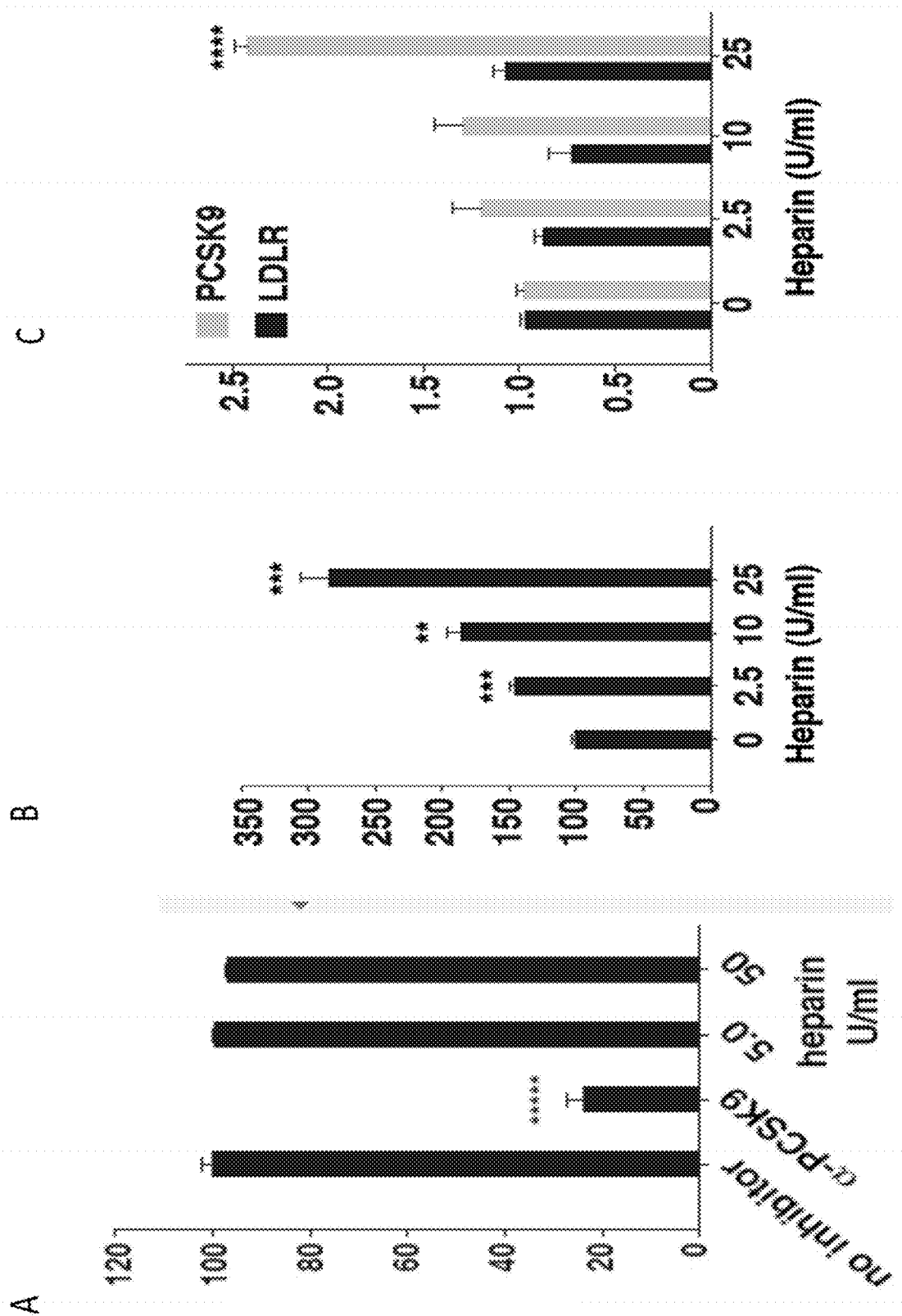
FIG. 6: (A) Using a cell-free PCSK9/LDLR binding assay (BPS Bioscience) we found that heparin (5 and 50 U/ml) does not inhibit the direct interaction of PCSK9 with LDLR in contrast to the control inhibitor anti-PCSK9 antibody (5 nM), which targets the LDLR binding region of PCSK9 (BPS Bioscience 71207). In the binding assay the chemiluminescent signal from biotinylated PCSK9 bound to immobilized LDLR is quantified and results are here shown normalized with respect to signal from samples without inhibitor. Bar graphs show average values (n=3) with standard deviation error bars. Results were evaluated using student's t-test. *****p<0.00001.Y-axis: % if no inhibitor. (B) Dose dependent effect of heparin on PCSK9 in the medium as measured by ELISA (n=3). Y-axis: PCSK9 in media (%); (C) Quantitative analysis of mRNA levels in cell lysates by RT-PCR.

The increase in cellular LDLR in heparin-treated HepG2 cells was dose dependent and accompanied by a marked increase in PCSK9 in the medium (FIG. 6B). The PCSK9 concentration was measured using Human (DPC900) Quantikine ELISA kit from R&D Systems according to manufacturer's protocol.

The increase in cellular LDLR and extracellular PCSK9 induced by heparin occurred at the post translational level as we observed no change in mRNA, except for PCSK9 at the highest heparin concentration (FIG. 6C).

RNA extraction from HepG2 cells was performed using NucleoSpin RNA preparation kit (Macherey-Nagel), following cDNA synthesis from 0.5 µg RNA template by iScript™ cDNA synthesis kit (BIORAD). Real time PCR was performed with iQ SYBR® Green supermix and iTaq™ polymerase using the following primers to detect transcripts of LDLR (forward primer 5'ACGGCGTCTCTTCC-TATGACA3', reverse primer 5'CCCTTGGTATCCGCAACAGA3'), PCSK9 (forward primer 5'CCTGGAGCGGATTAC-CCCT3', reverse primer 5'CTGTATGCTGGTGTCTAGGAGA3'), AND GAPDH (forward primer 5'ACAACTTTGGTATCGTGGAAGG3', reverse primer 5'GCCATCACGCCACA-GTTTC3').

We found that 25 U/ml heparin effectively antagonized PCSK9 activity as evident from approximately 2.5-fold increase in LDLR (FIG. 8B) despite the two-fold increase in PCSK9 mRNA.

HepG2 cells incubated 24 h with heparin (50 U/ml) showed increased levels of LDLR as evaluated by Western blotting (FIG. 5A). LDLR levels were also quantified by densitometry (n=4) (FIG. 5B). Incubation with heparin also resulted in increased PCSK9 levels in the medium as measured by ELISA (FIG. 5C).

Heparin does not interfere with the direct interaction between PCSK9 and LDLR as analysed by a PCSK9/LDLR binding assay (FIG. 6 A) (BPS Bioscience) according to the manufacturer's protocol. Briefly, microtiter plate wells coated with LDLR extracellular domain were incubated with biotinylated PCSK9 in the presence of heparin (5 or 50 U/ml) or anti-PCSK9 antibody raised against the LDLR binding domain of PCSK9 (BPS Bioscience #71207). Following washing, wells were incubated with horse radish peroxidase (HRP) labeled-streptavidin and binding of PCSK9 to the LDLR extracellular domain was assessed by addition of HRP substrate and evaluation of signal using a chemiluminescence microplate reader.

The interaction between PCSK9 and LDLR was unaffected by addition of heparin indicate that binding of heparin to PCSK9 results in reduced LDLR degradation by preventing the interaction of PCSK9 with cell surface HSPGs.

Figure 7:
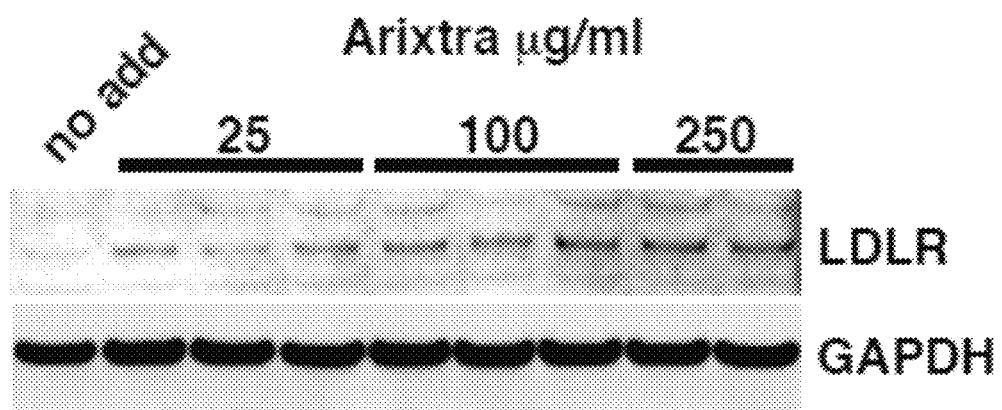
FIG. 7: HepG2 cells incubated for 24 hours with increasing concentration (0-250 µg/ml) of the heparin analogue Arixtra (Fondaparinux, GlaxoSmithKline Pharma) have elevated level of LDLR. GAPDH Western Blot is shown as loading control.

HepG2 cells incubated 24 h with Fondaparinux (Arixtra) (25, 100 or 250 µg/ml) showed increased levels of LDLR as evaluated by Western blotting (FIG. 7). These results indicate that binding of a heparin analogue such as Fondaparinux to PCSK9 results in reduced LDLR degradation by preventing the interaction of PCSK9 with cell surface HSPGs.

Example 6: Heparin Mimetics Prevent PCSK9:LDLR Interaction

Figure 9:
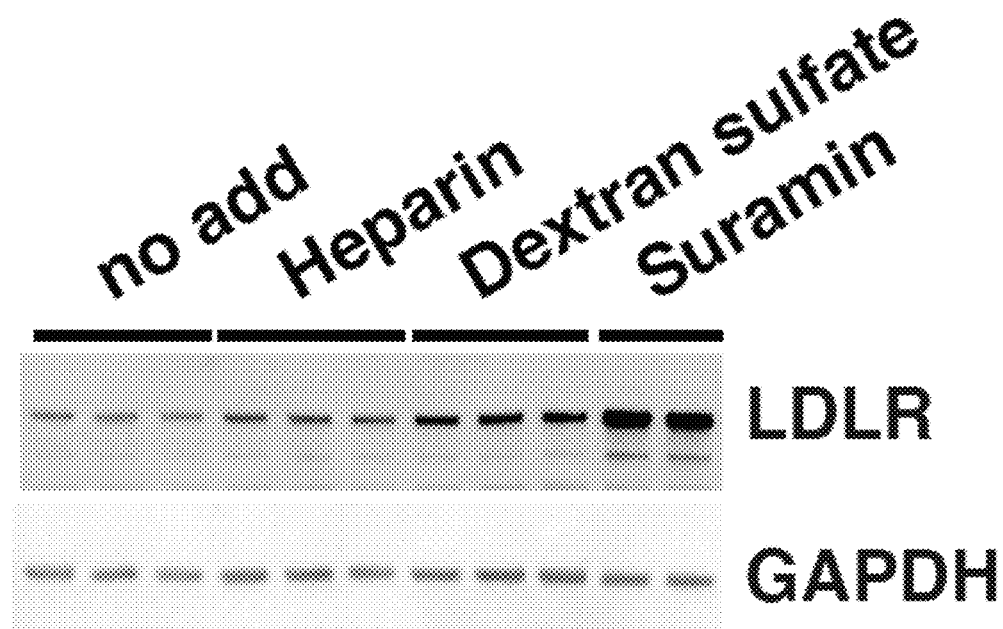
FIG. 9: (A) Western Blot of LDLR in HepG2 cells following 24 hour incubation with heparin mimetics dextran sulphate (200 μg/ml), showing that this compound can potently increase the cellular level of LDLR. For comparison is shown heparin (50 U/ml). GAPDH is shown as loading control. (B) Densitometric quantification of LDLR levels showing concentration dependent increases of LDLR in HepG2 cells after incubation with dextran sulphate (0-200 μg/ml). Bar graphs show LDLR average in % of untreated cells with SEM error bars. (C) Microscale thermophoresis (MST) binding curve for PCSK9 and dextran sulfate. Y axis: fluorescence signal. X axis: dextran sulfate or dextran concentration, $K_D$=180 μM. Circles: dextran sulfate. Squares: dextran. (D) Western Blot, densitometric quantification (E) of LDLR in HepG2 cells following 24 hour incubation with pentosan sulfate (0-200 μg/ml), showing a 4 fold increase in LDLR in lysate from cells treated with 50-200 μg/ml pentosan sulfate. Bar graphs show LDLR average in % of untreated cells with SEM error bars. (F), MST binding curve for PCSK9 and pentosan sulfate Y axis: fluorescence signal. X axis: pentosan sulfate concentration. Circles: pentosan sulfate, $K_D$=381 μM. Squares: control. (G), Quantification of LDLR in HepG2 cells following 24 hour incubation with suramin (0-200 μg/ml). Bar graphs show LDLR average in % of untreated cells with SEM error bars. Representative Western blot of LDLR in suramin-incubated HepG2 cells is shown in (A). (H): MST binding curve for PCSK9 and suramin. Y axis: fluorescence signal. X axis suramin concentration. Circles: suramin, $K_D$=190 μM. Squares: control. (I) Western Blot, and densitometric quantification (J) of LDLR in HepG2 cells following 24 hour incubation with phosphorothioateoligonucleotide S-dC-36 (0-5.0 μM), showing a concentration dependent increase in cellular receptor levels. Bar graphs show LDLR average in % of untreated cells with SEM error bars. Results were evaluated using student's t-test. *p<0.05, p<0.01, *p<0.001, ****p<0.0001. (K) MST binding curve for PCSK9 and S-dC-36. Y axis: fluorescence signal. X axis S-dC-36 concentration. Circles: S-dC-36, $K_D$=4.8 μM. Squares: control.
Figure 9:
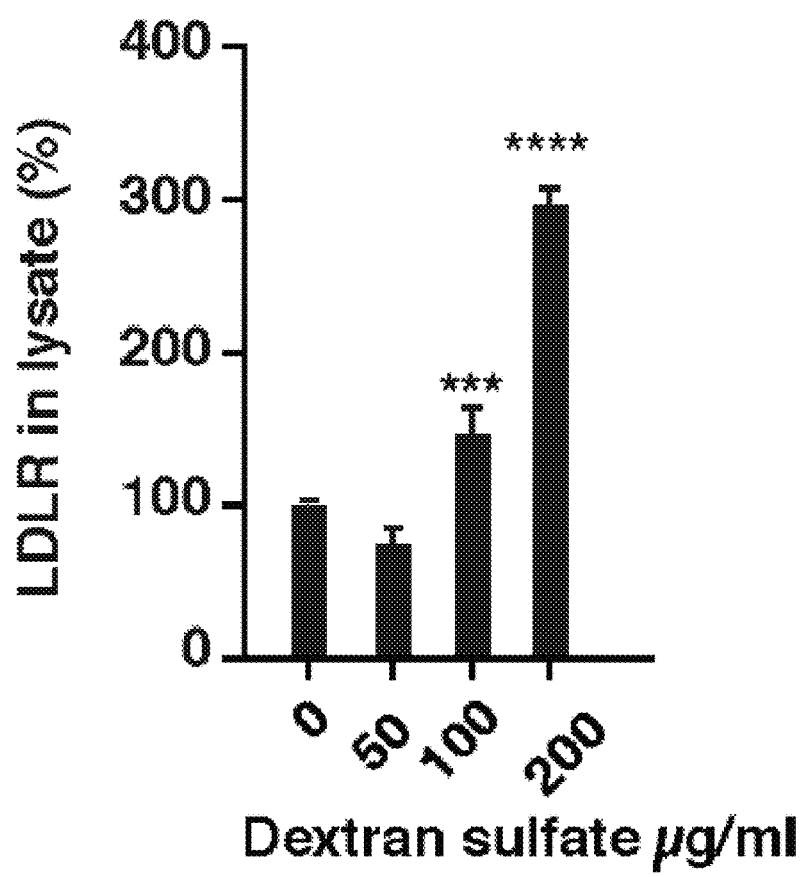
Figure 9:
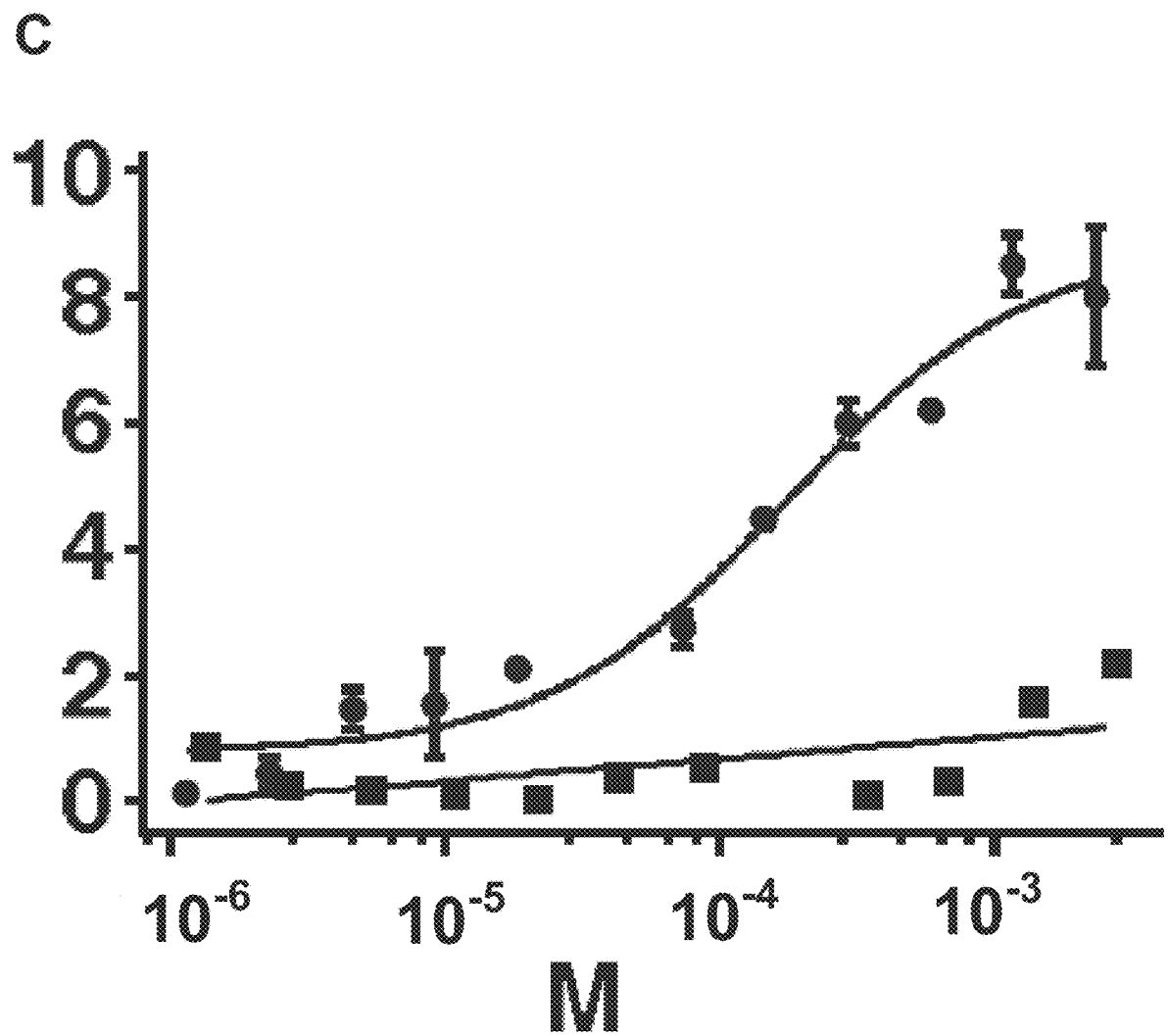
Figure 9:
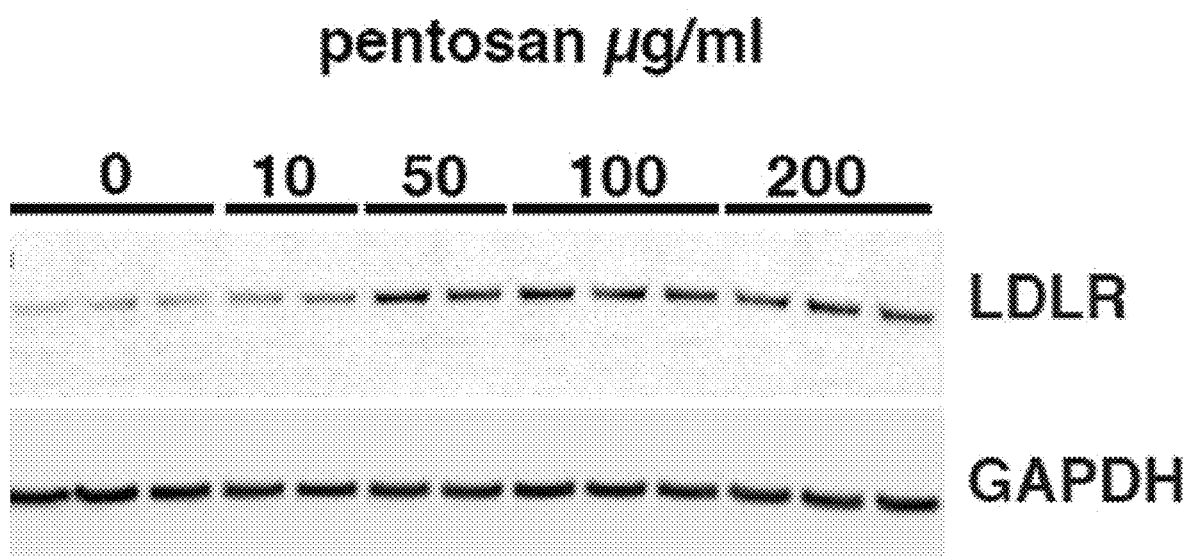
Figure 9:
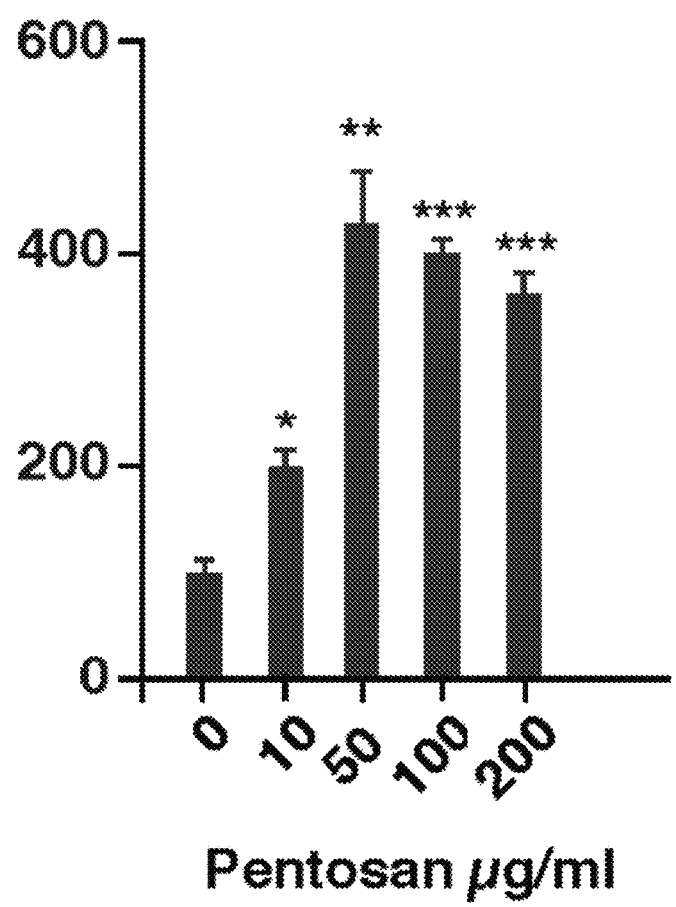
Figure 9:
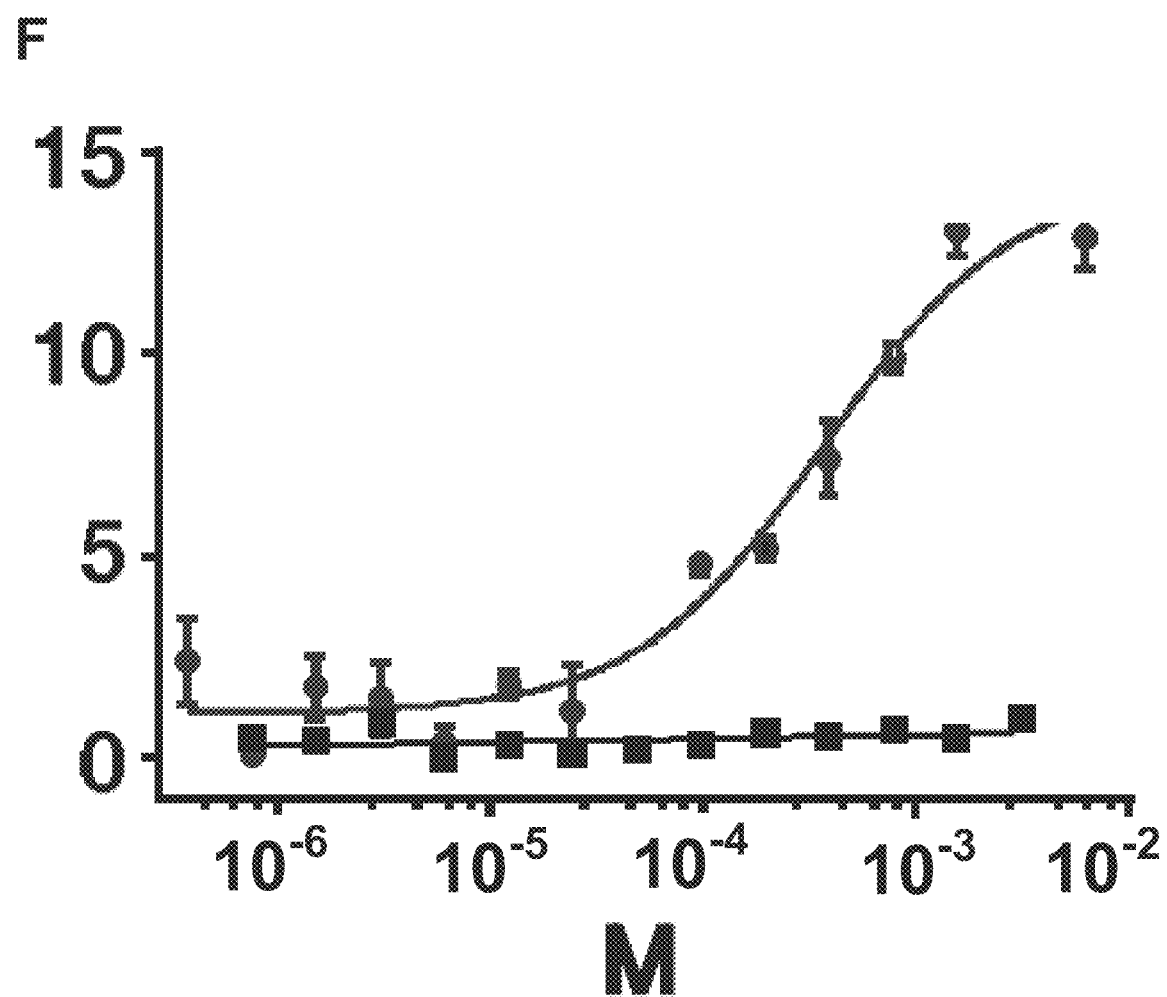
Figure 9:
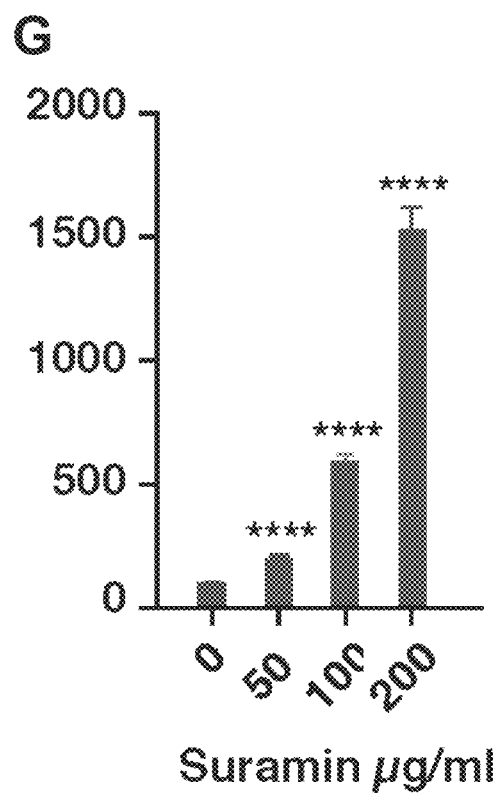
Figure 9:
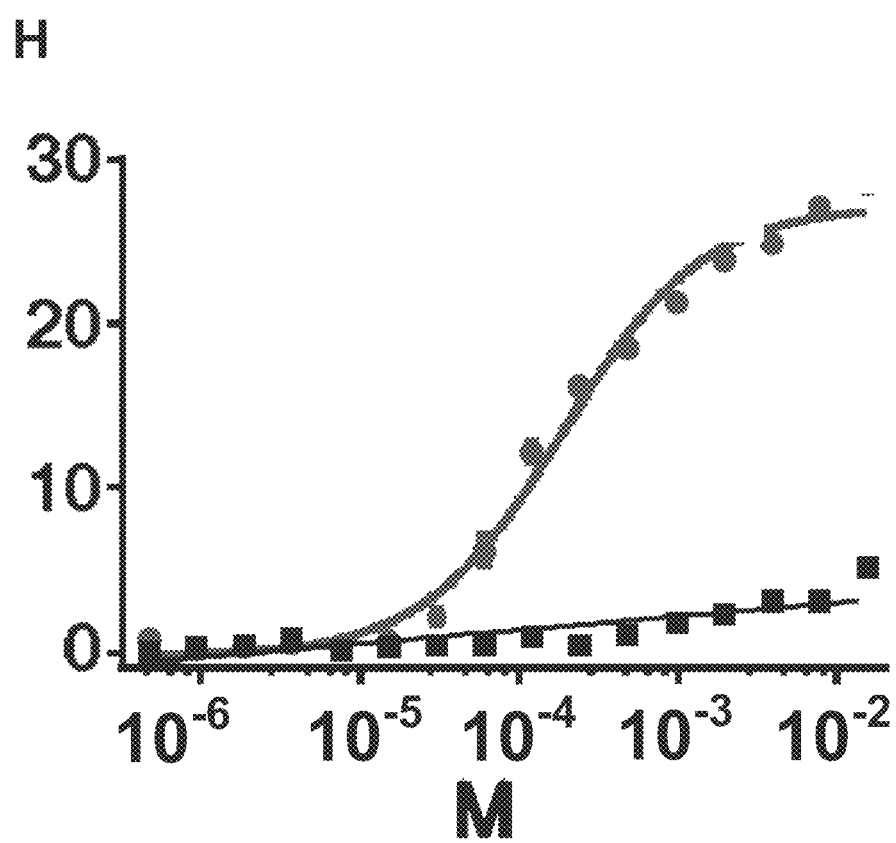
Figure 9:
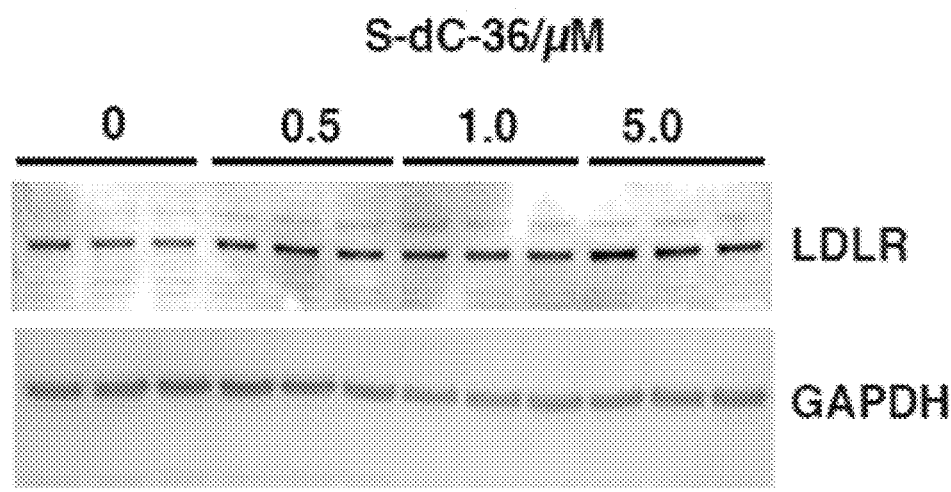
Figure 9:
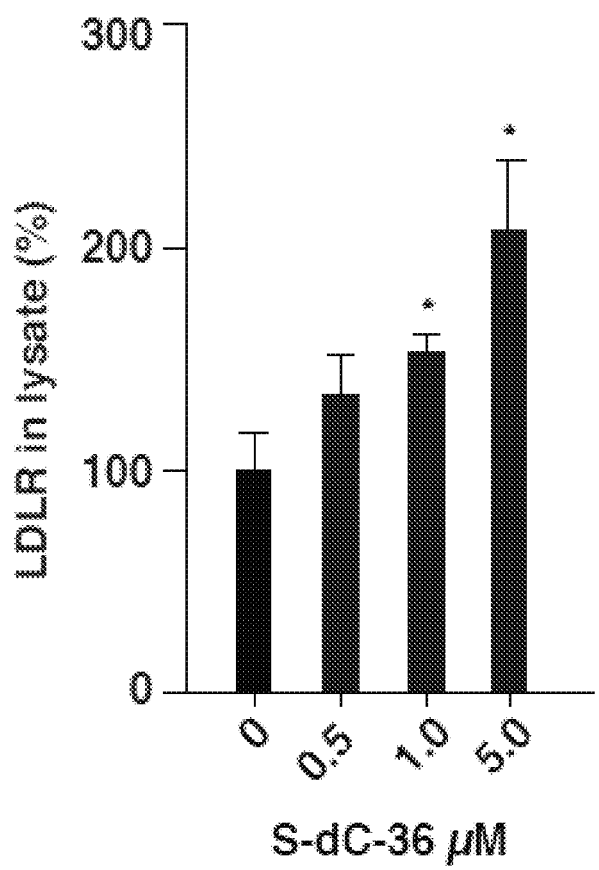
Figure 9:
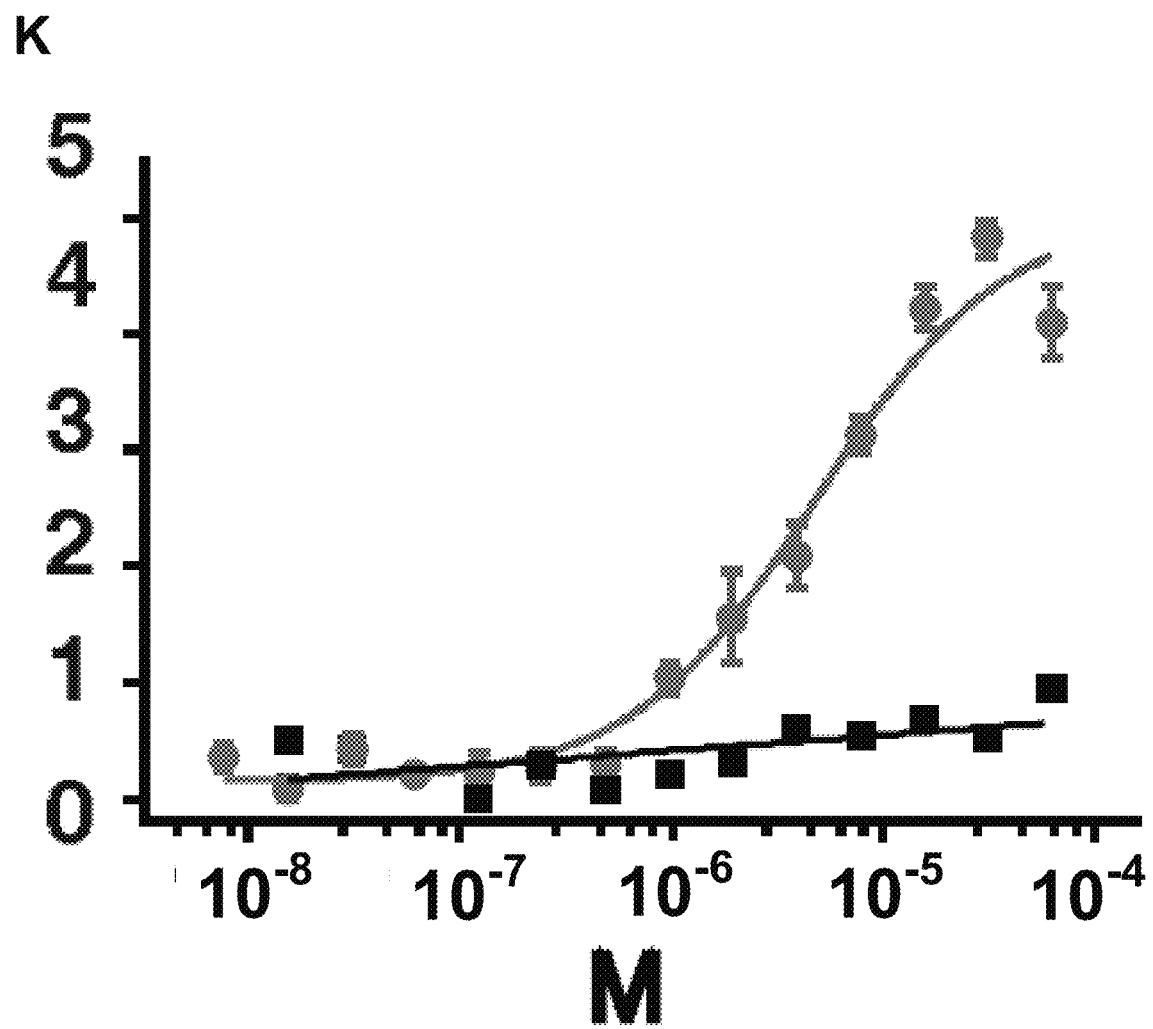

Several molecules mimicking the structure of heparin have been developed over the last 100 years for a number of therapeutic applications, seven of which are currently in clinical use. These are denoted heparin mimetics and belong to diverse chemical classes, including various oligosaccharides, oligonucleotides and naphthalene derivatives. We tested a subset of heparin mimetics for their ability to bind PCSK9 and increase LDLR in HepG2 cells (FIG. 9).

Equilibrium binding affinities between PCSK9 and ligands (suramin, dextran sulfate 5000, dextran 5000, pentosan sulfate and S-dC-36) were assessed using Microscale Thermophoresis (MST) (Jerabek-Willemsen et al., 2011). PCSK9 was labeled using the MO-L003 Monolith Blue-NHS labeling kit (NanoTemper Technologies) and a labeling efficiency of 1:1 molar ratio of protein to dye was achieved. PCSK9 was applied at a final concentration of 100 nM. The unlabeled binding partner was titrated in 1:1 dilutions (in PBS+0.05% Tween-20) where the highest concentrations were 15.4 mM for suramin, 2.3 mM for dextran sulfate 5000, 2.3 mM for dextran 5000, 16.3 mM for pentosan sulfate and 250 µM for S-dC-36. MST measurements were performed in standard-treated capillaries (NanoTemper Technologies) on a Monolith NT.115 instrument (NanoTemper Technologies) using 20% LED and 80% MST power. Laser on and off times were 5 s and 35 s, respectively. Negative controls were performed using 100 nM of labelled PCSK9 in MST buffer in all 16 capillaries under the same conditions as mentioned above. Binding curves were obtained from the temperature-jump phase at 80% MST power for suramin, dextran sulfate 5000 and S-dC-36; and from the thermophoresis+temperature-jump phase at 80% MST power for pentosan sulfate. For each binding partner, the sigmoidal dose-response curves were fitted with GraphPad Prism 6 to yield an average KD value. As fluorescence quenching of PCSK9 was observed in the presence of high concentrations of suramin, a denaturation test was performed by pre-treating PCSK9 with 10% SDS and then heating the samples for 15 min at 90° C. prior to analysis on the MST apparatus. This eliminated the quenching effect, indicating that the fluorescence quenching of PCSK9 under non-denaturing conditions was due to an actual ligand-binding event.

Figure 12:
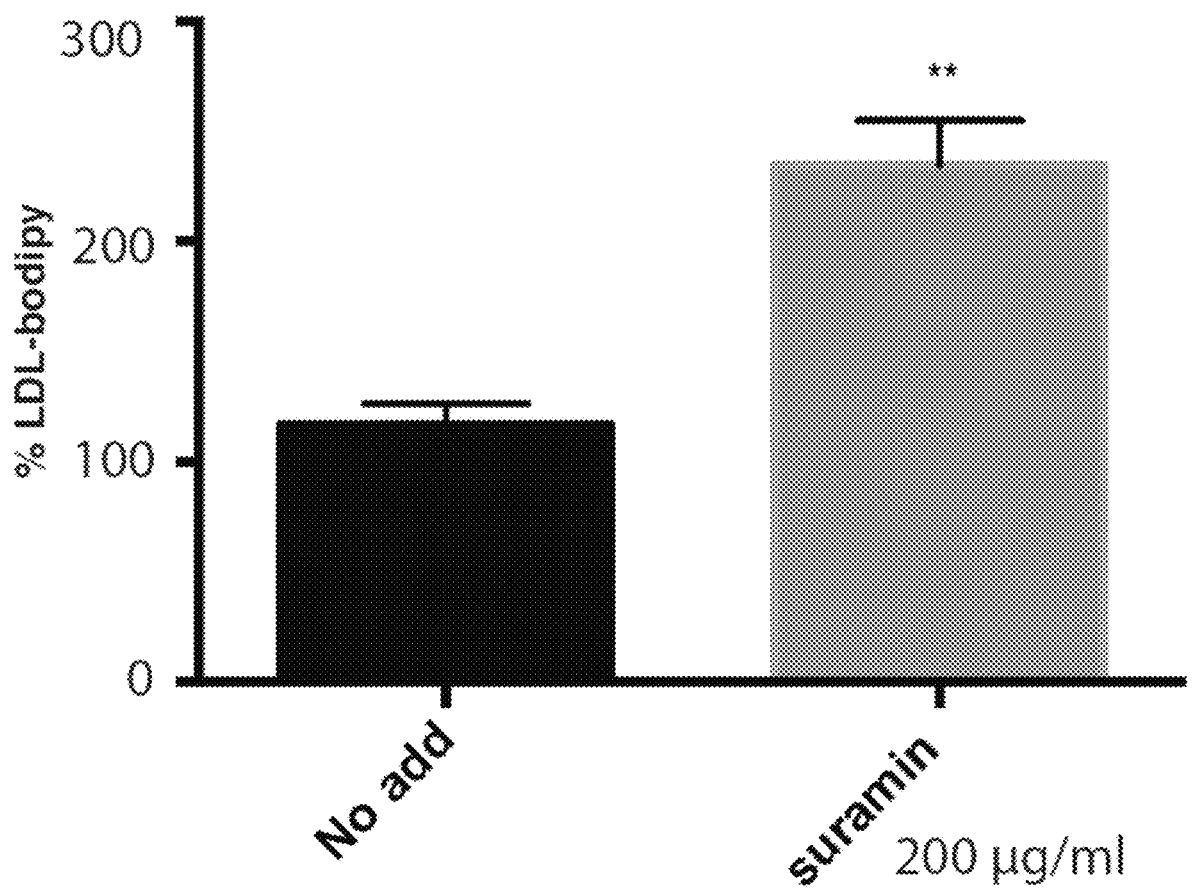
FIG. 12: Bar graphs showing the relative fluorescence signal in HepG2 cells after overnight incubation with suramin (200 μg/ml) following 4 hours incubation with 10 ng/ml LDL particles labeled with fluorescence dye Bodipy. Inhibition of PCSK9 with suramin increases the uptake of LDL two-fold.
Figure 13:
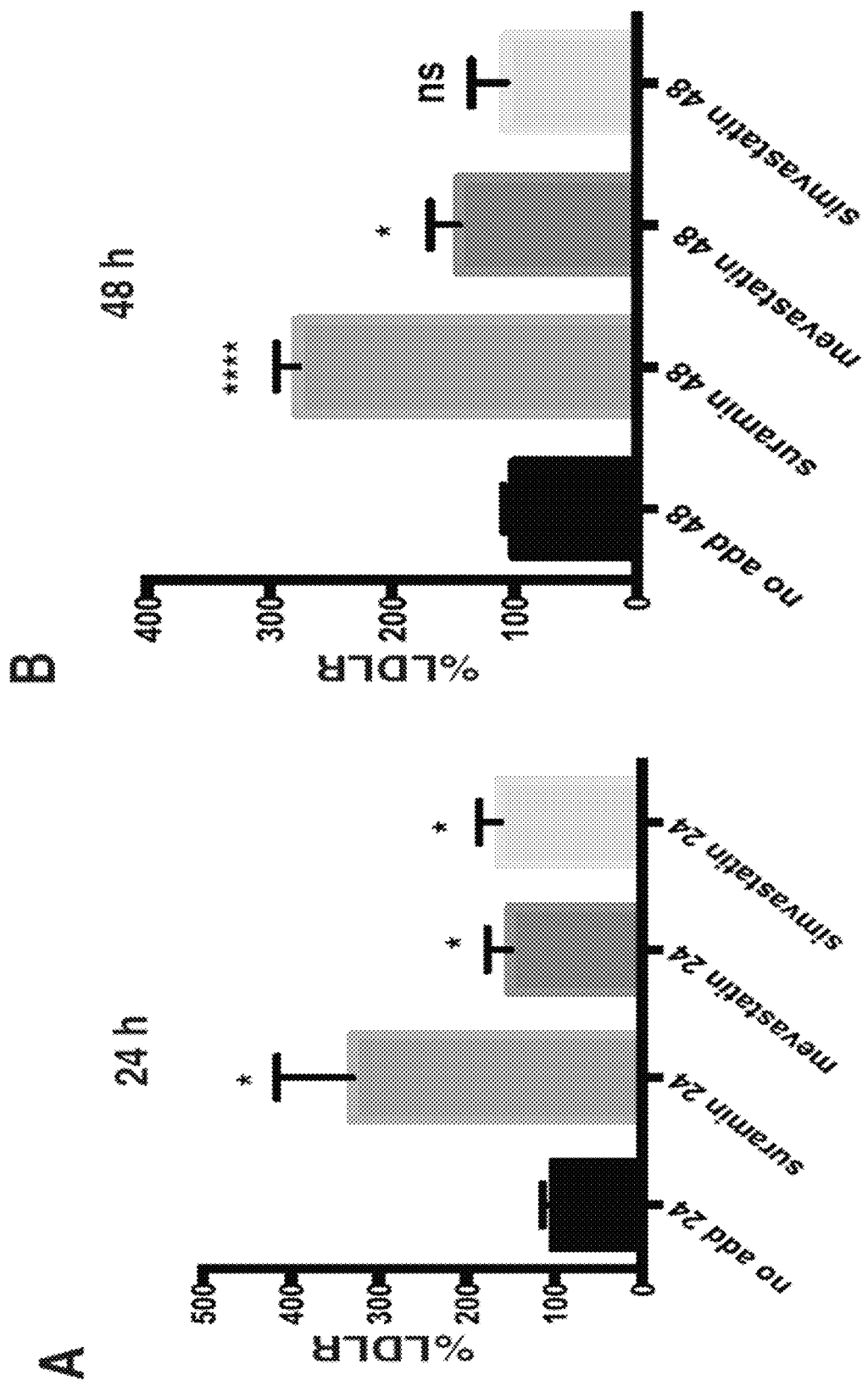
FIG. 13: (A) and (B) Bar graphs showing LDLR levels, as assessed by Western Blot, in HepG2 cells following 24 and 48 hours of incubation with 100 μM suramin or HMG CoA reductase inhibitors mevastatin and simvastatin. Cells incubated with suramin display a higher level of LDLR that cells incubated with statins.

The sulfated oligosaccharides dextran sulfate (FIG. 9C) and pentosan sulfate (FIG. 9F) both bound directly to PCSK9 as determined using MST with an affinity of 179.5 µM and 381.3 µM, respectively, and resulted in dose-dependent increase in cellular LDLR (FIG. 9A-B and FIG. 9D-E), reaching a plateau of around 400% compared to control, and markedly superior to the maximal effect of statins in this assay. The interaction was dependent on the presence of sulfate groups as non-sulfated dextran showed no affinity for PCSK9. The sulfated naphthalene derivative suramin, an antiparasitic drug in African sleeping sickness, binds PCSK9 with an affinity of 190 µM (FIG. 9H) resulted in up to fifteen-fold increase in LDLR (FIG. 9A, 9G), accompanied by increased cellular uptake of fluorescently labelled LDL particles (FIG. 12). We further tested a 36-mer single strand DNA molecule (phosphorothioate oligodeoxycytidine, S-dC-36) and found that it bound PCSK9 with a KD of 4.8 µM (FIG. 9K) and showed potent inhibitory effects at this concentration range (FIG. 9I-J).

Example 7: PCSK9 Shows Selectivity for a Specific Sugar Composition and Sulfation Pattern To dissect the specificity and selectivity of the interaction of PCSK9 with negatively charged sugars, we analyzed PCSK9 binding to a glycan microarray consisting of immobilized synthetic extracellular matrix glycans including defined chain length and sulfation patterns of heparin (FIG. 14 A) and the related glycosaminoglycans keratan sulfate and dermatan sulfate.

The extracellular matrix glycan microarray including synthetic oligosaccharides of heparan sulfate/heparin, keratan sulfate, dermatan sulfate and 5 kDa natural heparin (Santa Cruz) were prepared as described previously using 250 μM spotting solution (Hecht et al., 2009; de Paz et al., 2006). After spotting, the microarray slides were incubated overnight in a humid chamber, followed by three washing steps with water and quenching with 50 mM ethanolamine solution, pH 9, for 1 h at 50° C. to remove the remaining reactive groups. Slides were washed three times with water, blocked at room temperature for 1 h with 1% (w/v) BSA in PBS, pH 7.4 and dried by centrifugation (5 min, 300×g). PCSK9 (25 μg/ml) were incubated overnight at 4° C. diluted in 1% (w/v) BSA-PBS in a humid chamber. After three washing steps with 0.1% (v/v) Tween-PBS, an incubation with preincubated 0.1 μg/ml humanized anti-PCSK9 mAb and 5 μg/ml goat anti-human IgG Alexa Fluor 647 (Life Technologies) diluted in 1% BSA-PBS was performed for 1 h at room temperature. Slides were washed three times with 0.1% (v/v) Tween-PBS, rinsed once with water and dried by centrifugation. For data acquisition slides were scanned with GenePix 4300 microarray scanner (Molecular Devices, Sunnyvale, Ca, USA) by exciting Alexa Fluor 647 at 635 nm. Photomultiplier value (PMT) values were set to reveal scans free of saturation. Median fluorescence values were determined with GenePix Pro 7 software (Molecular Devices).

Figure 14:
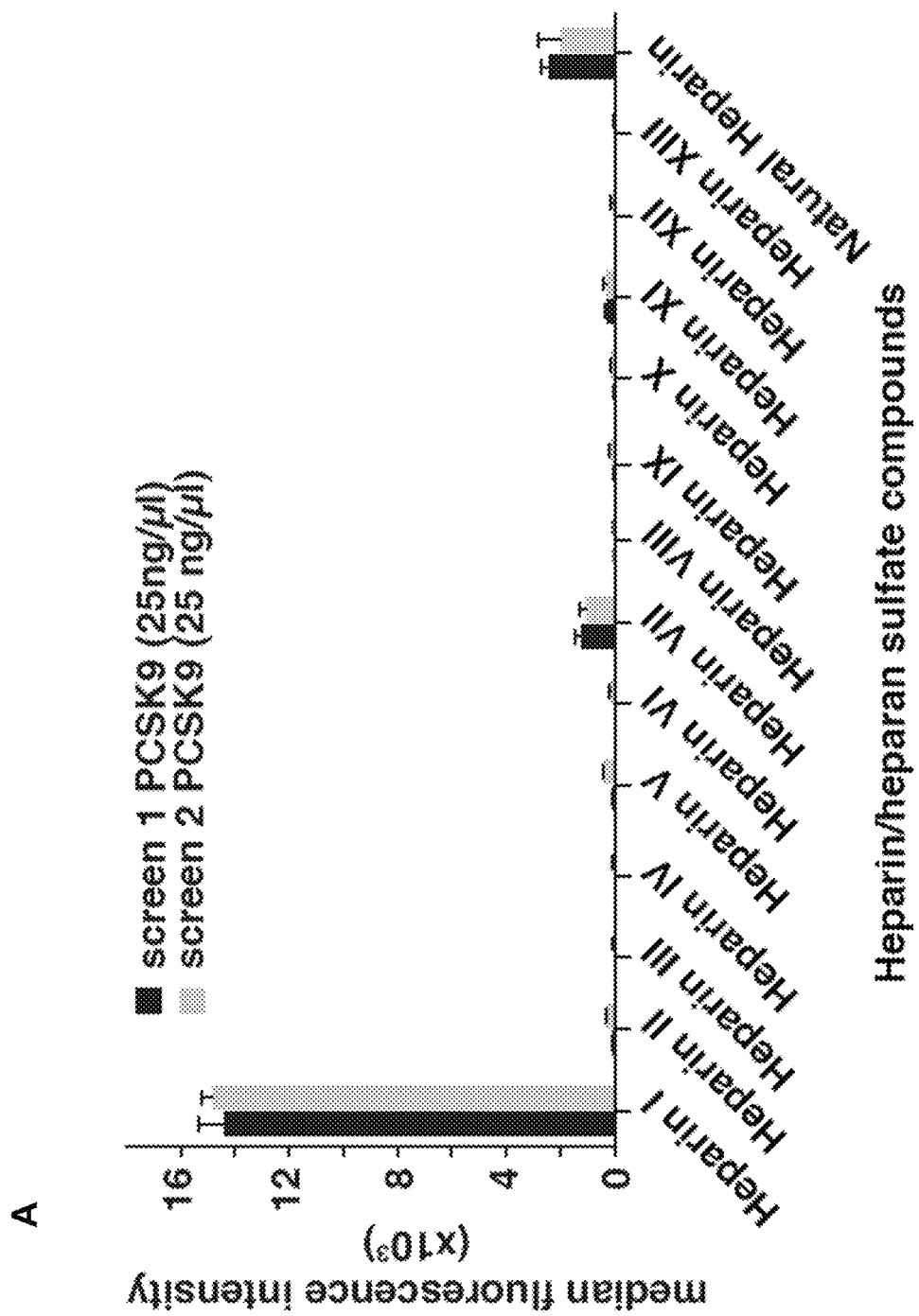
FIG. 14: (A) Dissection of the interaction between PCSK9 and extracellular matrix glycans using a synthetic glycan microarray. Only binding to the different heparin fragments is shown. Natural heparin is included as a positive control. (B) The heparin substructures used in the glycan microarray are shown. Structures interacting with PCSK9 contain repeats of [4)-α-GlcN-6,N-disulfate(1→4)-α-IdoA-2-sulfate-(1-].
Figure 14:
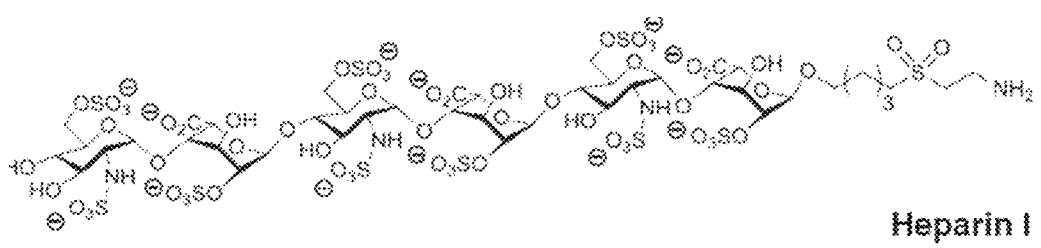
Figure 14:
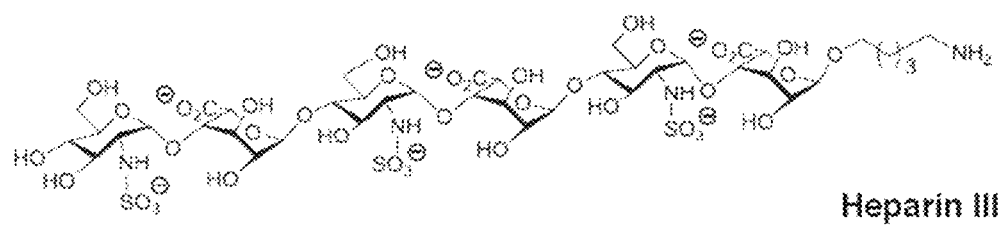
Figure 14:
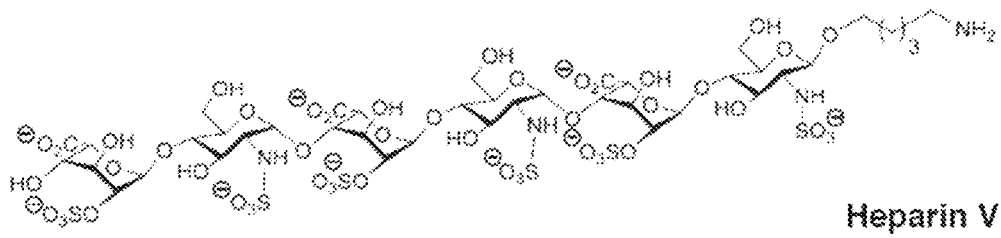
Figure 14:
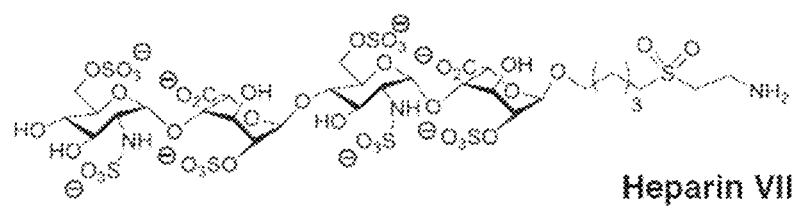
Figure 14:
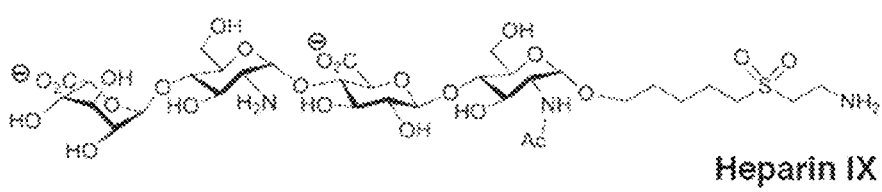
Figure 14:
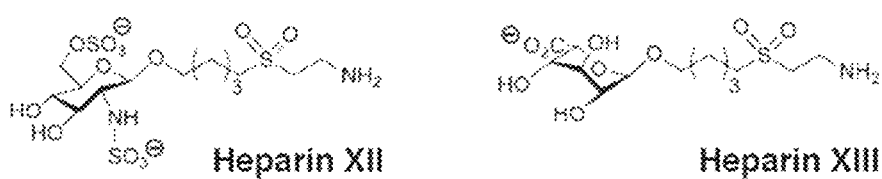
Figure 14:
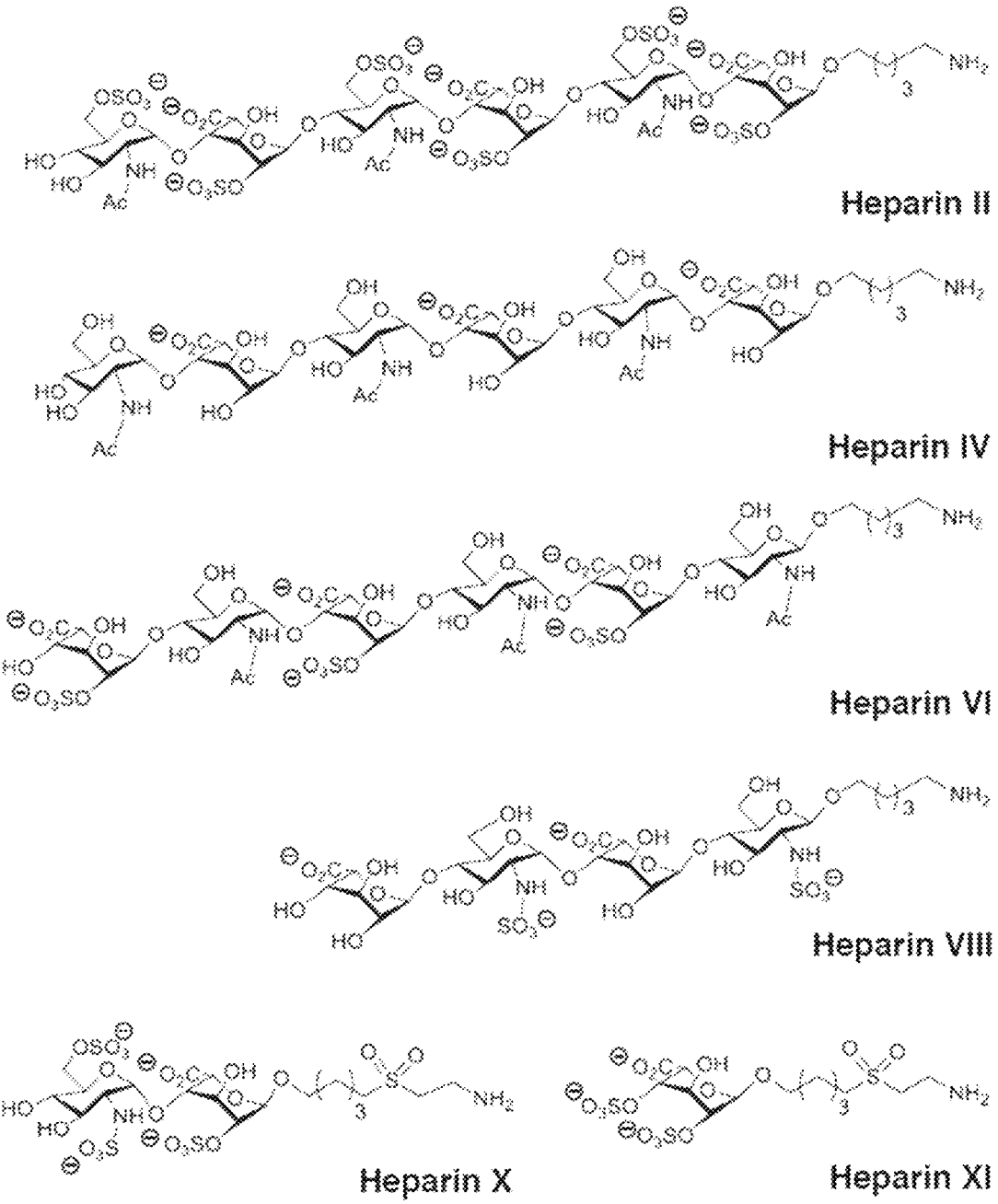
Figure 15:
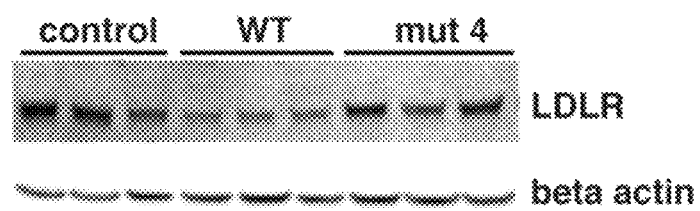
FIG. 15: (A) PCSK9 with mutated HSPG binding site (R93R96R97R104R105H139, mut 4) (10 μg) is ineffective in inducing liver LDLR degradation (n=3 of each) upon injection in mice. Quantification of Western blot shown in (B). (C) PCSK9 but not PCSK9 mut 4 significantly increases total cholesterol in mice fed Western-type diet (control n=25, PCSK9 n=12, PCSK9 mut 4 n=9). (D) Injected PCSK9 mut 4 remained in circulation at higher concentrations compared to PCSK9 WT in line with reduced capture by HSPG and clearance by LDLR.
Figure 15:
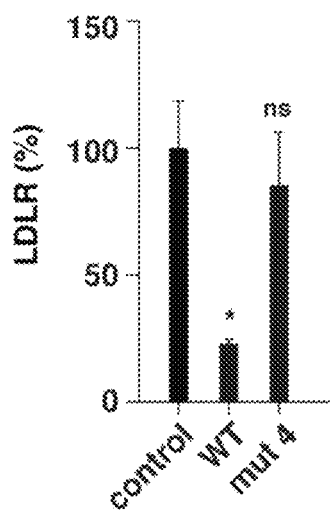
Figure 15:
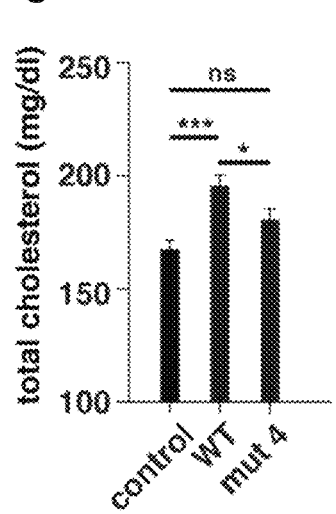
Figure 15:
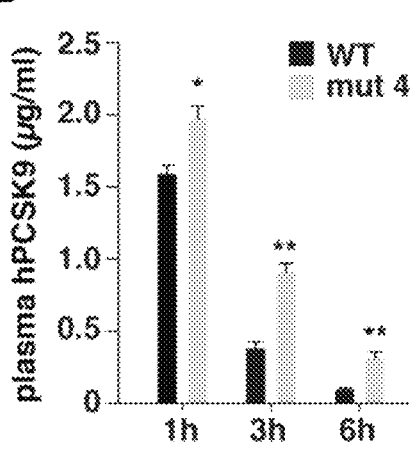

PCSK9 showed selectivity for heparin disaccharide repeats consisting of [4)-α-GlcN-6,N-disulfate(1→4)-α-IdoA-2-sulfate-(1→] as evident from the binding of the heparan sulfate/heparin substructures I and VII encompassing three and two repeats, respectively (FIG. 14 B). A minimum of two repeats was required for efficient binding as no binding was observed for heparan sulfate/heparin substructure consisting of only one repeat. The requirement of sulfate groups at the amino group of GlcN and of ester-linked sulfate groups at carbon 6 of GlcN and at carbon 2 of IdoA was also apparent by comparing the binding to heparan sulfate/heparin substructures Heparin I, Heparin II and Heparin III.

These results demonstrated the preference of PCSK9 for a specific sugar composition and sulfation pattern (FIG. 14 B).

Example 8: Therapeutic Preparations of Low-Molecular Weight Heparins Protect LDLR Against PCSK9 Induced Degradation HepG2 cells incubated overnight with the low-molecular weight heparin preparation fragmin (1-100 U/ml) or Innohep (1-100 U/ml) showed increased levels of LDLR as evaluated by Western blotting (FIG. 8A). The effect of fragmin and Innohep were comparable to the effect of heparin (FIG. 5A) and the pentasaccharide Arixtra (FIG. 7).

These results show that structure-based drug design using the heparin:PCKS9 complex as a template is a feasible approach in the development of a small molecule PCSK9 inhibitor.

Example 9: Heparin Protects the LDLR Against PCSK9 Induced Degradation In Vivo

Mice (BALB6/cJRj) were subjected to a single intravenous administration (tail vein) of 10 μg human recombinant PCSK9 alone or in combination with heparin (50 U). One hour post injection mice were sacrificed and liver tissues were collected. Western blot analysis of LDLR in membrane protein preparations showed a significant higher level of liver LDLR in mice co-injected with heparin compared to mice injected with PCSK9 alone (FIG. 8B, quantified in FIG. 8C).

These results show that the PCSK9:heparin interaction may provide a framework for the development of small molecule PCSK9 inhibitors.

Example 10: Reducing LDL Cholesterol in a Patient not Responding to Statin Treatment A patient with elevated LDL cholesterol is prescribed a statin treatment. The patient does not respond to the statin treatment. The patient is then prescribed a treatment with subcutaneous injections of 25-500 mg of a composition comprising a heparin analogue that is designed to block the HSPG binding site in human PCSK9. The injections take place at intervals of 1-28 days. Marked reductions in LDL-C levels are observed, showing that parenteral administration of a heparin analogue can lead to reduction in LDL-C levels in a patient non-responsive to statin treatment.

Example 11: Reducing LDL Cholesterol Using a Heparin Analogue Directed Against the HSPG Binding Site of PCSK9

A patient with elevated LDL cholesterol levels is prescribed administration of a heparin analogue that is designed to block the HSPG binding site in human PCSK9. The compound is administered orally at a dosis of 0.1-30 mg/kg. Marked reductions in LDL-C levels are observed, showing that oral administration of a heparin analogue designed to block the HSPG binding site in human PCSK9 can lead to reduction in LDL-C levels in a patient.

Example 12: Reducing LDL Cholesterol in a Patient not Responding to Statin Treatment A patient receives statin treatment against elevated LDL-C levels. However, after an initial drop in LDL-C levels, and due to the statin-induced increased expression of PCSK9, the treatment does not succeed in significantly reducing LDL-C levels.

In addition to the statin, the patient is administered a compound inhibiting binding of HSPGs to PCSK9. The administration occurs weekly and with a low dose (25-150 mg) of the compound in combination with statins. Marked reductions in LDL-C levels are observed, and the desired level of LDL-C is reached.

This example shows that supplementing a statin-based treatment with administration of a heparin analogue can successfully reduce LDL-C levels.

Example 13: PCSK9 with Mutated HSPG Binding Site Fails to Increase LDL Cholesterol Levels Wild-type PCSK9 and HSPG-binding mutants of PCSK9 are over-expressed in mouse livers by hydrodynamic tail injection of expression plasmids free of CG dinucleotides (Invivogen); these plasmids exhibit long term expression as compared to conventional plasmids that are prone to inactivation by methylation of CG base pairs. Over-expression of wild-type PCSK9 induces enhanced degradation of LDLR, resulting in elevated serum LDL cholesterol and thereby behaving as a "gain of function" variant. The HSPG mutants of PCSK9 behave as "loss of function" variants giving rise to less elevated serum LDL cholesterol levels due to reduced degradation of the LDL receptor.

The results demonstrate the pivotal role of the PCSK9 HSPG-binding domain for the degradation of the LDL receptor in animals.

Example 14: Structure-Based Drug Design of Small Molecule PCSK9 Inhibitors Based on the Interaction of PCSK9 with Heparin and Heparin Mimetics Candidate compounds selected among low molecular weight heparins and heparin analogues are tested for their ability to inhibit PCSK9 function and increase LDLR levels in a HepG2 cell culture assay. The heparin analogue fondaparinux (trade name Arixtra) is used as the reference compound. The structural information obtained is used to derive 3-5 pharmacophore models, which are used to screen an existing database of 3 million purchasable compounds. A diversity-based collection of 50 compounds is selected for functional testing in HepG2 cells. Successful inhibitors facilitate calibration of the molecular docking model and a second screening of purchasable compounds. Fifty compounds are selected for purchase and in vitro testing. The three most promising candidates are subsequently tested in a mouse model to evaluate in vivo effect on LDLR levels in the liver and cholesterol in plasma.

Example 15: Testing of PCSK9 Inhibitor Candidates

Preclinical testing of PCSK9 inhibitor candidates is performed using a coronary artery disease mouse model heterozygote for LDLR (LDLR+/−) with expression of human PCSK9 under control of the endogenous murine PCSK9 promoter. Western type diet fed animals is treated with PCSK9 inhibitors for a time period of 6-8 months, before evaluation of atherosclerotic plaque area by microscopy after oil red O staining of fat deposits in dissected aorta. The plasma concentration of cholesterol is assessed by ELISA every second month during the experiment.

These studies will allow evaluation of the ability of PCSK9 inhibitor candidates to lower serum cholesterol.

Example 16: Dextran Sulphate and Pentosan Protect LDLR from PCSK9-Induced Degradation In the heparin mimetic class of modified polysaccharides compounds dextran sulfate (FIG. 9 A-B) and pentosan (FIG. 9 D-E) were tested in a HepG2 based in vitro cell assay. After overnight incubation LDLR levels were evaluated by Western blotting showing a concentration dependent increase of LDLR upon treatment with dextran sulfate (0-200 µg/ml) with up to 3-fold up regulation of LDLR. Pentosan (0-200 µg/ml) incubation resulted in 4 fold increase LDLR at concentrations from 50 µg/ml.

Example 17: Effect on Pentosan on Liver LDLR Levels

Pentosan-polysulfate is injected into mice expressing human PCSK9 to evaluate the ability of the substance to protect the LDLR against PCSK9 induced degradation.

These studies will confirm that administration of pentosan leads to increased LDLR levels in vivo.

Example 18: Effect of Pentosan on Serum Cholesterol Levels

Patients with elevated serum cholesterol are treated with oral or subcutaneous injection of Pentosan-polysulfate to evaluate the ability of the substance to lower serum cholesterol. Pentosan-polysulfate is absorbed from the digestive tract with a median of 2 hours after ingestion of an oral dose according to the manufacturer. Cholesterol levels are then measured.

These studies will confirm that pentosan leads to decreased serum cholesterol levels.

Example 19: PCSK9 Inhibitory Effect of Innohep Fractions

Figure 18:
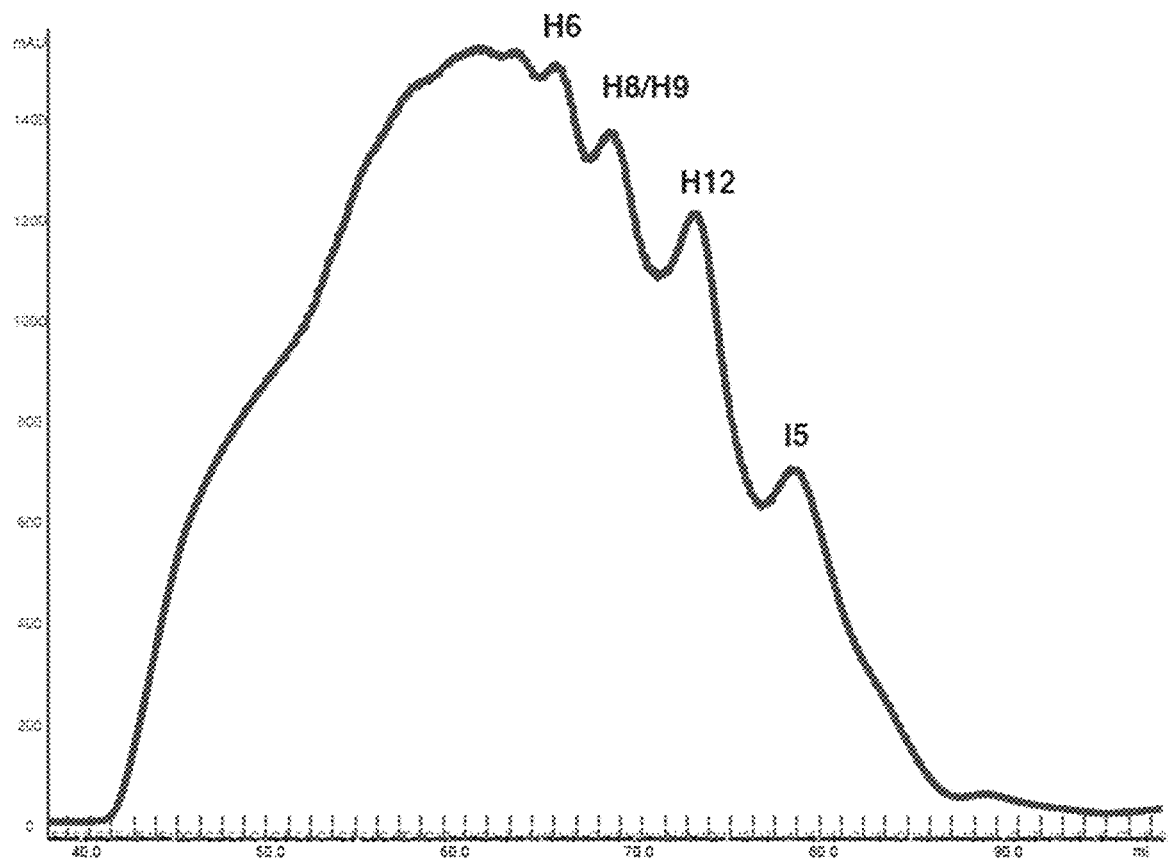
FIG. 18: (A) Elution profile obtained by size-exclusion chromatography of Innohep. PCSK9 inhibitory activity of indicated fractions were subsequently tested in HepG2 cells (B) Western blot showing LDLR levels in HepG2 cells incubated with size-exclusion fractions (20 µM). Over night incubation with fraction H6 increased the cellular LDLR 5-fold, and this fraction was further fractionated using strong anion exchange (SAX) chromatography (FIG. 19).
Figure 18:
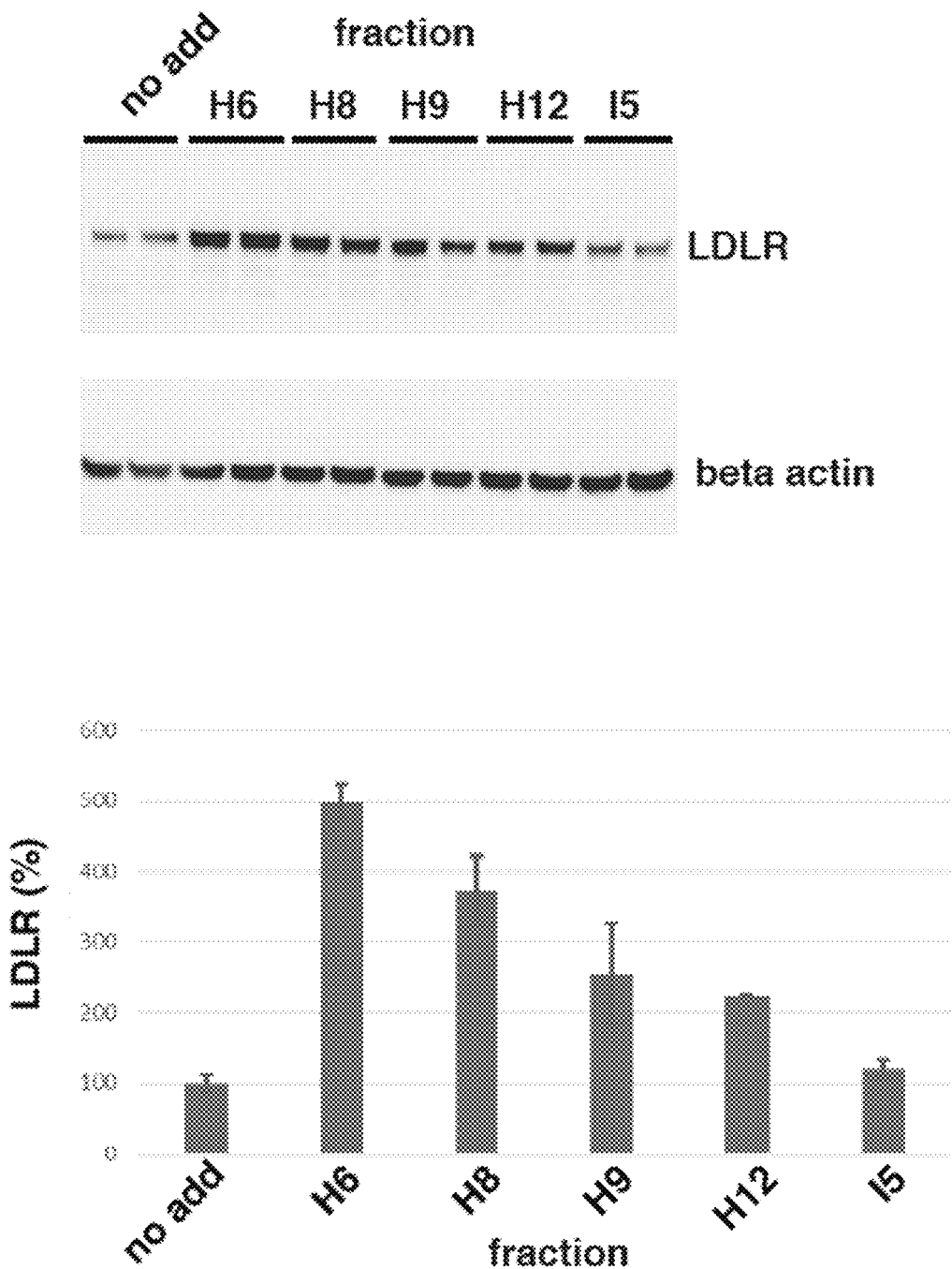
Figure 19:
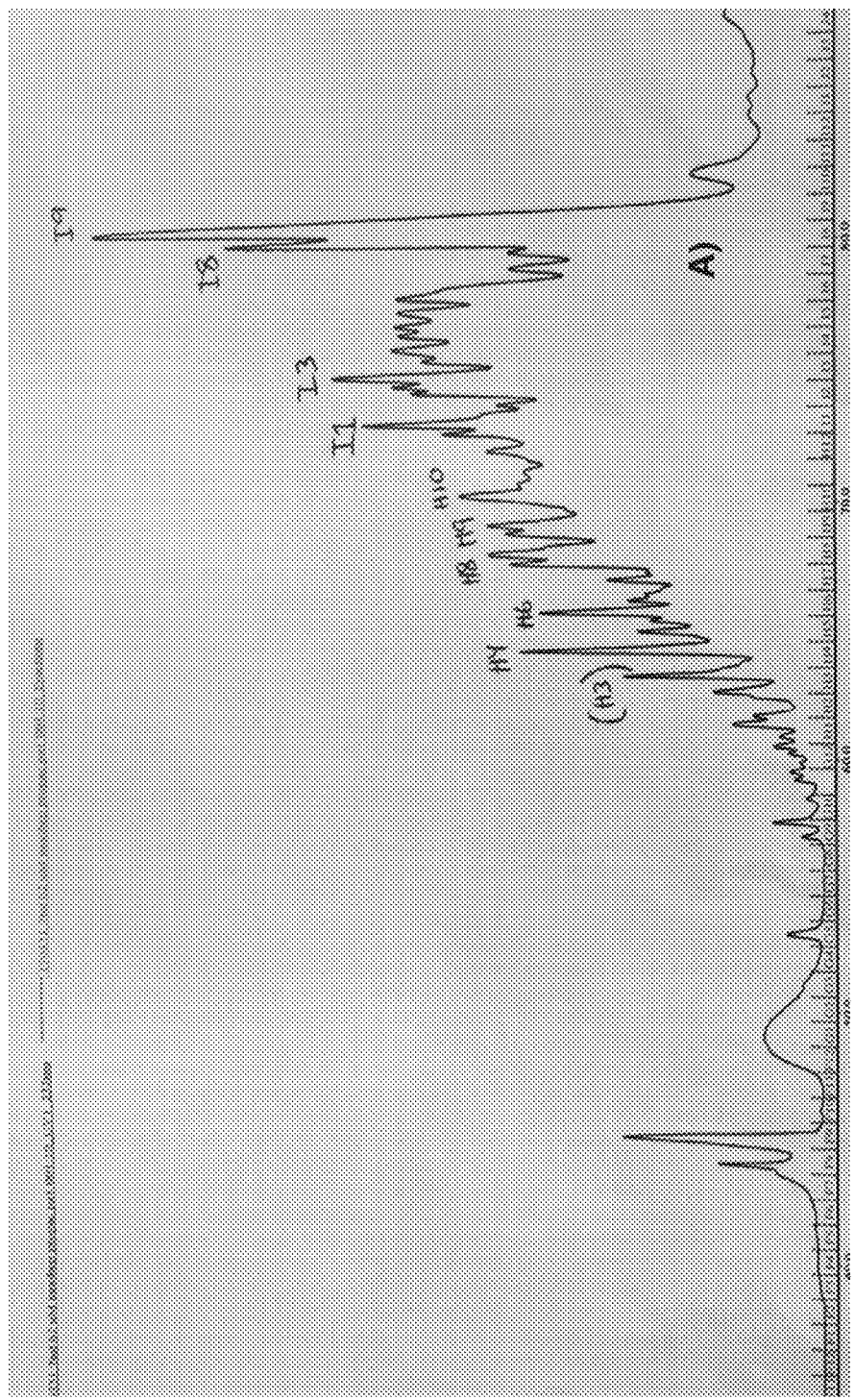
FIG. 19: (A) Elution profile obtained by strong anion exchange (SAX) chromatography of Innohep fraction H6. (B) Western blot of LDLR in HepG2 incubated over night with selected SAX fractions. SAX fraction 11, 18 and 19 contain heparin fragments with PCSK9 inhibitory activity and increase LDLR levels up to 2-fold at the tested concentration (500 nM).
Figure 19:
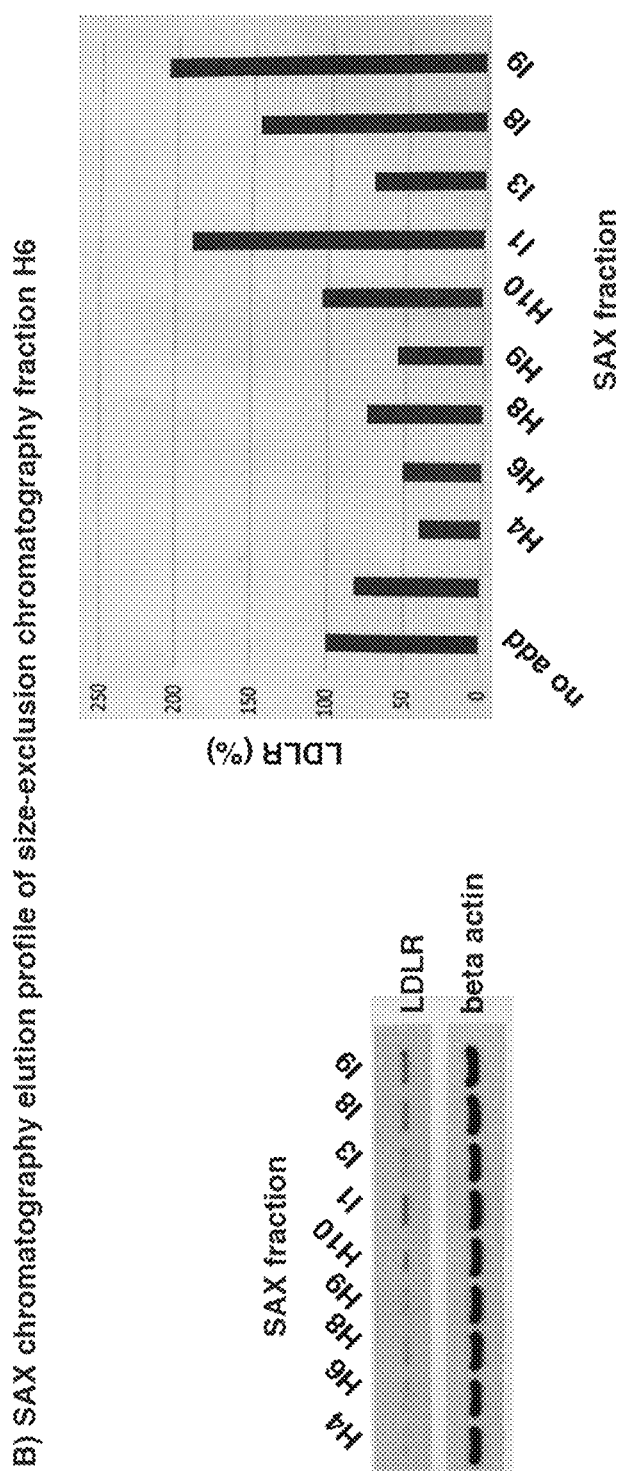

Innohep (Low molecular weight heparin) contains heparin fragments ranging in size from 5000 to 8000 Da, and is a potent inhibitor of PCSK9 activity. To further identify the PCSK9 inhibitory fragments, Innohep was fractionated by size-exclusion chromatography (FIG. 18 A). Obtained fractions were tested in a HepG2 cell-based assay for their ability to inhibit PCSK9 and increase cellular level of LDLR (FIG. 18 B). In this assay, a number of fractions were found to increase the LDLR level (2-5 fold) after over night incubation with saccharide concentration 20 µM. Highest LDLR level was obtained with size-exclusion fraction H6, which subsequently was subjected to strong anion exchange (SAX) chromatography (FIG. 19 A). HepG2 cells were incubated with obtained SAX fractions (500 nM), and LDLR levels were evaluated (FIG. 19 B). SAX fraction 11, 18 and 19 contain heparin fragments with PCSK9 inhibitory activity and increase LDLR levels up to 2-fold at the tested concentration (500 nM).

Figure 20:
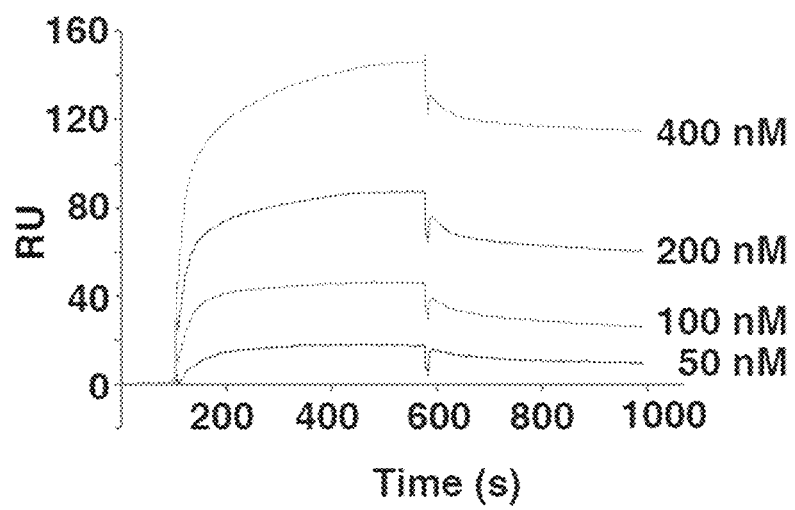
FIG. 20: BIACORE analysis of PCSK9 binding to heparin-albumin. The analysis used sensor chips coupled with either heparin-albumin (Sigma H0403) or albumin (Sigma A4503). (A) Binding of PCSK9 to heparin-albumin. (B) Binding of PCSK9 to albumin. PCSK9 bound to heparin-albumin with an affinity constant of 700 µM, no binding was observed to the sensor chip coupled with albumin. An interference assay was implemented to assess the binding between PCSK9 and compound (X). (C) PCSK9 preincubated with increasing concentrations of compound (X) infused over the sensor chip coupled with heparin-albumin. The binding curves revealed that compound (X) inhibits binding of PCSK9 to the heparin-albumin sensor chip with an estimated IC50 of 50 nM.
Figure 20:
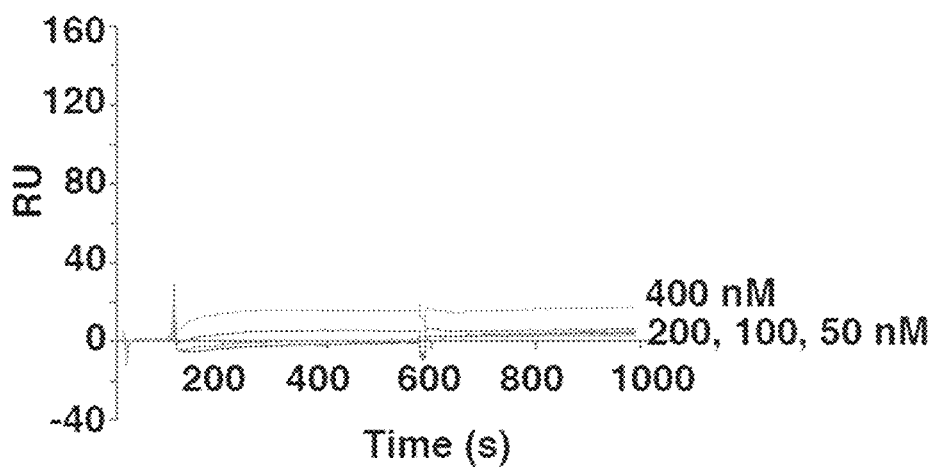
Figure 20:
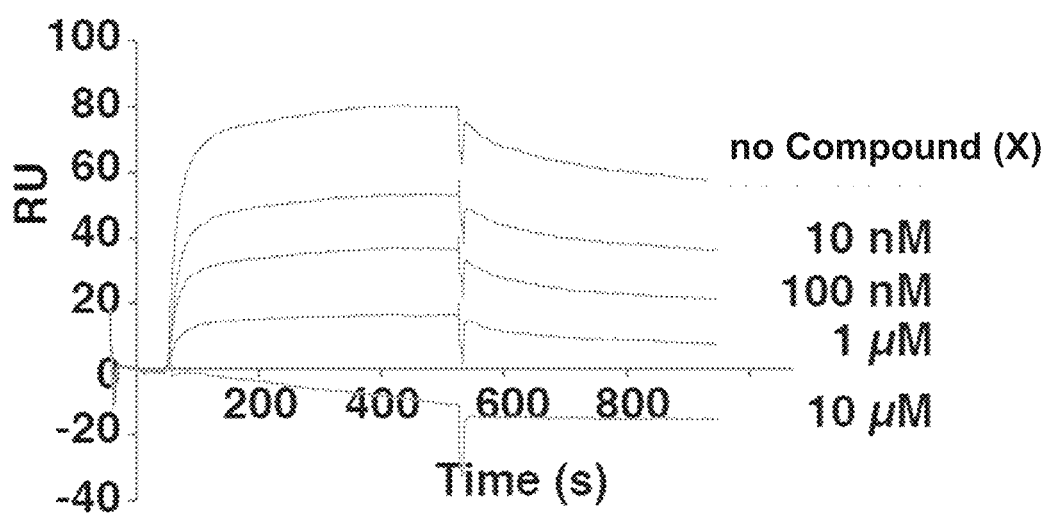

Example 20: Compound (X) Inhibits Binding of PCSK9 to Heparin in Biacore Assay BIACORE analysis using sensor chips coupled with either albumin (Sigma A4503) or heparin-albumin (Sigma H0403) were used to evaluate the interaction between PCSK9 and heparin. The analysis revealed that PCSK9 bound to albumin-heparin with an affinity constant of 700 pM (FIG. 20 A), no binding was observed to the control sensor chip coupled with albumin (FIG. 20 B). An interference assay using BIACORE analysis was implemented to assess the binding between compound (X) and PCSK9. Solutions of 100 nM PCSK9 was incubated with increasing concentrations of compound (X) (0 nM, 10 nM, 100 nM, 1 µM and 10 µM), the solutions were then infused over the sensor chip coupled with heparin-albumin. The binding curves revealed that compound (X) inhibits binding of PCSK9 to the heparin-albumin sensor chip with an estimated IC50 of 50 nM (FIG. 20 C).

Figure 16:
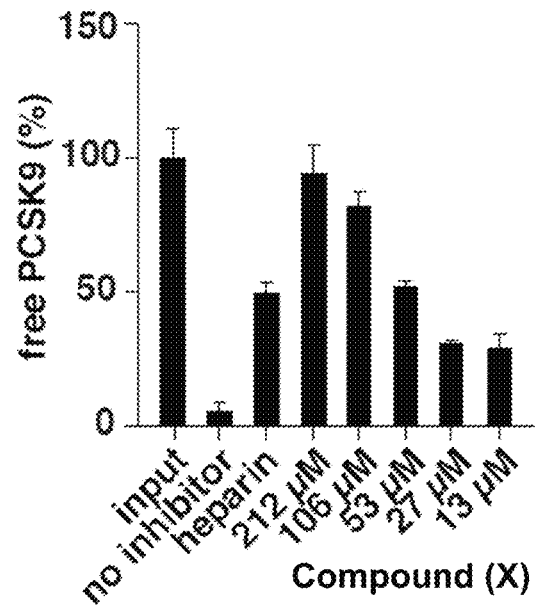
FIG. 16: (A) The ability of compound (X) to inhibit the PCSK9-heparin interaction was tested in an assay, in which PCSK9 (1 μg/ml) was precipitated with heparin-sepharose beads in the presence of inhibitor. Following over night incubation beads were pelleted, and non-precipitated PCSK9 in the supernatant (=free PCSK9) was evaluated by ELISA. Bar graphs show free PCSK9(%) in samples with increasing concentrations of compound (X) as indicated, normalised to the PCSK9 concentration in a sample without heparin-sepharose beads (input control). A negative control sample was incubated without inhibitor, and a positive control sample was incubated with soluble heparin (5 mg/ml). Mean value with SEM is shown (n=2). (B) Representative Western blot of LDLR levels in HepG2 cells incubated over night with compound (X) concentrations as indicated. Bar graphs show quantification of WB (mean value with SEM, n=2). Control cells were incubated without inhibitor (negative control) or with 500 μg heparin/ml (positive control). (C) LDLR levels in liver samples of mice (BALB6/cJRj, males, 10 weeks) injected with PCSK9 inhibitors compound (X) (0.13 mg/kg) or Evolocumab (8 mg/kg) 1 hour prior injection with PCSK9 (0.4 mg/kg). Liver samples were collected 1 hour post PCSK9 injection. Control groups were injected with NaCl (0.9%) before injection of PCSK9 or NaCl. Bar graphs show mean value with SEM. NaCl/NaCl group n=3, NaCl/PCSK9 group n=5, Evolocumab/PCSK9 group n=5, compound (X)/PCSK9 group n=8.
Figure 16:
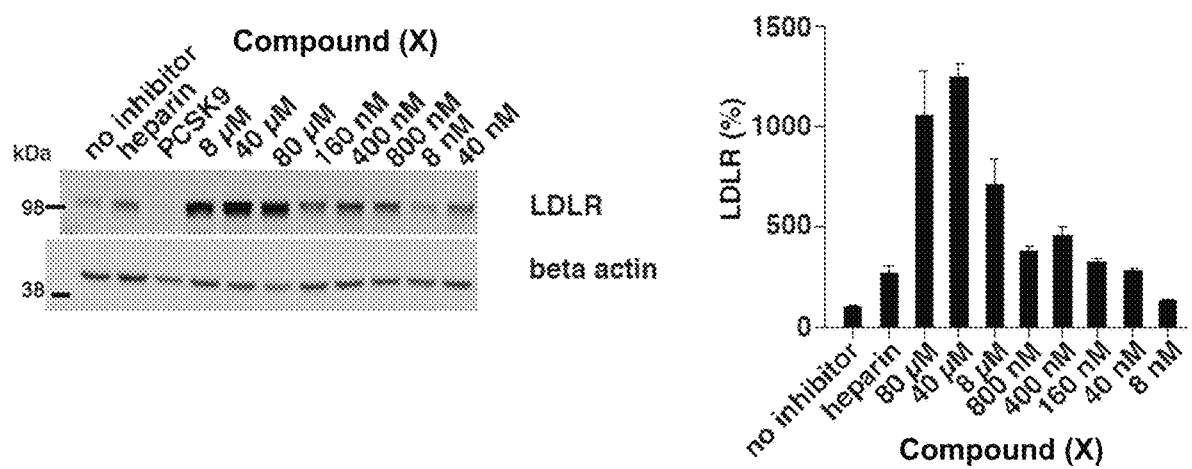
Figure 16:
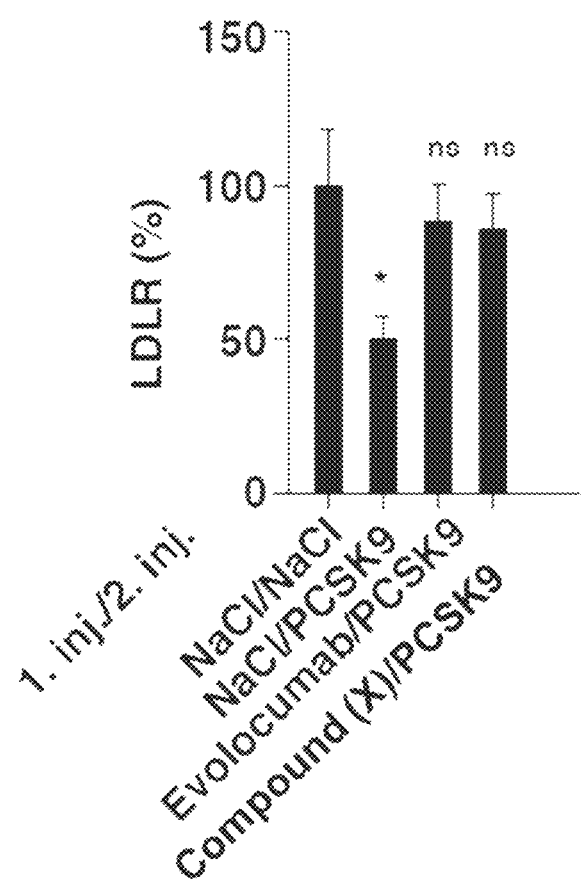

Example 21: Compound (X) Inhibits Binding of PCSK9 to Heparin-Sepharose Beads Compound (X) inhibition of PCSK9 binding to Heparin/Heparan sulfate was tested in a Heparin-sepharose binding assay. Heparin-sepharose beads (2 µl) were incubated with PCSK9 (1 µg/ml) with increasing concentrations of compound (X) (0-500 µg/ml) in a total volume of 150 µl 10 mM $NaH_2PO_4$. After over night rotation at 4° C., beads were pelleted and the concentration of non-precipitated PCSK9 (free PCSK9) in supernatant was evaluated by ELISA. The concentration of free PCSK9 in each sample was normalised to the PCSK9 level in a sample without Heparin-sepharose beads (input control). As positive control was included a sample with soluble heparin (5 mg/ml) (FIG. 16 A). Compound (X) (500-200 µg/ml) completely inhibited PCSK9 interaction with Heparin-sepharose in this assay. For comparison, addition of soluble heparin resulted in 50% inhibition. These results show that compound (X) efficiently inhibits binding of PCSK9 to heparin in vitro.

Example 22: Compound (X) Protects the LDLR Against PCSK9 In Vitro

HepG2 cells incubated 24 h with compound (X) (0-200 µg/ml) showed concentration dependent increased levels of LDLR as evaluated by Western blotting of cell lysates and quantified by densitometry (FIG. 16 B). Control cells were incubated without additives (negative control) or 500 µg/ml heparin (positive control). LDLR levels were calculated with respect to the level found in lysate of HepG2 cells incubated without additives. Compound (X) incubation resulted in up to 12 times higher LDLR levels. For comparison, cells incubated with heparin (500 µg/ml) showed approximately 3 times elevated LDLR.

These experiments show that compound (X) protects LDLR against PCSK9 induced degradation in HepG2 cells.

Example 23: Compound (X) Inhibits PCSK9 Induced Degradation of the LDLR In Vivo Mice (BALB6/cJRj) were subjected to a single intravenous (tail vein) administration of 3.2 µg compound (X) 60 minutes prior injection with PCSK9 (10 µg). PCSK9 induced degradation of liver LDLR was assessed 60 min post PCSK9 injection by Western blotting and quantified by densitometry (FIG. 16 C). Control mice were injected with NaCl or control inhibitor Evolocumab (200 µg), commercially available PCSK9 inhibitory monoclonal antibody (Amgen). LDLR levels were calculated with respect to LDLR level in mice injected with NaCl alone. The LDLR level was decreased 50% in mice injected with PCSK9 without prior injection of inhibitor, whereas no decrease was observed in mice injected with compound (X) (0.13 mg/kg) or Evolocumab (8 mg/kg). These studies show that administration of compound (X) prior PCSK9 injection protects the LDLR as efficiently as Evolocumab at much lower dosage.

Example 24: Effect of Compound (X) on LDL-Cholesterol Clearance in HepG2 Cells HepG2 cells seeded in 96 wells are incubated over night with compound (X) (200 µg/ml). The following day is added LDL-particles (5 µg/ml) labeled with Dil fluorescence dye (Thermo Fisher Scientific) and incubated for 4 h at 37° C. Following washing of cells with PBS, cellular uptake of LDL-particles is evaluated at excitation/emission 552/573 nm. After over night incubation at −80° C., the number of cells/well is quantified using a CyQuant Cell Proliferation Assay (Thermo Fisher Scientific).

These studies will confirm that compound (X) inhibition of PCSK9 activity increases the uptake of LDL-cholesterol in vitro.

Example 25: Effect of Compound (X) on Serum LDL-Cholesterol Levels in Humans Patients with elevated serum LDL-cholesterol levels are treated with a weekly intravenous injection of compound (X) (dosage) for 6 weeks to evaluate the ability of compound (X) as LDL-cholesterol lowering treatment. LDL-cholesterol (HPLC) is measured in blood sampled prior and once a week during treatment.

These studies will confirm that compound (X) lowers serum LDL-cholesterol humans suffering from hypercholesterolemia.

Figure 17:
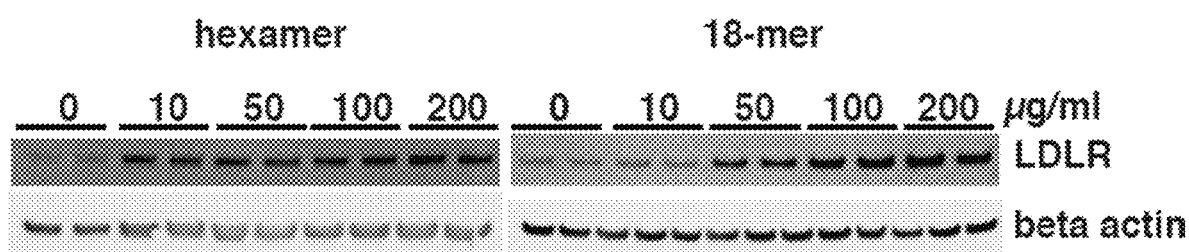
FIG. 17: (A) Western blot of LDLR levels in HepG2 cells incubated over night with heparin hexamer or 18-mer in concentrations as indicated. (B) Bar graphs show quantification of WB (mean value with SEM, n=2).
Figure 17:
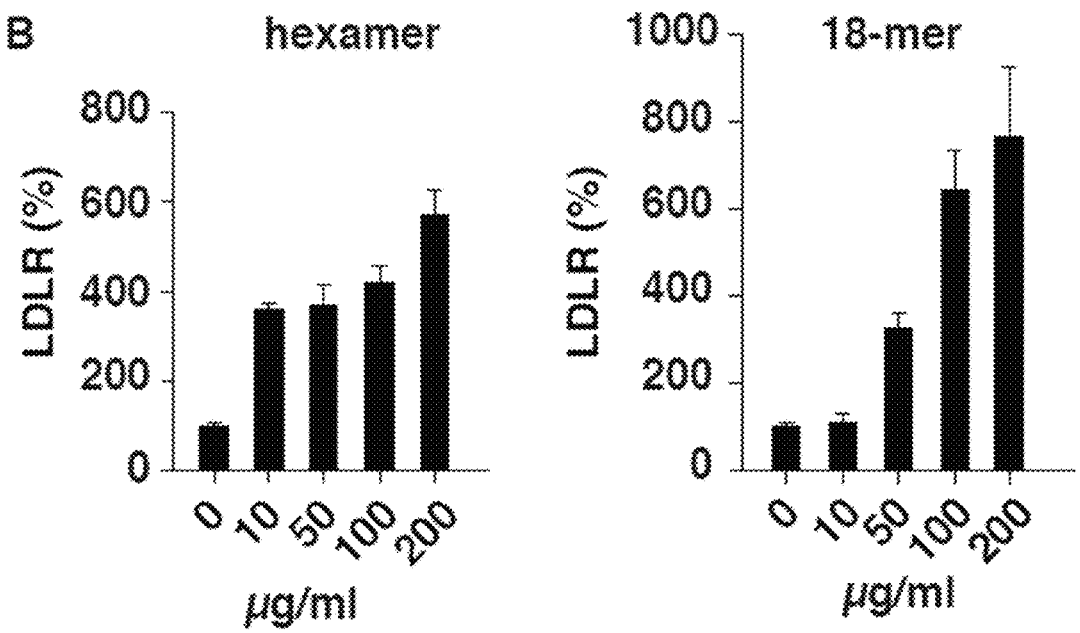

Example 26: Sulfated Hexamer and 18-Mer Heparins Inhibit PCSK9 Function In Vitro HepG2 cells were incubated with 0-200 µg/ml of heterogeneously sulfated hexamer or 18-mer oligosaccharides containing on average 1,3 sulfates per disaccharide. After over night incubation cells were harvested and the cellular level of LDLR was analyzed by Western blotting (FIG. 17 A) and quantified by densitometry (FIG. 17 B). Cells incubated with either of these heparins showed 6-8 fold increased cellular LDLR level compared to control cells at the highest concentration tested (200 µg/ml). Furthermore, the hexamer has potent PCSK9 inhibitory effect at concentrations as low as 10 µg/ml.

Figure 21:
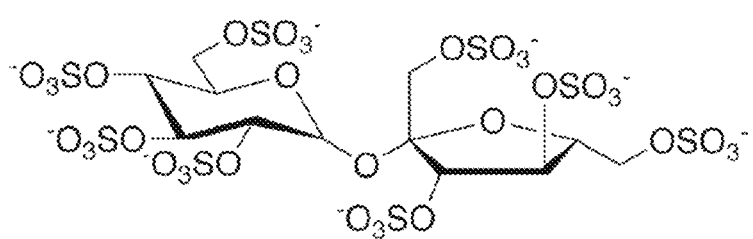
FIG. 21: (A) Structure of sucrose octasulfate (B) Bar graphs show precipitation of PCSK9 by Heparin-sepharose beads in the presence of sucrose octasulfate concentrations as indicated. Percent non-precipitated PCSK9 (free PCSK9) was calculated with respect to the PCSK9 concentration in a sample with out Heparin-sepharose beads (input control). A positive control sample was incubated with soluble heparin (5 mg/ml). Mean value with SEM is shown (n=3-2).
Figure 21:
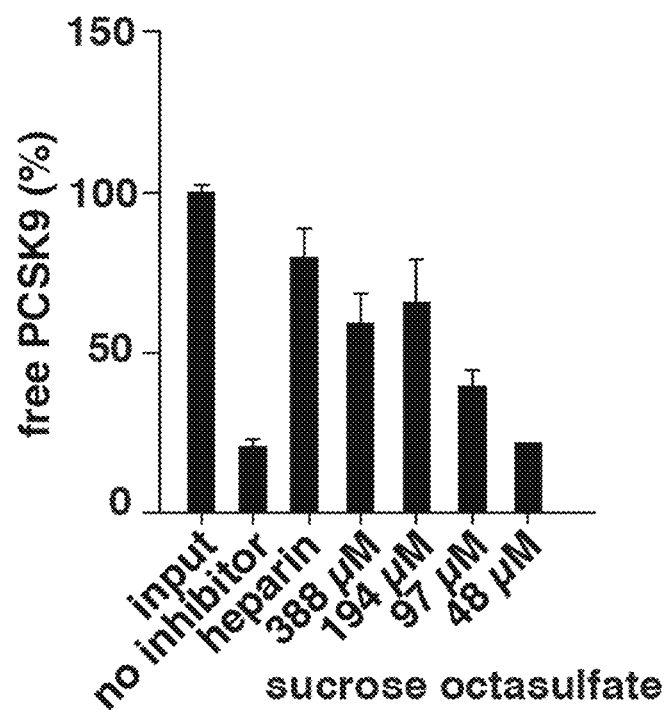

Example 27: Sucrose Octasulfate Inhibits Binding of PCSK9 to Heparin-Sepharose Beads Sucrose octasulfate (FIG. 21A) inhibition of PCSK9 binding to Heparin/Heparan sulfate was tested in a Heparin-sepharose binding assay. Heparin-sepharose beads (2 µl) were incubated with PCSK9 (1 µg/ml) and increasing concentrations of sucrose octasulfate (0-500 µg/ml) in a total volume of 150 µl 10 mM $NaH_2PO_4$. After over night rotation at 4° C., beads were pelleted and the concentration of non-precipitated PCSK9 (free PCSK9) in supernatant was evaluated by ELISA). Percent free PCSK9 was calculated with respect to the PCSK9 concentration in a sample without Heparin-sepharose beads (input control) (FIG. 21B). Sucrose octasulfate at concentrations 500-250 µg/ml inhibited PCSK9 precipitation with Heparin-sepharose as well as 5 mg/ml soluble heparin (positive control) in this assay. These results show that sucrose octasulfate efficiently inhibits binding of PCSK9 to heparin in vitro.

SEQUENCES

```
SEQ ID NO: 1: PCSK9 protein - NCBI accession
number: NG_009061.1
MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

QAARRGYLTKILHVFHGLLPGFLVKMSGDLLELALKLPHVDYIEEDSSVF

AQSIPWNLERITPPRYRADEYQPPDGGSLVEVYLLDTSIQSDHREIEGRV

MVTDFENVPEEDGTRFHRQASKCDSHGTHLAGVVSGRDAGVAKGASMRSL

RVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGT

LGTNFGRCVDLFAPGEDIIGASSDCSTCFVSQSGTSQAAAHVAGIAAMML

SAEPELTLAELRQRLIHFSAKDVINEAWFPEDQRVLTPNLVAALPPSTHG

AGWQLFCRTVWSAHSGPTRMATAVARCAPDEELLSCSSFSRSGKRRGERM

EAQGGKLVCRAHNAFGGEGVYAIARCCLLPQANCSVHTAPPAEASMGTRV

HCHQQGHVLTGCSSHWEVEDLGTHKPPVLRPRGQPNQCVGHREASIHASC

CHAPGLECKVKEHGIPAPQEQVTVACEEGWTLTGCSALPGTSHVLGAYAV

DNTCVVRSRDVSTTGSTSEGAVTAVAICCRSRHLAQASQELQ*
```

REFERENCES

Benimetskaya et al. (1995) Nucleic Acids Res 23: 4239-4245
Bird et al. (1988) Science 242:423-426.
Chan et al. (2009) Proc Natl Acad Sci USA. 2009 Jun. 16; 106(24):9820-5. doi: 10.1073/pnas.0903849106
Cunningham et al. (2007) Nat Struct Mol Biol. 14(5): p. 413-9.
de Paz, J. L., Spillmann, D. & Seeberger, P. H., (2006) Chem Commun (Camb), 3116-8
Fisher et al. (2007) J Biol Chem. 282(28): p. 20502-12.
Greenberg A S, Avila D, Hughes M, Hughes A, McKinney E C, Flajnik. (1995) Nature. 374, 168-173.
Guns et al., 2009. British Journal of Pharmacology (2010), 159, 326-336
Gustafsen et al. (2014) Cell Metab 19(2): p. 310-8
Hamers-Casterman C, Atarhouch T, Muyldermans S, et al. (1993) Nature. 363(6428):446-8.
Hecht, M. L. et al. (2009) J Proteome Res 8, 712-20
Herbert et al., *Circ Res* 79, 590-600 (1996).
Hollinger et al. (1993) Proc. Natl. Acad. Sci. USA 90: 6444-6448.
Huston et al. (1988) Proc. Natl. Acad. Sci. USA 85:5879-5883.
Jerabek-Willemsen et al. (2011) Assay Drug Dev Technol. 9(4): p. 342-53.
Kohler and Milstein (1975) Nature 256:495.
Lagace et al. (2006) J Clin Invest. 2006 November; 116(11): 2995-3005
Lakoski et al. (2009) J Clin Endocrinol Metab. 94(7): p. 2537-43.
Lima et al., Biochim Biophys Acta. 2009 June; 1794(6): 873-81.
Lonberg, N. et al. (1994) Nature 368 (6474):856-859.
Munck Petersen et al (1999) EMBO J 18(3):595-604.
McCoy, A. J., et al., Structure of beta-antithrombin and the effect of glycosylation on antithrombin's heparin affinity and activity. J Mol Biol, 2003. 326(3): p. 823-33.
Nour-Eldin H H, Hansen B G et al. (2006) Nucleic Acids Res. 34(18):e122.
Piper et al. (2007). Structure, 2007. 15(5): p. 545-52.
Reiter Y, Brinkmann U, et al. (1994) J. Biol. Chem. 269 (15):18327-31.
Seidah et al. (2014) Circ Res. 2014 Mar. 14; 114(6):1022-36. doi: 10.1161/CIRCRESAHA. 114.301621
Sheridan (2013). Nat Biotechnol. 2013 December; 31(12): 1057-8. doi: 10.1038/nbt1213-1057.
Soderberg et al., *Nat Methods* 3, 995-1000 (2006).
Stein et al. (1995) Nat Med 1: 1119-1121.
Villiers B R, Stein V, Hollfelder F. (2010) Protein Eng Des Sel. 23(1):1-8.
Walley K. R. et al., Curr Opin Crit Care. 2016 October; 22(5):464-9
Ward E S, Güssow D, Griffiths A D, Jones P T, Winter G. (1989) Nature 341:544-546.
Wozniak-Knopp G, Stadlmann J, Rüker F (2012) PLoS ONE 7(1): e30083.
Yabukov et al. (1993) J Biol Chem. 268(25):18818-23.
Xu and Esko (2014) Annu Rev Biochem. 2014; 83:129-57

---

The invention claimed is:

1. A method for treating a disorder of lipoprotein metabolism in a subject, said method comprising obtaining a level of low-density lipoprotein-C (LDL-C) in a subject and wherein, if the level of LDL-C is above 3.3 mmol/L or above 2.6 mmol/L if the subject is at risk of heart disease, then administering to the subject a composition comprising:

A) a compound of formula (XXIV):

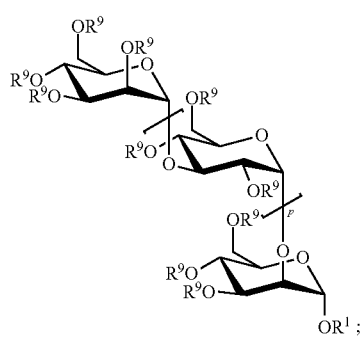

(XXIV)

wherein p is an integer equal to or greater than 1, and $R^9$ is $-SO_3^-$; and wherein $R^1$ is XI, XVI, XVII, or XIX;

B) a compound of formula (XXV):

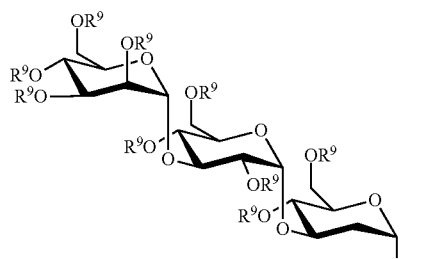

(XXV)

wherein $R^9$ is $-SO_3^-$; and wherein $R^1$ is XI, XVI, XVII, or XIX;

C) a compound of formula (XXVI):

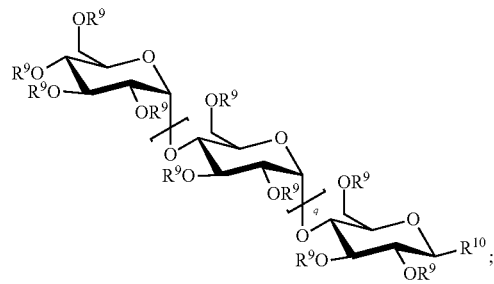

(XXVI)

wherein q is an integer, equal to or greater than 1;

$R^9$ is $-SO_3^-$; and $R^{10}$ is $-O-R^1$, wherein $R^1$ is XI, XVI, XVII, XIX, or comprises or consists of a group of formula (XXI) or formula (XXII):

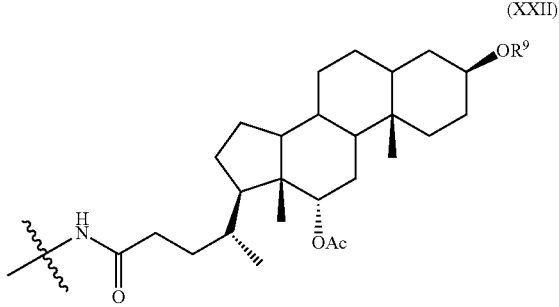

(XXII)

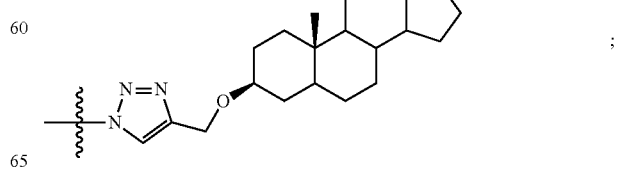

(XXI)

D) a compound of formula (XXVII):
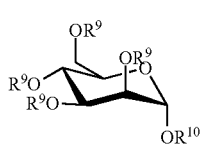
(XXVII)
wherein
R⁹ is —SO₃⁻; and
R¹⁰ comprises or consists of a group of formula (XXI) or formula (XXII):
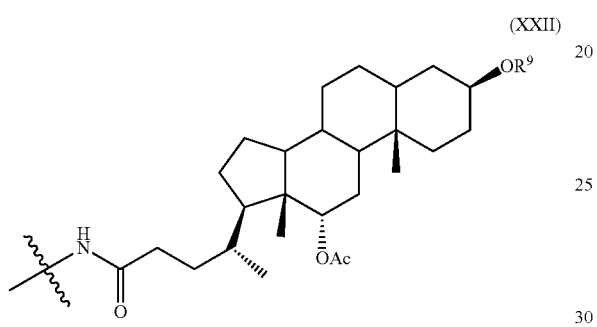
(XXII)
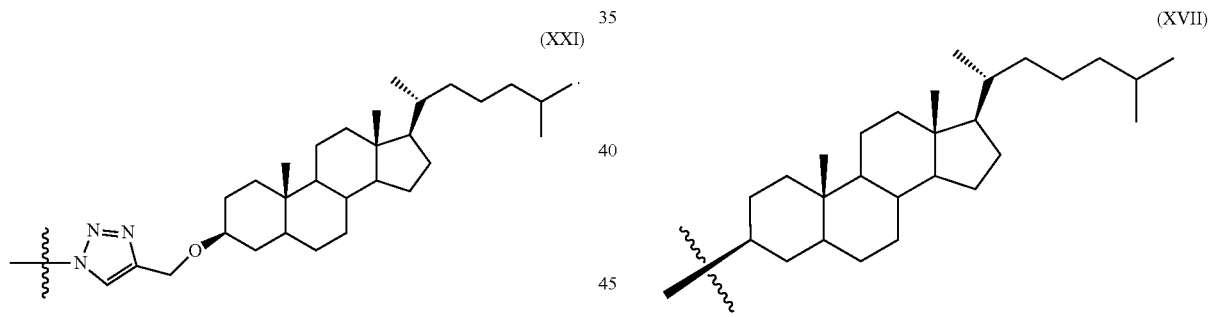
(XXI)
2. The method according to claim 1, wherein R¹ comprises or consists of a group selected from:
A) A group of formula (XI):
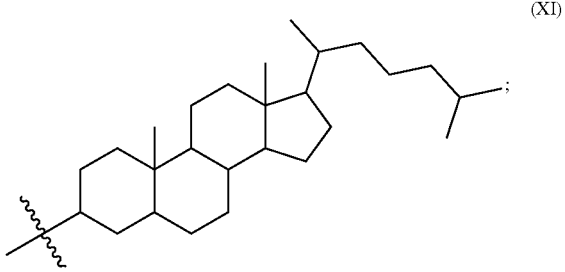 [SMILES: *C1CCC2(C)C(CCC3C2CCC2(C)C(C(C)CCCC(C)C)CCC32)C1]
(XI)
B) a group of formula (XVI);
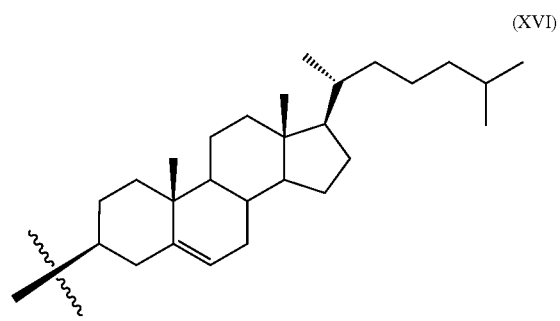
(XVI)
C) a group of formula (XVII);
(XVII)
or
D) a group of formula (XIX);
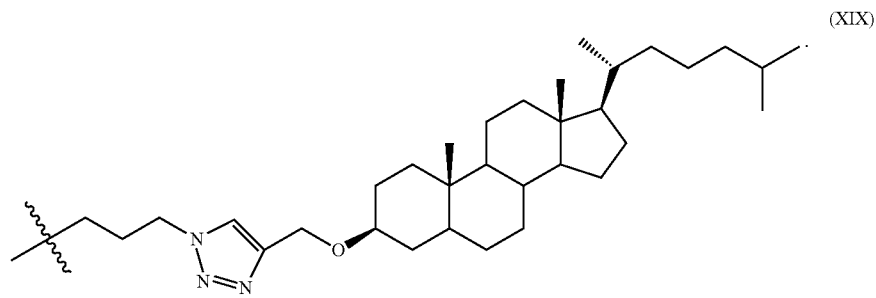 [SMILES: *CCCn1cc(CO[C@H]2CC[C@@]3(C)C(CCC4C3CC[C@@]3(C)C4CC[C@@H]3[C@H](C)CCCC(C)C)C2)nn1]
(XIX)

3. The method according to claim 1, wherein the compound of formula (XXVI) is compound (X):

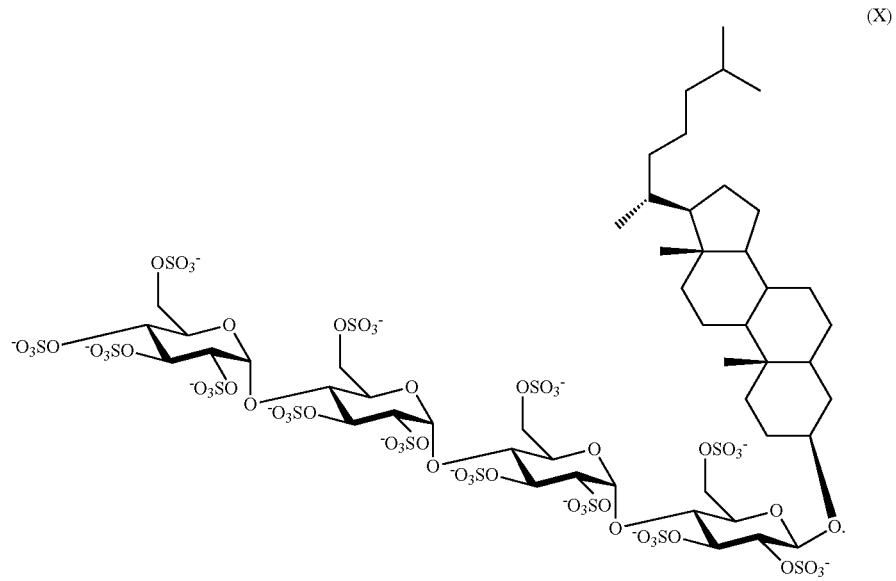

4. The method according to claim 1, wherein the composition comprises a compound selected from the group consisting of:
A) A compound of formula (XXIV) wherein p is 2 and $R^1$ is of formula (XVII):

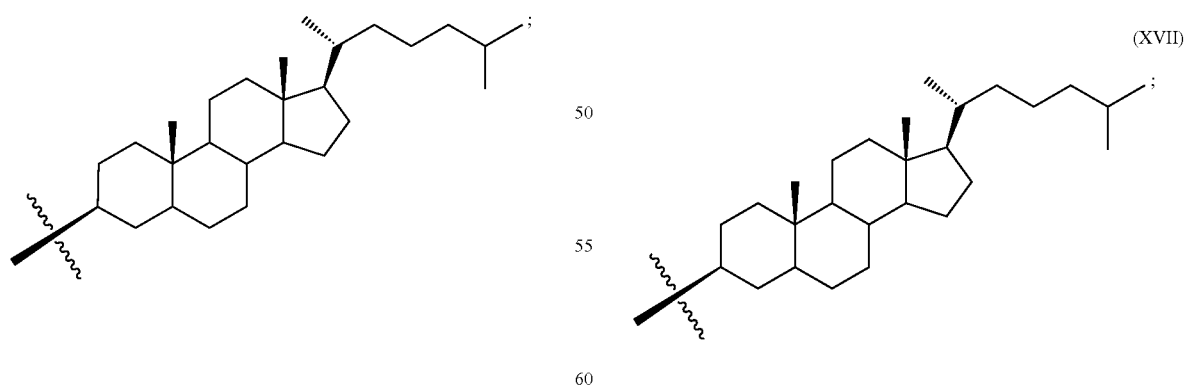

B) A compound of formula (XXIV) wherein p is 3 and $R^1$ is formula (XVII);
C) A compound of formula (XXIV) wherein p is 0 and $R^1$ is formula (XVII);
D) A compound of formula (XXIV) wherein p is 1 and $R^1$ is formula (XVII); and
E) A compound of formula (XXIV) wherein p is 1 and $R^1$ is formula (XIX).

5. The method according to claim 1, wherein the composition comprises:
A) A compound of formula (XXV) wherein $R^1$ is formula (XVII):

or

B) A compound of formula (XXV) wherein $R^1$ is formula (XIX):

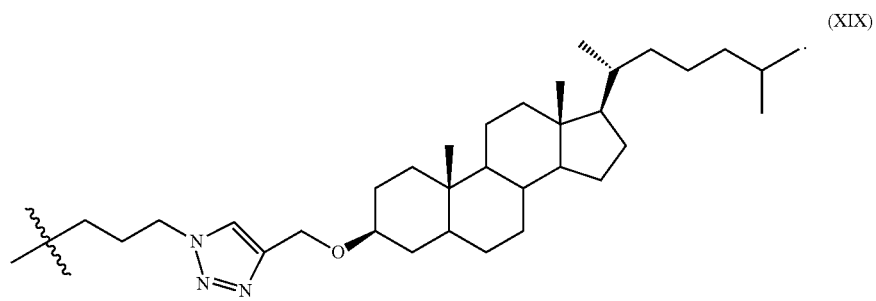 [SMILES: *CCCn1cc(CO[C@H]2CC[C@@]3(C)C(CCC4C3CC[C@@]3(C)C4CC[C@@H]3[C@H](C)CCCC(C)C)C2)nn1]

(XIX)

6. The method according to claim 1, wherein the composition comprises a compound selected from the group consisting of:
A) A compound of formula (XXVI), wherein q is 2 and $R^{10}$ is —O-formula (XVII):

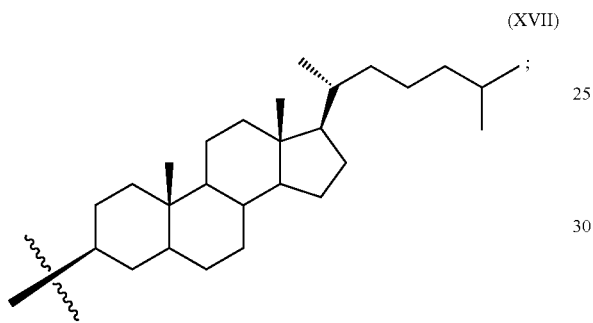

(XVII)

B) A compound of formula (XXVI), wherein q is 1 and $R^{10}$ is formula (XVII); and
C) A compound of formula (XXVI), wherein q is 1 and $R^{10}$ is —O-formula (XVII).

7. The method according to claim 1, wherein the compound is of formula (XXVII) and $R^{10}$ is formula (XVII).

8. The method according to claim 1, wherein the compound is conjugated to a dendritic structure of the formula:

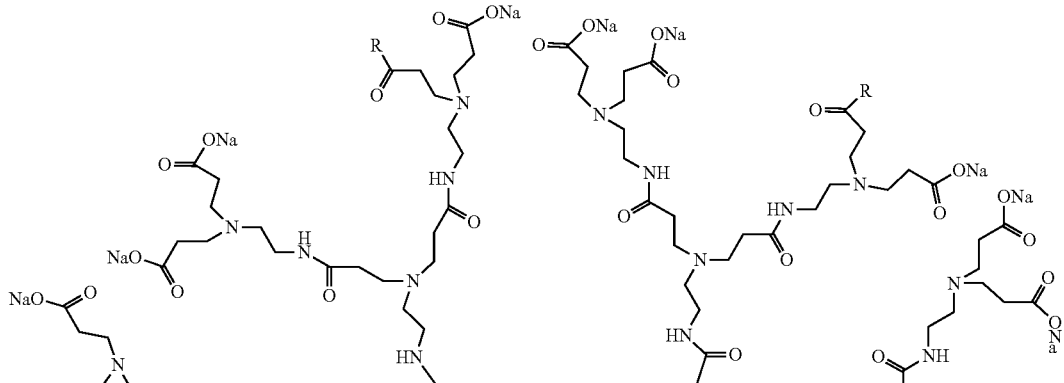

-continued

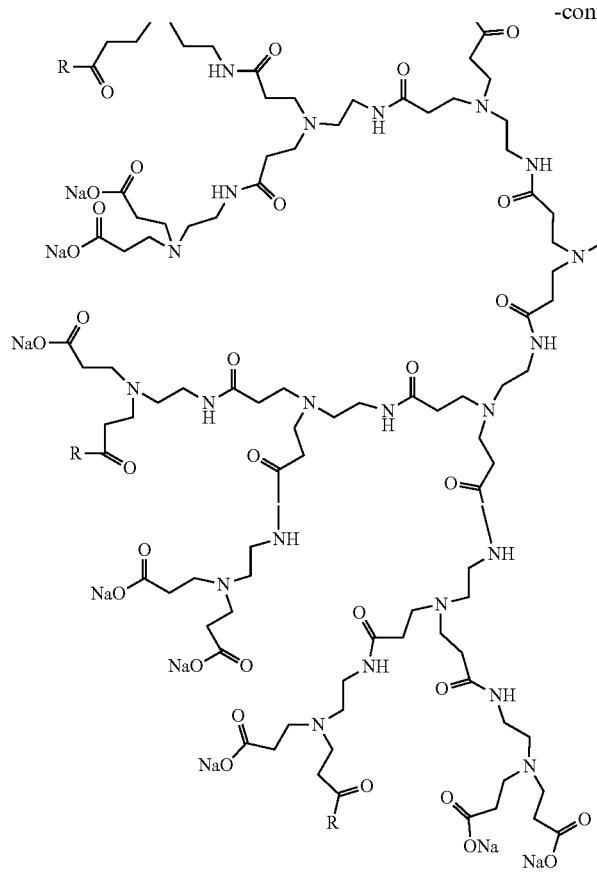

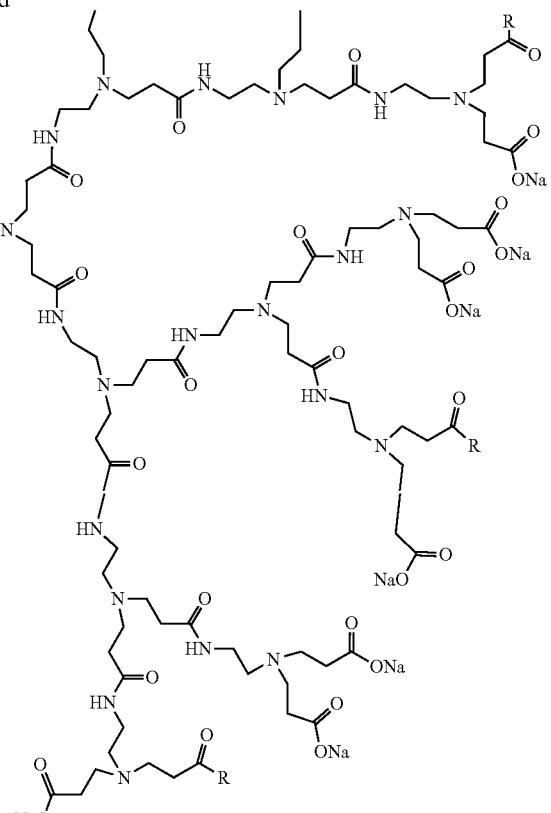

wherein the compound is conjugated as R.

9. The method according to claim 1, wherein said compound binds to one or more amino acids selected from the group consisting of R93, R96, R97, R104, R105, K136, H139, R165 and R167 of PCSK9 (SEQ ID NO: 1).

10. The method according to claim 1, wherein the LDL-C is above 3.3 mmol/kg or above 2.6 mmol/kg if the subject is at risk of heart disease due to a disorder of lipoprotein metabolism selected from the group consisting of diabetes, obesity, metabolic syndrome, xanthoma, hypercholesterolemia, familial hypercholesterolemia, dyslipidemia, hyperlipidemia, sitosterolemia, hypertension, angina, acute coronary syndrome, vascular inflammation and sepsis.

11. The method according to claim 1, wherein p is 0-7 and $R^1$ comprises a group with a formula Formula (XI):

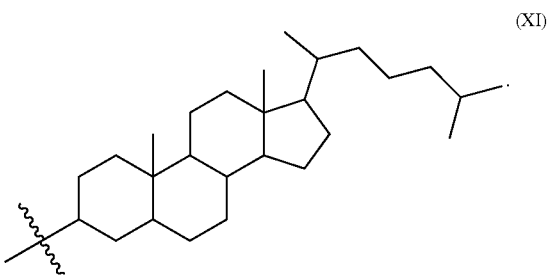 [SMILES: *C1CCC2(C)C(CCC3C2CCC2(C)C(C(C)CCCC(C)C)CCC32)C1]

(XI)

12. A method for reducing plasma lipoprotein levels in a subject in need thereof, said method comprising the step of administering to said subject a composition as defined in claim 1.

* * * * *

SEQUENCE LISTING

```
<160> NUMBER OF SEQ ID NOS: 21

<210> SEQ ID NO 1
<211> LENGTH: 692
<212> TYPE: PRT
<213> ORGANISM: Homo sapiens
<220> FEATURE:
<221> NAME/KEY: BINDING
<222> LOCATION: (78)..(167)
<223> OTHER INFORMATION: HSPG binding site
<220> FEATURE:
<221> NAME/KEY: MISC_FEATURE
<222> LOCATION: (93)..(93)
<223> OTHER INFORMATION: R93
<220> FEATURE:
<221> NAME/KEY: MISC_FEATURE
<222> LOCATION: (96)..(96)
<223> OTHER INFORMATION: R96
<220> FEATURE:
<221> NAME/KEY: MISC_FEATURE
<222> LOCATION: (97)..(97)
<223> OTHER INFORMATION: R97
<220> FEATURE:
<221> NAME/KEY: MISC_FEATURE
<222> LOCATION: (104)..(104)
<223> OTHER INFORMATION: R104
<220> FEATURE:
<221> NAME/KEY: MISC_FEATURE
<222> LOCATION: (105)..(105)
<223> OTHER INFORMATION: R105
<220> FEATURE:
<221> NAME/KEY: MISC_FEATURE
<222> LOCATION: (136)..(136)
<223> OTHER INFORMATION: K136
<220> FEATURE:
<221> NAME/KEY: MISC_FEATURE
<222> LOCATION: (139)..(139)
<223> OTHER INFORMATION: H139
<220> FEATURE:
<221> NAME/KEY: MISC_FEATURE
```

```
<222> LOCATION: (165)..(165)
<223> OTHER INFORMATION: R165
<220> FEATURE:
<221> NAME/KEY: MISC_FEATURE
<222> LOCATION: (167)..(167)
<223> OTHER INFORMATION: R167

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
```

```
              370                 375                 380
Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
        690

<210> SEQ ID NO 2
<211> LENGTH: 318
<212> TYPE: DNA
<213> ORGANISM: Artificial sequence
<220> FEATURE:
<223> OTHER INFORMATION: Sequences obtained by sequencing of the
      variable regions of the immunoglobulin genes expressed by rat
      hybridomas BNT-8H4-B8/C7-E11, BNT-5E11-D4/G1-E4
<220> FEATURE:
<221> NAME/KEY: CDS
<222> LOCATION: (1)..(318)
<223> OTHER INFORMATION: BNT-8H4-B8/C7-E11_VK
<220> FEATURE:
<221> NAME/KEY: V_region
<222> LOCATION: (1)..(69)
<220> FEATURE:
```

```
<221> NAME/KEY: V_segment
<222> LOCATION: (70)..(102)
<223> OTHER INFORMATION: CDR1
<220> FEATURE:
<221> NAME/KEY: V_region
<222> LOCATION: (103)..(147)
<220> FEATURE:
<221> NAME/KEY: V_segment
<222> LOCATION: (148)..(168)
<223> OTHER INFORMATION: CDR2
<220> FEATURE:
<221> NAME/KEY: V_region
<222> LOCATION: (169)..(264)
<220> FEATURE:
<221> NAME/KEY: V_segment
<222> LOCATION: (265)..(288)
<223> OTHER INFORMATION: CDR3
<220> FEATURE:
<221> NAME/KEY: J_segment
<222> LOCATION: (289)..(318)

<400> SEQUENCE: 2
```

| | | | | | | | | | | | | | | | | |
|---|---|---|---|---|---|---|---|---|---|---|---|---|---|---|---|---|
| gat | att | gtg | atg | acc | cag | tct | ccc | tca | ctc | ctg | tct | gca | tct | gtg | gga | 48 |
| Asp | Ile | Val | Met | Thr | Gln | Ser | Pro | Ser | Leu | Leu | Ser | Ala | Ser | Val | Gly | |
| 1 | | | | 5 | | | | | 10 | | | | | 15 | | |
| gac | aga | gtc | act | ctt | agc | tgc | aaa | gga | agt | cag | aat | att | aac | aat | tac | 96 |
| Asp | Arg | Val | Thr | Leu | Ser | Cys | Lys | Gly | Ser | Gln | Asn | Ile | Asn | Asn | Tyr | |
| | | | 20 | | | | | 25 | | | | | 30 | | | |
| tta | gcc | tgg | tac | caa | caa | aag | ctc | gga | gaa | gct | ccc | aaa | ctc | ctg | atc | 144 |
| Leu | Ala | Trp | Tyr | Gln | Gln | Lys | Leu | Gly | Glu | Ala | Pro | Lys | Leu | Leu | Ile | |
| | | 35 | | | | | 40 | | | | | 45 | | | | |
| tat | aat | aca | aac | agt | tta | caa | acg | ggc | atc | cca | tca | agg | ttc | agt | ggc | 192 |
| Tyr | Asn | Thr | Asn | Ser | Leu | Gln | Thr | Gly | Ile | Pro | Ser | Arg | Phe | Ser | Gly | |
| | 50 | | | | | 55 | | | | | 60 | | | | | |
| agt | gga | tct | ggt | aca | gat | tgc | aca | ctc | acc | atc | aga | agc | ctg | cag | cct | 240 |
| Ser | Gly | Ser | Gly | Thr | Asp | Cys | Thr | Leu | Thr | Ile | Arg | Ser | Leu | Gln | Pro | |
| 65 | | | | | 70 | | | | | 75 | | | | | 80 | |
| gaa | gat | gtt | gcc | aca | tat | ttc | tgc | tat | cag | tat | aac | aac | ggg | aac | acg | 288 |
| Glu | Asp | Val | Ala | Thr | Tyr | Phe | Cys | Tyr | Gln | Tyr | Asn | Asn | Gly | Asn | Thr | |
| | | | | 85 | | | | | 90 | | | | | 95 | | |
| ttt | gga | ggt | ggg | acc | aag | ctg | gag | ctg | aaa | | | | | | | 318 |
| Phe | Gly | Gly | Gly | Thr | Lys | Leu | Glu | Leu | Lys | | | | | | | |
| | | | 100 | | | | | 105 | | | | | | | | |

```
<210> SEQ ID NO 3
<211> LENGTH: 106
<212> TYPE: PRT
<213> ORGANISM: Artificial sequence
<220> FEATURE:
<223> OTHER INFORMATION: Synthetic Construct

<400> SEQUENCE: 3

Asp Ile Val Met Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
                20                  25                  30

Leu Ala Trp Tyr Gln Gln Lys Leu Gly Glu Ala Pro Lys Leu Leu Ile
            35                  40                  45

Tyr Asn Thr Asn Ser Leu Gln Thr Gly Ile Pro Ser Arg Phe Ser Gly
        50                  55                  60

Ser Gly Ser Gly Thr Asp Cys Thr Leu Thr Ile Arg Ser Leu Gln Pro
65                  70                  75                  80

Glu Asp Val Ala Thr Tyr Phe Cys Tyr Gln Tyr Asn Asn Gly Asn Thr
                85                  90                  95
```

```
Phe Gly Gly Gly Thr Lys Leu Glu Leu Lys
            100                 105
```

<210> SEQ ID NO 4
<211> LENGTH: 336
<212> TYPE: DNA
<213> ORGANISM: Artificial sequence
<220> FEATURE:
<223> OTHER INFORMATION: Sequences obtained by sequencing of the
      variable regions of the immunoglobulin genes expressed by rat
      hybridomas BNT-8H4-B8/C7-E11, BNT-5E11-D4/G1-E4
<220> FEATURE:
<221> NAME/KEY: CDS
<222> LOCATION: (1)..(336)
<223> OTHER INFORMATION: BNT-5E11-D4/G1-E4_VK
<220> FEATURE:
<221> NAME/KEY: V_region
<222> LOCATION: (1)..(69)
<223> OTHER INFORMATION: FWR1
<220> FEATURE:
<221> NAME/KEY: V_segment
<222> LOCATION: (70)..(117)
<223> OTHER INFORMATION: CDR1
<220> FEATURE:
<221> NAME/KEY: V_region
<222> LOCATION: (118)..(162)
<223> OTHER INFORMATION: FWR2
<220> FEATURE:
<221> NAME/KEY: V_segment
<222> LOCATION: (163)..(183)
<223> OTHER INFORMATION: CDR2
<220> FEATURE:
<221> NAME/KEY: V_region
<222> LOCATION: (184)..(279)
<223> OTHER INFORMATION: FWR3
<220> FEATURE:
<221> NAME/KEY: V_segment
<222> LOCATION: (280)..(306)
<223> OTHER INFORMATION: CDR3
<220> FEATURE:
<221> NAME/KEY: J_segment
<222> LOCATION: (307)..(336)
<223> OTHER INFORMATION: JK

<400> SEQUENCE: 4

```
gat gtt gtg ttg aca caa act cca gtt ttc ctg tct gtc aca ctt gga      48
Asp Val Val Leu Thr Gln Thr Pro Val Phe Leu Ser Val Thr Leu Gly
1               5                   10                  15 gat cag act tct ata tct tgt agg tct agt cag agt ctg gaa tat agt      96
Asp Gln Thr Ser Ile Ser Cys Arg Ser Ser Gln Ser Leu Glu Tyr Ser
            20                  25                  30 gat gga tac act tat ttg gaa tgg tac cta cag aaa ccg ggc cag tct     144
Asp Gly Tyr Thr Tyr Leu Glu Trp Tyr Leu Gln Lys Pro Gly Gln Ser
        35                  40                  45 cca cag ctc ctc atc tat gaa gtt tcc aac cga ttt tct ggg gtc cca     192
Pro Gln Leu Leu Ile Tyr Glu Val Ser Asn Arg Phe Ser Gly Val Pro
    50                  55                  60 gac agg ttc att ggc agt ggg tca ggg aca gat ttc acc ctc aag atc     240
Asp Arg Phe Ile Gly Ser Gly Ser Gly Thr Asp Phe Thr Leu Lys Ile
65                  70                  75                  80 agc aga gta gag cct gag gac ttg gga gtt tat tac tgc ttc caa ggt     288
Ser Arg Val Glu Pro Glu Asp Leu Gly Val Tyr Tyr Cys Phe Gln Gly
                85                  90                  95 aca cat gat cct ctc acg ttc ggt tct ggg acc aag ctg gag atc aaa     336
Thr His Asp Pro Leu Thr Phe Gly Ser Gly Thr Lys Leu Glu Ile Lys
            100                 105                 110
```

<210> SEQ ID NO 5
<211> LENGTH: 112
<212> TYPE: PRT

<213> ORGANISM: Artificial sequence
<220> FEATURE:
<223> OTHER INFORMATION: Synthetic Construct

<400> SEQUENCE: 5

```
Asp Val Val Leu Thr Gln Thr Pro Val Phe Leu Ser Val Thr Leu Gly
1               5                   10                  15

Asp Gln Thr Ser Ile Ser Cys Arg Ser Gln Ser Leu Glu Tyr Ser
            20                  25                  30

Asp Gly Tyr Thr Tyr Leu Glu Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Gly
                85                  90                  95

Thr His Asp Pro Leu Thr Phe Gly Ser Gly Thr Lys Leu Glu Ile Lys
            100                 105                 110
```

<210> SEQ ID NO 6
<211> LENGTH: 336
<212> TYPE: DNA
<213> ORGANISM: Artificial sequence
<220> FEATURE:
<223> OTHER INFORMATION: Sequences obtained by sequencing of the
      variable regions of the immunoglobulin genes expressed by rat
      hybridomas BNT-8H4-B8/C7-E11, BNT-5E11-D4/G1-E4
<220> FEATURE:
<221> NAME/KEY: CDS
<222> LOCATION: (1)..(336)
<223> OTHER INFORMATION: BNT-5E11-D4/G1-E4_VH
<220> FEATURE:
<221> NAME/KEY: V_region
<222> LOCATION: (1)..(90)
<223> OTHER INFORMATION: FWR1
<220> FEATURE:
<221> NAME/KEY: V_segment
<222> LOCATION: (91)..(108)
<223> OTHER INFORMATION: CDR1
<220> FEATURE:
<221> NAME/KEY: V_region
<222> LOCATION: (109)..(150)
<223> OTHER INFORMATION: FWR2
<220> FEATURE:
<221> NAME/KEY: V_segment
<222> LOCATION: (151)..(198)
<223> OTHER INFORMATION: CDR2
<220> FEATURE:
<221> NAME/KEY: V_region
<222> LOCATION: (199)..(294)
<223> OTHER INFORMATION: FWR3
<220> FEATURE:
<221> NAME/KEY: V_segment
<222> LOCATION: (295)..(303)
<223> OTHER INFORMATION: CDR3
<220> FEATURE:
<221> NAME/KEY: J_segment
<222> LOCATION: (304)..(336)
<223> OTHER INFORMATION: JH

<400> SEQUENCE: 6

```
gag gtg cag ctg cag gag tca gga cct ggc ctt gtg aaa cct tca cag      48
Glu Val Gln Leu Gln Glu Ser Gly Pro Gly Leu Val Lys Pro Ser Gln
1               5                   10                  15 tca ctc tcc ctc acc tgt tct gtc act ggt tac acc att acc agt ggt      96
Ser Leu Ser Leu Thr Cys Ser Val Thr Gly Tyr Thr Ile Thr Ser Gly
            20                  25                  30
```

```
tat gat tgg agc tgg atc cgg agg ttc cca gga aat aca atg gag tgg      144
Tyr Asp Trp Ser Trp Ile Arg Arg Phe Pro Gly Asn Thr Met Glu Trp
        35                  40                  45 atg gga gac ata agt tac agt ggt agc act aac tac aac cca tcg ctc      192
Met Gly Asp Ile Ser Tyr Ser Gly Ser Thr Asn Tyr Asn Pro Ser Leu
 50                  55                  60 aaa agt cga gtc tcc att aca aga gac aca tcc aag aat cag ttc ttc      240
Lys Ser Arg Val Ser Ile Thr Arg Asp Thr Ser Lys Asn Gln Phe Phe
 65                  70                  75                  80 ctg cag ttg aac tct gta act act ggg gat aca gcc aca tat tac tgt      288
Leu Gln Leu Asn Ser Val Thr Thr Gly Asp Thr Ala Thr Tyr Tyr Cys
                     85                  90                  95 gca aaa cta ccc ggc tgg ggc caa ggc act ctg gtc act gtc tct tca      336
Ala Lys Leu Pro Gly Trp Gly Gln Gly Thr Leu Val Thr Val Ser Ser
                100                 105                 110

<210> SEQ ID NO 7
<211> LENGTH: 112
<212> TYPE: PRT
<213> ORGANISM: Artificial sequence
<220> FEATURE:
<223> OTHER INFORMATION: Synthetic Construct

<400> SEQUENCE: 7

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr Ser Gly
            20                  25                  30

Tyr Asp Trp Ser Trp Ile Arg Arg Phe Pro Gly Asn Thr Met Glu Trp
        35                  40                  45

Met Gly Asp Ile Ser Tyr Ser Gly Ser Thr Asn Tyr Asn Pro Ser Leu
 50                  55                  60

Lys Ser Arg Val Ser Ile Thr Arg Asp Thr Ser Lys Asn Gln Phe Phe
 65                  70                  75                  80

Leu Gln Leu Asn Ser Val Thr Thr Gly Asp Thr Ala Thr Tyr Tyr Cys
                     85                  90                  95

Ala Lys Leu Pro Gly Trp Gly Gln Gly Thr Leu Val Thr Val Ser Ser
                100                 105                 110

<210> SEQ ID NO 8
<211> LENGTH: 354
<212> TYPE: DNA
<213> ORGANISM: Artificial sequence
<220> FEATURE:
<223> OTHER INFORMATION: Sequences obtained by sequencing of the
      variable regions of the immunoglobulin genes expressed by rat
      hybridomas BNT-8H4-B8/C7-E11, BNT-5E11-D4/G1-E4
<220> FEATURE:
<221> NAME/KEY: CDS
<222> LOCATION: (1)..(354)
<223> OTHER INFORMATION: BNT-8H4-B8/C7-E11_VH
<220> FEATURE:
<221> NAME/KEY: V_region
<222> LOCATION: (1)..(90)
<223> OTHER INFORMATION: FWR1
<220> FEATURE:
<221> NAME/KEY: V_segment
<222> LOCATION: (91)..(111)
<223> OTHER INFORMATION: CDR1
<220> FEATURE:
<221> NAME/KEY: V_region
<222> LOCATION: (112)..(153)
<223> OTHER INFORMATION: FWR2
<220> FEATURE:
<221> NAME/KEY: V_segment
<222> LOCATION: (154)..(201)
```

```
<223> OTHER INFORMATION: CDR2
<220> FEATURE:
<221> NAME/KEY: V_region
<222> LOCATION: (202)..(297)
<223> OTHER INFORMATION: FWR3
<220> FEATURE:
<221> NAME/KEY: V_segment
<222> LOCATION: (298)..(321)
<223> OTHER INFORMATION: CDR3
<220> FEATURE:
<221> NAME/KEY: J_segment
<222> LOCATION: (322)..(354)
<223> OTHER INFORMATION: JH

<400> SEQUENCE: 8 cag gtt act ctg aaa gag tct ggc cct ggg ata ttg cag cct tcc cag      48
Gln Val Thr Leu Lys Glu Ser Gly Pro Gly Ile Leu Gln Pro Ser Gln
1               5                   10                  15 acc ctc agt ctg act tgc tct ttc tct ggg ttt tca ctg agc agt tca      96
Thr Leu Ser Leu Thr Cys Ser Phe Ser Gly Phe Ser Leu Ser Ser Ser
            20                  25                  30 ggt ata tgt gtg agc tgg att cgt cag cct tca ggg aag ggt ctg gag     144
Gly Ile Cys Val Ser Trp Ile Arg Gln Pro Ser Gly Lys Gly Leu Glu
        35                  40                  45 tgg ctg gca act att tgt tgg gag gat agt aag ggc tac aac cct tct     192
Trp Leu Ala Thr Ile Cys Trp Glu Asp Ser Lys Gly Tyr Asn Pro Ser
50                  55                  60 ctg aag aac cgg ctc acg atc tcc aag gac acc tcc aac aac caa gca     240
Leu Lys Asn Arg Leu Thr Ile Ser Lys Asp Thr Ser Asn Asn Gln Ala
65                  70                  75                  80 ctc ctc agg atc acc agt gtg gac act gca gat acc gcc att tac tac     288
Leu Leu Arg Ile Thr Ser Val Asp Thr Ala Asp Thr Ala Ile Tyr Tyr
                85                  90                  95 tgt gct cgg gtt tat tac tgg tac ttt gac ttc tgg ggc cca gga acc     336
Cys Ala Arg Val Tyr Tyr Trp Tyr Phe Asp Phe Trp Gly Pro Gly Thr
            100                 105                 110 atg gtc acc gtg tcc tca                                              354
Met Val Thr Val Ser Ser
        115

<210> SEQ ID NO 9
<211> LENGTH: 118
<212> TYPE: PRT
<213> ORGANISM: Artificial sequence
<220> FEATURE:
<223> OTHER INFORMATION: Synthetic Construct

<400> SEQUENCE: 9

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Ser Ser
            20                  25                  30

Gly Ile Cys Val Ser Trp Ile Arg Gln Pro Ser Gly Lys Gly Leu Glu
        35                  40                  45

Trp Leu Ala Thr Ile Cys Trp Glu Asp Ser Lys Gly Tyr Asn Pro Ser
50                  55                  60

Leu Lys Asn Arg Leu Thr Ile Ser Lys Asp Thr Ser Asn Asn Gln Ala
65                  70                  75                  80

Leu Leu Arg Ile Thr Ser Val Asp Thr Ala Asp Thr Ala Ile Tyr Tyr
                85                  90                  95

Cys Ala Arg Val Tyr Tyr Trp Tyr Phe Asp Phe Trp Gly Pro Gly Thr
            100                 105                 110
```

```
Met Val Thr Val Ser Ser
        115

<210> SEQ ID NO 10
<211> LENGTH: 6
<212> TYPE: PRT
<213> ORGANISM: Artificial sequence
<220> FEATURE:
<223> OTHER INFORMATION: CDR1 of SEQ ID NO: 7

<400> SEQUENCE: 10

Ser Gly Tyr Asp Trp Ser
1               5

<210> SEQ ID NO 11
<211> LENGTH: 16
<212> TYPE: PRT
<213> ORGANISM: Artificial sequence
<220> FEATURE:
<223> OTHER INFORMATION: CDR2 of SEQ ID NO: 7

<400> SEQUENCE: 11

Asp Ile Ser Tyr Ser Gly Ser Thr Asn Tyr Asn Pro Ser Leu Lys Ser
1               5                   10                  15

<210> SEQ ID NO 12
<211> LENGTH: 3
<212> TYPE: PRT
<213> ORGANISM: Artificial sequence
<220> FEATURE:
<223> OTHER INFORMATION: CDR3 of SEQ ID NO: 7

<400> SEQUENCE: 12

Leu Pro Gly
1

<210> SEQ ID NO 13
<211> LENGTH: 16
<212> TYPE: PRT
<213> ORGANISM: Artificial sequence
<220> FEATURE:
<223> OTHER INFORMATION: CDR1 of SEQ ID NO: 5

<400> SEQUENCE: 13

Arg Ser Ser Gln Ser Leu Glu Tyr Ser Asp Gly Tyr Thr Tyr Leu Glu
1               5                   10                  15

<210> SEQ ID NO 14
<211> LENGTH: 7
<212> TYPE: PRT
<213> ORGANISM: Artificial sequence
<220> FEATURE:
<223> OTHER INFORMATION: CDR2 of SEQ ID NO: 5

<400> SEQUENCE: 14

Glu Val Ser Asn Arg Phe Ser
1               5

<210> SEQ ID NO 15
<211> LENGTH: 9
<212> TYPE: PRT
<213> ORGANISM: Artificial sequence
<220> FEATURE:
<223> OTHER INFORMATION: CDR3 of SEQ ID NO: 5

<400> SEQUENCE: 15

Phe Gln Gly Thr His Asp Pro Leu Thr
```

```
<210> SEQ ID NO 16
<211> LENGTH: 7
<212> TYPE: PRT
<213> ORGANISM: Artificial sequence
<220> FEATURE:
<223> OTHER INFORMATION: CDR1 of SEQ ID NO: 9

<400> SEQUENCE: 16

Ser Ser Gly Ile Cys Val Ser
1               5

<210> SEQ ID NO 17
<211> LENGTH: 16
<212> TYPE: PRT
<213> ORGANISM: Artificial sequence
<220> FEATURE:
<223> OTHER INFORMATION: CDR2 of SEQ ID NO: 9

<400> SEQUENCE: 17

Thr Ile Cys Trp Glu Asp Ser Lys Gly Tyr Asn Pro Ser Leu Lys Asn
1               5                   10                  15

<210> SEQ ID NO 18
<211> LENGTH: 8
<212> TYPE: PRT
<213> ORGANISM: Artificial sequence
<220> FEATURE:
<223> OTHER INFORMATION: CDR3 of SEQ ID NO: 9

<400> SEQUENCE: 18

Val Tyr Tyr Trp Tyr Phe Asp Phe
1               5

<210> SEQ ID NO 19
<211> LENGTH: 11
<212> TYPE: PRT
<213> ORGANISM: Artificial sequence
<220> FEATURE:
<223> OTHER INFORMATION: CDR1 of SEQ ID NO: 3

<400> SEQUENCE: 19

Lys Gly Ser Gln Asn Ile Asn Asn Tyr Leu Ala
1               5                   10

<210> SEQ ID NO 20
<211> LENGTH: 7
<212> TYPE: PRT
<213> ORGANISM: Artificial sequence
<220> FEATURE:
<223> OTHER INFORMATION: CDR2 of SEQ ID NO: 3

<400> SEQUENCE: 20

Asn Thr Asn Ser Leu Gln Thr
1               5
```

```
<210> SEQ ID NO 21
<211> LENGTH: 8
<212> TYPE: PRT
<213> ORGANISM: Artificial sequence
<220> FEATURE:
<223> OTHER INFORMATION: CDR3  of SEQ ID NO: 3

<400> SEQUENCE: 21

Tyr Gln Tyr Asn Asn Gly Asn Thr
1               5
```